US012806394B2

(12) United States Patent
Um Nlend et al.

(10) Patent No.: US 12,806,394 B2
(45) Date of Patent: Nov. 24, 2026

(54) INK APPLICATORS

(71) Applicant: TMI Acquisition, LLC, Tucson, AZ (US)

(72) Inventors: Ingrid Um Nlend, Toronto (CA); Tyler J. Handley, Toronto (CA); Motaz Adam, Toronto (CA)

(73) Assignee: TMI ACQUISITION, LLC, Tucson, AZ (US)

( * ) Notice: Subject to any disclaimer, the term of this patent is extended or adjusted under 35 U.S.C. 154(b) by 166 days.

(21) Appl. No.: 18/686,344

(22) PCT Filed: Aug. 23, 2022

(86) PCT No.: PCT/CA2022/051273
§ 371 (c)(1),
(2) Date: Feb. 23, 2024

(87) PCT Pub. No.: WO2023/023851
PCT Pub. Date: Mar. 2, 2023

(65) Prior Publication Data

US 2025/0186755 A1 Jun. 12, 2025

Related U.S. Application Data

(60) Provisional application No. 63/236,968, filed on Aug. 25, 2021.

(51) Int. Cl.
*A61M 37/00* (2006.01)

(52) U.S. Cl.
CPC ................................ *A61M 37/0084* (2013.01)

(58) Field of Classification Search
CPC ................................ B43K 8/03; B43K 13/00
See application file for complete search history.

(56) References Cited

U.S. PATENT DOCUMENTS

| | | | | |
|---|---|---|---|---|
| 9,162,515 | B2 * | 10/2015 | Maruyama | B43K 5/18 |
| 9,193,212 | B2 * | 11/2015 | Henry | B43K 15/00 |

FOREIGN PATENT DOCUMENTS

| | | | | |
|---|---|---|---|---|
| CA | 2932703 | A1 | 12/2016 | |
| CA | 3129021 | A1 | 8/2020 | |
| CN | 205390735 | U | 7/2016 | |
| CN | 110226975 | A | 9/2019 | |
| FR | 3003860 | A1 * | 10/2014 | A61K 8/498 |

(Continued)

OTHER PUBLICATIONS

Machine Translation of FR 3003860 (Year: 2014).*

(Continued)

*Primary Examiner* — David P Angwin
*Assistant Examiner* — Bradley S Oliver
(74) *Attorney, Agent, or Firm* — Butzel Long; Gregory Ozga

(57) ABSTRACT

This disclosure relates to semi-permanent tattoos, ink applicators, and more particularly to semi-permanent tattoo applicators that dispense semi-permanent ink compositions. In some embodiments, an ink applicator a lower body coupled to an upper body, the upper body comprises: a nib comprising a first end that is external to the upper body and a second end internal to the upper body, wherein the nib is configured to dispense a semi-permanent ink.

30 Claims, 10 Drawing Sheets

(56) References Cited

FOREIGN PATENT DOCUMENTS

| | | | |
|---|---|---|---|
| WO | 2021248243 | A1 | 12/2021 |
| WO | 2022036113 | A1 | 2/2022 |

OTHER PUBLICATIONS

International Search Report and Written Opinion issued in International Application No. PCT/CA2022/051273 on Nov. 23, 2022 (9 pages).

Touyama et al., "Studies on the Blue Pigments Produced from Genipin and Methylamine. I. Structures of the Brownish-Red Pigments, Intermediates Leading to the Blue Pigments" Chemical and Pharmaceutical Bulletin, vol. 42, No. 3, pp. 668-673 (1994).

Touyama et al., "Studies on the Blue Pigments Produced from Genipin and Methylamine. II. On the Formation Mechanisms of Brownish-Red Intermediates Leading to the Blue Pigment Formation" Chemical and Pharmaceutical Bulletin, vol. 42, No. 8, pp. 1571-1578 (1994).

* cited by examiner

INK APPLICATORS

CROSS REFERENCE TO RELATED APPLICATIONS

This is a National Stage Application under 35 U.S.C. § 371 of International Application No. PCT/CA2022/051273, filed on Aug. 23, 2022, now published as WO 2023/023851 A1, which claims priority from U.S. Provisional Patent Application No. 63/236,968, filed on Aug. 25, 2021, the entire contents of which being incorporated herein by reference.

TECHNICAL FIELD

This disclosure relates to semi-permanent tattoos, ink applicators, and more particularly to semi-permanent tattoo applicators that dispense semi-permanent ink compositions.

BACKGROUND

Temporary or semi-permanent tattoo or body inks have been used throughout human history to decorate the body. Generally, temporary or semi-permanent tattoos are transferred to the skin through the direct exposure of the skin to tattoo ink over a designated incubation period. The quality of the transferred image and its duration on the skin can depend on the ink distribution profile in the outer layer of the skin called the stratum corneum. Current manufacturing processes for pre-fabricated tattoo designs include the utilization of flexographic or gravure printing, stencils, and inkjet printers. However, due to the barrier properties of the stratum corneum, many of the current methods require moderate oversight by the end user during the tattoo application process to ensure adequate ink delivery to the skin such that the tattoo ink develops properly.

SUMMARY

Provided herein are semi-permanent tattoos, ink applicators, and semi-permanent tattoo applicators that dispense semi-permanent ink compositions. In some embodiments, an ink applicator a lower body coupled to an upper body, the upper body comprises: a nib comprising a first end that is external to the upper body and a second end internal to the upper body, wherein the nib is configured to dispense a semi-permanent ink.

In some embodiments, an ink applicator, comprises a lower body, comprising a reservoir container contained in a cavity of the lower body a reservoir contained in a cavity of the reservoir container; and a semi-permanent ink contained in the reservoir.

In some embodiments, an ink applicator, comprises a lower body, comprising a reservoir contained in a cavity of the lower body; and a semi-permanent ink contained in the reservoir. In some embodiments, the reservoir comprises polyethylene terephthalate. In some embodiments, the polyethylene terephthalate is saturated in the semi-permanent ink. In some embodiments, the ink applicator further comprising an agitator contained in the reservoir. In some embodiments, the agitator is metallic.

In some embodiments, an ink applicator, comprises a lower body, comprising: a reservoir container contained in a cavity of the lower body; and a semi-permanent ink contained in the reservoir.

In some embodiments, an ink applicator, comprises a lower body comprising a semi-permanent ink contained in a cavity of the lower body.

In some embodiments, the lower body further comprises external threading coupleable to an upper body. In some embodiments, the upper body comprises a nib comprising a first end that is external to the upper body and a second end internal to the upper body, wherein the nib is configured to dispense the semi-permanent ink.

In some embodiments, an ink applicator, comprises a lower body coupled to an upper body, the upper body comprising: a nib comprising a first end that is external to the upper body and a second end internal to the upper body, wherein the nib is configured to dispense a semi-permanent ink. In some embodiments, the ink applicator further comprises a reservoir container contained in a cavity of the lower body. In some embodiments, the ink applicator further comprising a reservoir contained in a cavity of the reservoir container, wherein the semi-permanent ink is contained in the reservoir. In some embodiments, the reservoir comprises polyethylene terephthalate. In some embodiments, the polyethylene terephthalate is saturated in the semi-permanent ink.

In some embodiments, an ink applicator, comprises a lower body, comprising a reservoir container contained in a cavity of the lower body; a reservoir contained in a cavity of the reservoir container; and a semi-permanent ink contained in the reservoir; and an upper body coupled to the lower body, the upper body comprising a nib comprising a first end that is external to the upper body and a second end internal to the upper body.

In some embodiments, the reservoir comprises polyethylene terephthalate. In some embodiments, the polyethylene terephthalate is saturated in the semi-permanent ink.

In some embodiments, an ink applicator, comprises a lower body, comprising a reservoir container contained in a cavity of the lower body; a reservoir contained in a cavity of the reservoir container; and a semi-permanent ink contained in the reservoir; and an upper body coupled to the lower body, the upper body comprising: a nib comprising a first end that is external to the upper body and a second end internal to the upper body; and a transfer nib that contacts the second end of the nib and the semi-permanent ink contained in the reservoir.

In some embodiments, the ink applicator further comprising an agitator contained in the reservoir. In some embodiments, the agitator is metallic. In some embodiments, the agitator is a metallic bead. In some embodiments, the nib includes nylon brush fibers and is configured to couple to the transfer nib. In some embodiments, the nib includes a flexible and porous tip and is configured to couple to the transfer nib. In some embodiments, the semi-permanent ink is absorbed by the transfer nib and the semi-permanent ink absorbed by the nib it transferred to the second end of the nib. In some embodiments, the ink applicator further comprises a transfer casing adjacent to the first end of the nib. In some embodiments, the transfer casing couples the transfer nib to the nib. In some embodiments, the transfer casing secures the transfer nib to the upper body. In some embodiments, the transfer casing is configured to absorb excess semi-permanent ink from the reservoir.

In some embodiments, the second end of the nib contacts the semi-permanent ink contained in the reservoir. In some embodiments, the first end of the nib is configured to deposit the semi-permanent ink composition onto a substrate. In some embodiments, the substrate is paper. In some embodiments, the substrate is animal skin. In some embodiments, the reservoir is selectively removable. In some embodiments, the lower body further comprises a transparent window. In some embodiments, the reservoir is visible via the transparent window.

In some embodiments, the ink applicator further comprises external threading integrated to the lower body; and internal threading integrated to the upper body, wherein the external threading and the internal threading are complementary and couple the lower body to the upper body.

In some embodiments, the internal threading and the external threading couple the upper body and the lower body such that the cavity of the lower body is sealed. In some embodiments, the nib includes a firm round tip. In some embodiments, the nib includes a chiseled tip. In some embodiments, the nib includes a fine pointed tip. In some embodiments, the ink applicator further comprises a lid configured to cover the first end of the nib that is external to the upper body. In some embodiments, the lid provides a seal between the lid and the upper body. In some embodiments, the reservoir comprises a void. In some embodiments, the void is configured to contain a volume of semi-permanent ink. In some embodiments, the volume is about 0.5 mL to about 1.5 mL. In some embodiments, the volume is about 1.0 mL. In some embodiments, the ink applicator is a pen. In some embodiments, the ink applicator is a marker.

In some embodiments, an ink applicator system, comprises a reservoir comprising semi-permanent ink; and a plurality of nibs configured to contact the semi-permanent ink in the reservoir. In some embodiments, a first nib of the plurality of nibs includes a firm round tip. In some embodiments, a second nib of the plurality of nibs includes a chiseled tip. In some embodiments, a third nib of the plurality of nibs includes a fine pointed tip. In some embodiments, a fourth nib of the plurality of nibs includes nylon brush fibers. In some embodiments, a fifth nib of the plurality of nibs includes a flexible porous tip. In some embodiments, the ink applicator system further comprises a pouch of the semi-permanent ink. In some embodiments, the pouch includes a capacity of about 0.5 mL to about 1.5 mL for the semi-permanent ink. In some embodiments, the pouch includes a capacity of about 1.0 mL for the semi-permanent tattoo composition. In some embodiments, the reservoir further comprises polyethylene terephthalate. In some embodiments, the polyethylene terephthalate is saturated with the semi-permanent ink. In some embodiments, the plurality of nibs corresponds to a color of the semi-permanent ink. In some embodiments, the ink applicator system further comprises an ink applicator.

In some embodiments, disclosed herein is a method for applying ink onto skin, the method comprising coupling a nib to an upper body of an ink applicator comprising an ink composition; and applying the ink composition of the ink applicator to a portion of the skin. In some embodiments, the ink applicator is a marker. In some embodiments, the method further includes agitating the ink applicator to begin the flow of ink composition from a reservoir of the ink applicator to the nib.

In some embodiments, the method further comprises decoupling the upper body of the ink applicator from a lower body of the ink applicator; removing the reservoir from the lower body; and replacing the reservoir with a different reservoir. In some embodiments, the method further comprises decoupling the upper body of the ink applicator from a lower body of the ink applicator; removing the reservoir from the lower body; and filling the reservoir with additional ink composition.

In some embodiments, the method further comprises decoupling the nib from the ink applicator; coupling a different nib to the ink applicator; and applying the ink via the ink applicator and different nib to the portion of the skin.

In some embodiments, the semi-permanent ink comprises a semi-permanent colorant, wherein the semi-permanent colorant comprises genipin, a genipin derivative, lawsone, a lawsone derivative, or combinations thereof a solvent; and a film-forming agent.

In some embodiments, the genipin derivative is a compound of Formula I:

I

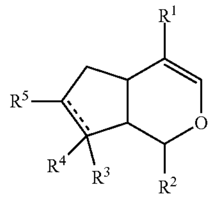

wherein:

$R^1$ is —C(═O)$OR^6$, $C_{1-6}$ alkyl, or $C_{6-10}$ aryl, wherein said $C_{1-6}$ alkyl and $C_{6-10}$ aryl are each optionally substituted with 1-5 $R^7$;

$R^6$ is H, $C_{1-6}$ alkyl, or $C_{6-10}$ aryl, wherein said $C_{1-6}$ alkyl and $C_{6-10}$ aryl are each optionally substituted with 1-5 $R^7$;

each $R^7$ is independently an electron withdrawing or an electron donating group;

$R^2$ is H, —$OR^9$, or OC(═O)$R^{9A}$;

$R^9$ is selected from the group consisting of: H, $C_{1-6}$ alkyl, $C_{6-10}$ aryl, and a hydroxyl-protecting group;

$R^{9A}$ is selected from $C_{1-6}$ alkyl and $C_{6-10}$ aryl; and the dotted line indicates the optional presence of a double bond;

wherein if the double bond is absent, then $R^4$ and $R^5$ together with the carbon atoms to which they are attached form a 3-4 membered heterocyclic ring and $R^3$ is —OH or —$CH_2OH$; or if the double bond is present, then $R^4$ and $R^5$ are absent and $R^3$ is selected from the group consisting of: —$NR^7R^8$, —$CH_2NR^7R^8$, —C(═O)$OR^{10}$, —C(═O)$NR^{10}R^{10}$, —CH(═O), phenyl, —$CHR^{10}R^{10}$, —CH═$CHR^{10}$, —CH═$CR^{10}R^{10}$, —$CH_2OR^{10}$, and phenyl substituted with 1-5 $R^7$;

wherein $R^{10}$ is selected from H, $C_{1-6}$ alkyl, alkoxy, oxo, —OH, —CH(═O), —C(═O)$OR^6$, phenyl, and phenyl substituted with 1-5 $R^7$; and $R^8$ is H or $R^7$.

In some embodiments, $R^1$ is —C(═O)$OR^6$ or phenyl substituted with 1-5 $R^7$;

$R^6$ is H, $C_{1-6}$ alkyl, or phenyl substituted with 1-5 $R^7$;

$R^2$ is H, —$OR^9$, or OC(═O)$R^9$;

$R^9$ is H or $C_{1-6}$ alkyl;

if the double bond is present, then $R^4$ and $R^5$ are absent and $R^3$ is selected from the group consisting of: —$NR^7R^8$, —$CH_2NR^7R^8$, —C(═O)$OR^{10}$, —CH(═O), phenyl, —$CHR^{10}R^{10}$, —CH═$CHR^{10}$, —$CH_2OR^{10}$, diethyl malonate, and phenyl substituted with 1-5 $R^7$; and $R^{10}$ is selected from H, $C_{1-6}$ alkyl, alkoxy, oxo, —OH, —CH(═O) and phenyl substituted with 1-5 $R^7$.

In some embodiments, the hydroxyl-protecting group is tri($C_{1-6}$ alkyl)silyl. In some embodiments, the hydroxyl-protecting group is tert-butyldimethylsilyl (TBS), trimethylsilyl (TMS), or triethylsilyl (TES). In some embodiments, $R^6$ is methyl. In some embodiments, $R^1$ is —C(═O)OR$^6$ and $R^6$ is methyl. In some embodiments, $R^1$ is —C(═O)OR$^6$ and $R^6$ is phenyl substituted with 1-5 $R^7$. In some embodiments, $R^2$ is —OC(═O)$CH_3$. In some embodiments, $R^2$ is —OH. In some embodiments, $R^2$ is —OR$^9$ and $R^9$ is selected from the group consisting of: H, $C_{1-6}$ alkyl, tert-butyldimethylsilyl (TBS), trimethylsilyl (TMS), triethylsilyl (TES), and $C_{6-10}$ aryl. In some embodiments, $R^9$ is H. In some embodiments, $R^9$ is tert-butyldimethylsilyl (TBS). In some embodiments, $R^9$ is —OH. In some embodiments, the double bond is absent. In some embodiments, wherein then $R^4$ and $R^5$ together with the carbon atoms to which they are attached form a 3-membered heterocyclic ring and $R^3$ is —$CH_2$OH. In some embodiments, the 3-membered heterocyclic ring is:

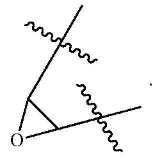 [SMILES: *C1OC1*]

In some embodiments, $R^4$ and $R^5$ together with the carbon atoms to which they are attached form a 4-membered heterocyclic ring and $R^3$ is —OH.

In some embodiments, the 4-membered ring is:

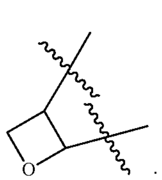 [SMILES: *C1COC1*]

In some embodiments, the double bond is present. In some embodiments, $R^1$ is phenyl substituted with 1-3 $R^7$. In some embodiments, $R^1$ is —C(═O)OR$^6$ and $R^6$ is phenyl substituted with 1-3 $R^7$. In some embodiments, $R^2$ is —OH and $R^3$ is $CH_2$OH. In some embodiments, $R^3$ is selected from the group consisting of: —NR$^7$R$^8$, —$CH_2$NR$^7$R$^8$, —C(═O)OR$^{10}$, —C(═O)N R$^{10}$R$^{10}$, —CH(═O), phenyl, —CHR$^{10}$R$^{10}$, —CH═CHR$^{10}$, —CH═CR$^{10}$R$^{10}$, —$CH_2$OR$^{10}$, and phenyl substituted with 1-5 $R^7$;

$R^1$ is —C(═O)OH;

$R^2$ is —OH; and $R^{10}$ is selected from H, $C_{1-6}$ alkyl, alkoxy, oxo, —OH, —CH(═O), —C(═O)OR$^6$, phenyl, and phenyl substituted with 1-5 $R^7$.

In some embodiments, $R^3$ is selected from the group consisting of:

—NR$^7$R$^8$, —$CH_2$—NR$^7$R$^8$, —C(═O)OR$^{10}$, —CH(═O), phenyl, —CHR$^{10}$R$^{10}$, —CH═CHR$^{10}$, C(═O)NR$^{10}$R$^{10}$, —$CH_2$OR$^{10}$, and phenyl substituted with 1-5 $R^7$;

$R^1$ is —C(═O)OH; and $R^2$ is —OR$^9$ and $R^9$ is selected from the group consisting of: H, $C_{1-6}$ alkyl, tert-butyldimethylsilyl (TBS), trimethylsilyl (TMS), triethylsilyl (TES), and $C_{6-10}$ aryl.

In some embodiments, $R^3$ is selected from the group consisting of:

—NR$^7$R$^8$, —$CH_2$—NR$^7$R$^8$, —C(═O)OR$^{10}$, —CH(═O), phenyl, —CHR$^{10}$R$^{10}$, —CH═CHR$^{10}$, —$CH_2$OR$^{10}$, diethyl malonate, and phenyl substituted with 1-5 $R^7$;

$R^1$ is —C(═O)OH; and $R^2$ is —OH.

In some embodiments, the genipin derivative is a compound selected from the group consisting of the compounds delineated in Table 1. In some embodiments, $R^7$ is selected from the group consisting of: —($C_{1-9}$ alkyl), —($C_{2-9}$ alkenyl), phenyl, —NR$^8$R$^8$, —OR$^8$, —NHC(═O)R$^8$, —OC(═O)R$^8$, —SR$^8$, —$CO_2^-$, —$SO_2CF_3$, —NO, —$NO_2$, —$SO_2$R$^8$, —CN, —CR$^{11}$, —COR$^{11}$, —CHO, —$CO_2$R$^8$, —C(═O)NR$^8$R$^8$, and halide;

wherein $R^8$ is selected from the group consisting of: H, —($C_{1-9}$ alkyl), and —($C_{2-9}$ alkenyl); and $R^{11}$ is halide.

In some embodiments, the lawsone derivative is the compound delineated in Table 4.

In some embodiments, the lawsone derivative is a compound of Formula III:

III

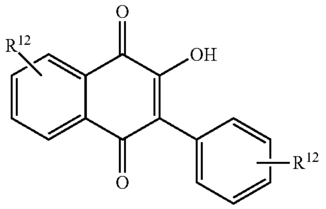

wherein $R^{12}$ is selected from the group consisting of: —($C_{1-9}$ alkyl), —($C_{2-9}$ alkenyl), phenyl, —NR$^8$R$^8$, —OR$^8$, —NHC(═O)R$^8$, —OC(═O)R$^8$, —SR$^8$, —$CO_2^-$, —$SO_2CF_3$, —NO, —$NO_2$, —$SO_2$R$^8$, —CN, —CR$^{11}_3$, —COR$^{11}$, —CHO, —$CO_2$R$^8$, —C(═O)NR$^8$R$^8$, and halide;

wherein $R^8$ is selected from the group consisting of: H, —($C_{1-9}$ alkyl), and —($C_{2-9}$ alkenyl); and $R^{11}$ is halide.

In some embodiments, the semi-permanent colorant is a combination of two or more of: genipin, a genipin derivative, lawsone, and a lawsone derivative. In some embodiments, the semi-permanent colorant comprises a combination of two or more genipin derivatives. In some embodiments, the semi-permanent colorant comprises a combination of two or more compounds as delineated in Table 1. In some embodiments, the semi-permanent colorant comprises a combination of Compound 1 and Compound 12. In some embodiments, the ratio of Compound 1 to Compound 12 is about 4:1 to about 1:4 Compound 1:Compound 12. In some embodiments, the semi-permanent colorant is a combination of genipin and Compound 1. In some embodiments, the ratio of genipin to Compound 1 is about 4:1 to about 1:4 genipin:Compound 1. In some embodiments, the ratio of genipin to Compound 1 is about 1:1 genipin:Compound 1. In some embodiments, the semi-permanent colorant is a combination of Compound 1 and Compound 14. In some embodiments, the ratio of Compound 1 to Compound 14 is about 4:1 to about 1:4 Compound 1:Compound 14. In some embodiments, the ratio of Compound 1 to Compound 14 is about 1:1 Compound 1:Compound 14. In some embodiments, the semi-permanent colorant is a combination of genipin and Compound 14. In some embodiments, the ratio of genipin to Compound 14 is about 4:1 to about 1:4 genipin:Compound 14. In some embodiments, the ratio of genipin to Compound 14 is about 1:1 genipin:Compound 14. In some embodiments, the semi-permanent colorant is a combination of genipin, Compound 1, and Compound 14. In some embodiments, the ratio of genipin to Compound 1 to Compound 14 is about 4:1:1 to about 1:1:4 genipin:Compound 1:Compound 14. In some embodiments, in the ratio of genipin to Compound 1 to Compound 14 is about 1:1:1 genipin: Compound 1:Compound 14.

In some embodiments, the semi-permanent colorant is present in an amount of about 5% to about 15% w/w of the composition. In some embodiments, the semi-permanent colorant is present in an amount of about 9% to about 11% w/w of the composition. In some embodiments, the semi-permanent colorant is present in an amount of about 10% w/w of the composition. In some embodiments, the solvent is present in an amount of about 65% to about 85% w/w of the composition. In some embodiments, the solvent is present in an amount of about 75% to about 80% w/w of the composition. In some embodiments, the solvent is present in an amount of about 77% w/w of the composition.

In some embodiments, the solvent comprises water, methanol, ethanol, isopropanol, diethylene glycol monoethyl ether, or a combination thereof. In some embodiments, the solvent is a combination of water and ethanol. In some embodiments, the water is present in an amount of about 25% to about 35% w/w of the composition. In some embodiments, the water is present in an amount of about 30% w/w of the composition. In some embodiments, the ethanol is present in an amount of about 40% to about 55% w/w of the composition. In some embodiments, the ethanol is present in an amount of about 45% to about 50% w/w of the composition. In some embodiments, the ethanol is present in an amount of about 48% w/w of the composition. In some embodiments, the film-forming agent is present in an amount of about 5% to about 10% w/w of the composition. In some embodiments, the film-forming agent is present in an amount of about 6% to about 9% w/w of the composition. In some embodiments, the film-forming agent is present in an amount of about 7.5% w/w of the composition.

In some embodiments, the film-forming agent comprises a volatile silicon resin, polyvinylpyrrolidone, an acrylate, an acrylamide, a copolymer, an isododecane resin, or a combination thereof.

In some embodiments, the film-forming agent comprises polymethylsilsesquioxane, trimethylsiloxysilicate, polypropylsilsesquioxane, dimethicone, cyclopentasiloxane, dimethiconol crosspolymer, polysilicone-6, polysilicone-8, polysilicone-11, polysilicone-14, acrylates copolymer, styrene/acrylates copolymer, polyvinylpyrrolidone, acrylates/C12-22 alkyl methacrylate copolymer, acrylates/polytrimethylsiloxymethacrylate copolymer, polyvinylpyrrolidone/vinyl acetate (VP/VA) copolymer, VP/dimethiconylacrylate/polycarbamyl/polyglycol ester, VP/dimethylaminoethylmethacrylate copolymer, VP/dimethylamino ethylmethacrylate/polycarbamyl polyglycol ester, VP/eicosene copolymer, VP/hexadecene copolymer, VP/methacrylamide/vinyl imidazole copolymer, VP/polycarbamyl polyglycol ester, VP/VA copolymer, polyester-1, polyester-2, polyester-3, polyester-4, polyester-5, polyester-7, polyester-8, and polyester-10, or a combination thereof.

In some embodiments, the film-forming agent is a combination of acrylates copolymer, polyvinylpyrrolidone, and styrene/acrylates copolymer. In some embodiments, the acrylates copolymer is present in an amount of about 0.1% to about 10% w/w of the composition. In some embodiments, the acrylates copolymer is present in an amount of about 0.1% to about 1% w/w of the composition. In some embodiments, the acrylates copolymer is present in an amount of about 0.25% w/w of the composition. In some embodiments, the polyvinylpyrrolidone is present in an amount of about 0.1% to about 10% w/w of the composition. In some embodiments, the polyvinylpyrrolidone is present in an amount of about 0.5% to about 1.5% w/w of the composition. In some embodiments, the polyvinylpyrrolidone is present in an amount of about 1% w/w of the composition. In some embodiments, the styrene/acrylates copolymer is present in an amount of about 0.1% to about 10% w/w of the composition. In some embodiments, the styrene/acrylates copolymer is present in an amount of about 5% to about 7% w/w of the composition. In some embodiments, the styrene/acrylates copolymer is present in an amount of about 6% w/w of the composition.

In some embodiments, the composition further comprises a humectant. In some embodiments, the humectant is present in an amount of about 0.1% to about 10% w/w of the composition. In some embodiments, the humectant is present in an amount of about 0.5% to about 1.5% w/w of the composition. In some embodiments, the humectant is present in an amount of about 1% w/w of the composition.

In some embodiments, the humectant comprises Aloe vera gel, lithium chloride, allantoin, urea, dicyanamideglycerol, lactic acid, propylene glycol, polyethylene glycol, dipropylene glycol, polypropylene glycol, polyethylene glycol, propanediol, hexylene glycol, 1,3-butylene glycol, 1,2,6-hexanetriol, ethoxylated glycerol, propoxylated glycerol, glyceryl triacetate, sorbitol, hydroxypropyl sorbitol, xylitol, maltitol, hyaluronic acid, Tremella extract, sodium lactate, sodium L-pyroglutamate urea, and pyrrolidone carboxylic acid, or a combination thereof. In some embodiments, the humectant is propanediole. In some embodiments, the composition further comprises a preservative.

In some embodiments, the preservative is present in an amount of about 0.1% to about 5% w/w of the composition. In some embodiments, the preservative is present in an amount of about 0.5% to about 1.5% w/w of the composition. In some embodiments, the preservative is present in an amount of about 1% w/w of the composition.

In some embodiments, the preservative comprises ascorbic acid, an ascorbate, a palmitate, citric acid, a benzoate, a benzoic acid, a propionate, propionic acid, a sorbate, sorbic acid, a salicylic acid, a salicylate, hexa-2,4-dienoic acid, a hexa-2,4-dienoate, formaldehyde, a formaldehyde releaser, formic acid and its salts, 3-acetyl-6-methylpyran-2,4-(3H)-dione and its salts, 3,3'-dibromo-4,4'-hexamethylenedioxydibenzamidine and its salts, thiomersal, phenylmercuric salts, undec-10-enoic acid and its salts, 1,3-bis(2-ethylhexyl) hexahydro-5-methyl-5-pyrimidine, 5-bromo-5-nitro-1,3-dioxane, bronopol, 2,4-dichlorobenzyl alcohol, 1-(4-chlorophenyl)-3-(3,4-dichlorophenyl) urea, chlorocresol, chloroxylenol, 5-chloro-2-(2,4-dichlorophenoxy) phenol, N,N"-methylenebis[N'-[3-(hydroxymethyl)-2,5-dioxoimidazolidin-4-yl]urea], polyaminopropyl biguanide, methenamine, quaternium-15, climbazole, DMDM hydantoin, benzyl alcohol, 1-Hydroxy-4-methyl-6-(2,4,4-trimethylpentyl)-2-pyridon, piroctone olamine, bromochlorophene, o-cymen-5-ol, chlorophene, chloroacetaminde, methylchloroisothiazolinone, methylisothiazolinone, phenoxyisopropanol, chlorhexidine, chlorhexidine diacetate, chlorhexidine digluconate, chlorhexidine dihydrochloride, dimethyl oxazolidine, behentrimonium chloride, cetri-monium bromide, cetrimonium chloride, laurtrimonium bromide, laurtrimonium chloride, steartrimonium bromide, steartrimonium chloride, diazolidinyl urea, hexamidine, hexamidine diisethionate, hexamidine paraben, glutaral, 7-ethylbicyclooxazolidine, chlorphenesin, sodium hydroxymethylglycinate, silver chloride, benzethonium chloride, benzalkonium chloride, benzalkonium bromide, benzalkonium saccharinate, benzylhemiformal, iodopropynyl butylcarbamate, biphenyl- 2-ol and its salts, pyrithionine zinc, an erythorbate, a nitrite, ethylenediaminetetraacetic acid (EDTA), butylated hydroxyanisole (BHA), butylated hydroxytoluene (BHT), caprylic acid, dilauryl thiodipropionate, erythorbic acid, gum guaiac, methylparaben, a sulfite, a bisulfite, a metabisulfite, propyl gallatepy, propylparaben, stannous chloride, sulfur dioxide, thiodipropionic acid, an isothiazoline, a paraben, phenoxyethanol, ethylhexylglycerin, a glycol, a tocopherol, 1,2-hexanediol, or a combination thereof.

In some embodiments, the preservative comprises a combination of phenoxyethanol and ethylhexylglycerin. In some embodiments, the combination of phenoxyethanol and ethylhexylglycerin is present in the composition at a ratio of about 9:1 phenoxyethanol:ethylhexylglycerin. In some embodiments, the combination of phenoxyethanol and ethylhexylglycerin is present in an amount of about 0.1% to about 2% w/w of the composition. In some embodiments, the combination of phenoxyethanol and ethylhexylglycerin is present in an amount of about 1% w/w of the composition. In some embodiments, the preservative comprises EDTA. In some embodiments, the EDTA is present in an amount of about 0.01% to about 2% w/w of the composition. In some embodiments, the EDTA is present in an amount of about 0.05% w/w of the composition.

Reference to the term "about" has its usual meaning in the context of compositions to allow for reasonable variations in amounts that can achieve the same effect and also refers herein to a value of plus or minus 10% of the provided value. In some embodiments, "about 20" means or includes amounts from 18 to and including 22.

As used herein, a "colorant" refers to a substance that changes the color of reflected or transmitted light as the result of wavelength-selective absorption.

As used herein, a "temporary colorant" refers to a colorant that sits on top of the skin or, if it penetrates the skin, can diffuse out of the skin or can be washed off by, for example, water, soap, and/or isopropanol.

As used herein, "color" refers to wavelengths of electromagnetic radiation visible to the human eye.

"Surface-active agent" or "surfactant" as used herein refers to a substance that tends to reduce the surface tension of a liquid in which it is dissolved.

Where a compound disclosed herein has at least one chiral center, the compounds may accordingly exist as enantiomers. Where the compounds possess two chiral centers, the compounds may additionally exist as diastereomers. It is to be understood that all such isomers and mixtures thereof are encompassed within the scope of the present disclosure.

Unless otherwise required by context, singular terms shall include pluralities and plural terms shall include the singular. As used herein, the singular form "a", "an", and "the" include plural references unless indicated otherwise. In some embodiments, "an" excipient includes one or more excipients.

The details of one or more embodiments of the disclosure are set forth in the accompanying drawings and the description below. Other features, objects, and advantages of the disclosure will be apparent from the description and drawings, and from the claims. Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and embodiments are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1B:
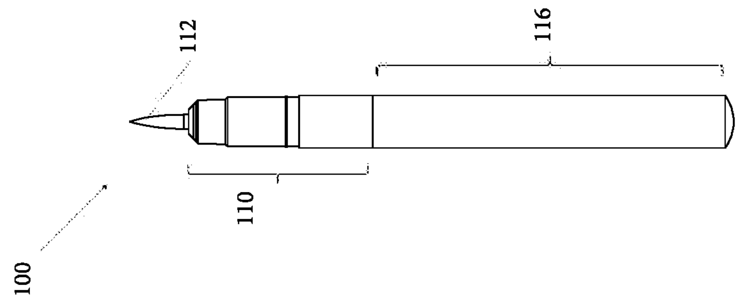
FIG. 1B depicts an embodiment of an ink applicator with an exposed nib.

The manufacturing approach employing ink-jet printing directly onto a skin transfer substrate enables the rapid production of made-to-order custom designed semi-permanent tattoos. However, printing can impose constraints on the creativity of the user applying the tattoo. Freehand application of semi-permanent tattoos can allow a user to practice their skill and/or create one-of-a-kind freehand tattoos on a substrate such as human skin.

Provided herein are ink applicators (e.g., semi-permanent tattoo applicators) that permit the freehand application of tattoo designs onto a substrate. Also provided herein are compositions including such semi-permanent colorants that can be applied to skin as a semi-permanent tattoo. Such compositions can be formulated to be safe for skin contact and sustain stability or skin transferability for the duration of the product shelf life. In some embodiments, the compositions described herein can be suitable for application to skin using a pen-like applicator or a marker-like applicator.

As used herein, a "semi-permanent colorant" or "semi-permanent ink" refers to a colorant that penetrates one or more layers of the skin and is unable to be removed from the skin without physical disruption or natural desquamation of the skin. In some embodiments, a semi-permanent colorant can include a colorant precursor, for example, a molecule, such as genipin, that expresses color upon reaction with one or more other molecules. In some embodiments, a semi-permanent colorant may penetrate the stratum corneum and react with other molecules, e.g., other colorant molecules and/or other molecules present in the stratum corneum, such that the semi-permanent colorant is immobilized within the stratum corneum. In some embodiments, the semi-permanent colorant may cross-link with keratin found in the stratum corneum. In some embodiments, the semi-permanent colorant may react with other molecules, e.g., other colorant molecules and/or other molecules present in the stratum corneum, to form a molecule that is too large to diffuse out of the stratum corneum. In some embodiments, wherein the semi-permanent colorant penetrates the stratum corneum, the colorant residence time is determined by the natural skin desquamation process. In some embodiments, the natural desquamation process can be accelerated by, for example, washing, exfoliation, etc. In some embodiments, the semi-permanent colorant cannot be washed off, for example, by water, soap, and/or isopropanol. In some embodiments, a semi-permanent colorant includes a natural or synthetic pigment or dye. Non-limiting examples of semi-permanent colorants include genipin, a genipin derivative, lawsone, and a lawsone derivative.

As used herein, "genipin" refers to genipin extract, partially purified genipin extract, and/or purified genipin, as described further herein. Genipin is derived from an iridoid glycoside called geniposide, which is present in nearly 40 plant species.

Additionally, genipin is a precursor to gardenia blue that undergoes a transformative reaction upon exposure to amine groups to form a blue colorant (see, for example, Touyama et al., Chem. Pharm. Bull. 42:668-673, 1994; and Touyama et al., Chem. Pharm. Bull. 42(8):1571-1578, 1994; both of which are incorporated by reference herein in their entireties). When placed in contact with skin, genipin can react with the amines in skin to generate the polymer-based and/or oligomer-based blue color in situ. In some embodiments, when placed in contact with skin, genipin reacts with primary amine functionalities within molecules in the skin.

A "genipin derivative" is a compound having a genipin core. In some embodiments, a genipin derivative is a compound having the following core structure:

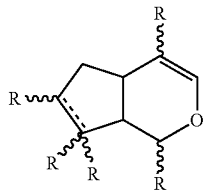

Figure 1A:
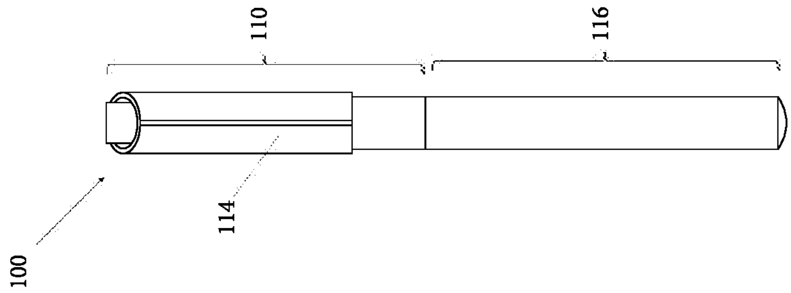
FIG. 1A depicts an embodiment of an ink applicator with a cap covering a nib.

Turning to FIG. 1A and FIG. 1B. FIG. 1A depicts an embodiment of an ink applicator with a cap covering a nib and FIG. 1B depicts an embodiment of an ink applicator with an exposed nib. FIG. 1A includes an ink applicator (e.g., semi-permanent tattoo applicator) 100, upper body 110, lid 114, and lower body 116. Semi-permanent tattoo applicator 100 can be a device that contains an ink composition (e.g., semi-permanent ink) and is designed to be operated by hand to deposit an ink composition to a user's skin. In some embodiments, the semi-permanent tattoo applicator 100 can be a pen or a marker. The terms "pen" or "marker" may be used herein interchangeably to describe the semi-permanent tattoo applicator 100.

In some embodiments, semi-permanent tattoo applicator 100 can be a pen. In some embodiments, the semi-permanent tattoo applicator 100 may be classified as a pen based on the desired effect of the semi-permanent tattoo applicator 100 on a user's skin. In some embodiments, the semi-permanent tattoo applicator 100 may be a pen when the desired effect is to deposit an ink composition to a user's skin with fine detail, achieve a stylistic technique (e.g., pointillism), or in the form of text such as numbers, letters, and/or other characters. In other embodiments, the semi-permanent tattoo applicator 100 can be referred to herein as a marker when the desired effect is to deposit ink to a user's skin with thicker lines.

The ink composition can be any of the ink compositions described herein. In some embodiments, the ink composition can be a semi-permanent ink formulated to adhere to a user's skin. In some embodiments, described herein is an ink composition comprising: a semi-permanent colorant, wherein the semi-permanent colorant comprises a genipin derivative, lawsone, a lawsone derivative, or combinations thereof; a solvent; and a semi-volatile semi-permanent colorant solubilizer. Also provided herein are compositions comprising: a semi-permanent colorant (e.g., semi-permanent ink), wherein the semi-permanent colorant comprises a genipin derivative, lawsone, a lawsone derivative, or combinations thereof; a solvent; and a thickening agent. The ink compositions are described in greater detail herein.

Lower body 116 can include external threading, a reservoir container, and a reservoir. In some embodiments, the external threading can couple the lower body 116 to the upper body 110. The upper body 110, lower body 116 and assembly are described in greater detail in connection with FIGS. 2, 3, and 4. The length of the lower body 116 can be about 60 mm to about 110 mm. In some embodiments, the length of the lower body 116 can be about 60 mm to about 110 mm, about 65 mm to about 110 mm, about 70 mm to about 110 mm, about 75 mm to about 110 mm, about 80 mm to about 110 mm, about 85 mm to about 110 mm, about 90 mm to about 110 mm, about 95 mm to about 110 mm, about 100 mm to about 110 mm, or about 105 mm to about 110 mm. In some embodiments, the lower body 116 is about 89 mm. Additional detail of the lower body 116 is described in connection with FIG. 2.

Upper body 110 can include a nib and internal threading. In some embodiments, the internal threading can couple the upper body 110 to the lower body 116. The upper body 110, lower body 116 and assembly are described in greater detail in connection with FIGS. 2, 3, and 4. The length of the upper body 110 (not including the nib) can be about 20 mm to about 50 mm. In some embodiments, the length of the upper body 110 can be about 20 mm to about 50 mm, about 25 mm to about 50 mm, about 30 mm to about 50 mm, about 35 mm to about 50 mm, about 40 mm to about 50 mm, or about 45 mm to about 50 mm. In some embodiments, the upper body 110 is about 38 mm. Additional detail of the upper body is described in connection with FIG. 3.

FIG. 1A includes a schematic drawing of a lid 114. In some embodiments, the lid 114 connects to the upper body 110 to protect the nib and prevent excess airflow that may dry out the nib. In some embodiments a seal can be provided by a screw mechanism to couple the lid 114 to the upper body 110. In other embodiments, a seal can be provided by a snapping mechanism where the lid 114 snaps over or under a lip of the upper body 110. In some embodiments, the lid 114 connects to the lower body 116 to provide a seal. In some embodiments, a seal can be provided by a screw mechanism to couple the lid 114 to the lower body 116. In other embodiments, a seal can be provided by a snapping mechanism where the lid 114 snaps over or under a lip of the lower body 116. The seal provided by the lid 114 can decrease drying out of the nib 112.

The length of the lid 114 can be about 30 mm to about 70 mm. In some embodiments, the length of the lid 114 is about 30 mm to about 70 mm, about 35 mm to about 70 mm, about 40 mm to about 70 mm, about 45 mm to about 70 mm, about 50 mm to about 70 mm, about 55 mm to about 70 mm, about 60 mm to about 70 mm, or about 65 mm to about 70 mm. In some embodiments, the length of the lid is about 50 mm. The lid 114 can have a diameter of about 8 mm to about 14 mm. In some embodiments, the lid 114 can have a diameter of about 8 mm to about 14 mm, about 9 mm to about 14 mm, about 10 mm to about 14 mm, about 11 mm to about 14 mm, about 12 mm to about 14 mm, or about 13 mm to about 14 mm.

Turning now to FIG. 1B. FIG. 1B includes ink applicator (e.g., semi-permanent tattoo applicator) 100, a nib 112, an upper body 110, and a lower body 116. In an embodiment, semi-permanent tattoo applicator 100 includes features that are analogous to the features described in connection with FIG. 1A. FIG. 1B includes a nib 112 and does not include a lid 114 described in connection with FIG. 1A. The nib 112 can include various shapes, sizes, and materials. Nibs such as nib 112 can be replaceable such that a user can remove an initial nib (e.g., nib 112) and replace with a subsequent nib. Nibs can be of various shapes and sizes to allow for varying aesthetics and techniques. Details of various nibs 112 are described in connection with FIGS. 6, 7, 8, 9 and/or 10.

A nib 112 is configured to deposit an ink composition (e.g., a semi-permanent ink composition) to a substrate. In some embodiments, a substrate can include paper or animal skin (e.g., human skin). The ink composition is contained in a reservoir within the lower body 116. The nib 112 includes a first end that is external to the upper body 110 as shown by nib 112 of FIG. 1B. The nib 112 includes a second end (obscured by FIG. 1B) which contacts the ink composition within the reservoir. In some embodiments, the second end of the nib 112 extends a distance into the reservoir to contact the ink composition (detailed in connection with FIG. 4). In other embodiments, the second end of the nib 112 contacts the ink composition indirectly via a transfer nib, where the transfer nib contacts the ink composition and facilitates the movement of the ink composition to the nib 112 (described in greater detail in connection with FIG. 5). The nib 112 can be made from a variety of materials. In some embodiments, the nib can be made of polyester fiber, acrylic fiber, nylon brush fibers, and sintered polyethylene.

As mentioned herein, nibs (e.g., nib 112) can be of various shapes and sizes. Nibs can be about 10 mm to about 50 mm. In some embodiments, nibs (e.g., nib 112) can be about 10 mm to about 50 mm, about 15 mm to about 50 mm, about 20 mm to about 50 mm, about 25 mm to about 50 mm, about 30 mm to about 50 mm, about 35 mm to about 50 mm, about 40 mm to about 50 mm, or about 45 mm to about 50 mm. In some embodiments, nib 112 is about 15 mm. In some embodiments, nib 112 is about 20 mm. In some embodiments, nib 112 is about 30 mm. In some embodiments, nib 112 is about 40 mm.

In some embodiments, the weight of the semi-permanent tattoo applicator 100 without an ink composition is about 5 grams to about 15 grams. In some embodiments, the semi-permanent tattoo applicator 100 has a weight of about 5 grams, 6 grams, 7 grams, 8 grams, 9 grams, 10 grams, 11 grams, 12 grams, 13 grams, 14 grams, or 15 grams.

Figure 2:
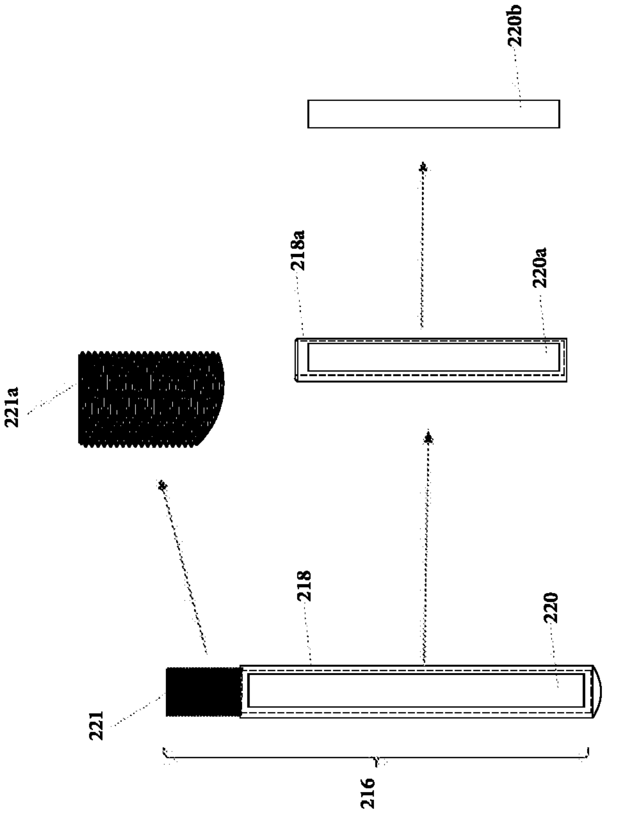
FIG. 2 is an exploded view of a lower body of an embodiment of an ink applicator.

Turning now to FIG. 2. FIG. 2 is an exploded view of a lower body of an embodiment of an ink applicator. FIG. 2 includes a lower body 216, external threading 221 (zoomed view of external threading 221*a*), reservoir container 218 (reservoir container 218*a* is depicted outside of the lower body 216), reservoir 220 contained within the reservoir container 218 (reservoir 220*a* contained within the reservoir container 218*a* outside of the lower body 216; and reservoir 220*b* alone). In the embodiment depicted in FIG. 2, lower body 216 includes one or more features of lower body 116 described above in connection with FIGS. 1A and 1B.

The external threading 221/221*a* can couple to an internal threading of an upper body (e.g., upper body 110 of FIGS. 1A and 1B). The internal threading of the upper body is described further detail in connection with FIG. 3. The external threading 221/221*a* can have a diameter of about 5 mm to about 15 mm. In some embodiments, the external threading 221/221*a* can include a diameter of about 5 mm to about 15 mm, about 7 mm to about 15 mm, about 9 mm to about 15 mm, or about 11 mm to about 15 mm. In some embodiments, the diameter of the external threading 221/221*a* is about 10 mm. In some embodiments, the diameter of the external threading is about 11 mm.

The reservoir container 218 can contain the reservoir 220 inside the lower body 216. Reservoir container 218*a* is the reservoir container 218 outside of the lower body 216. In some embodiments, the reservoir container 218 is selectively removable. For example, a user can selectively remove the reservoir container 218 from the lower body 216 to facilitate the replacement or refilling of the reservoir 220 with an ink composition (e.g., semi-permanent ink composition). The reservoir container 218/218*a* can be about 40 mm to about 120 mm in length. In some embodiments, the reservoir container 218/218*a* is about 40 mm to about 120 mm, about 45 mm to about 120 mm, about 50 mm to about 120 mm, about 55 mm to about 120 mm, about 60 mm to about 120 mm, about 65 mm to about 120 mm, about 70 mm to about 120 mm, about 75 mm to about 120 mm, about 80 mm to about 120 mm, about 85 mm to about 120 mm, about 90 mm to about 120 mm, about 95 mm to about 120 mm, about 100 mm to about 120 mm, about 105 mm to about 120 mm, about 110 mm to about 120 mm, or about 115 mm to about 120 mm.

The reservoir container 218/218*a* can include a diameter of 5 mm to about 12 mm. In some embodiments, the diameter of the reservoir container 218/218*a* is about 5 mm to about 12 mm, about 6 mm to about 12 mm, about 7 mm to about 12 mm, about 8 mm to about 12 mm, about 9 mm to about 12 mm, about 10 mm to about 12 mm, or about 11 mm to about 12 mm. In some embodiments, the reservoir container 218 is about 8 mm in diameter.

The reservoir 220 is configured to contain any of the ink compositions described herein (e.g., semi-permanent ink composition). The reservoir 220 is contained within the reservoir container 218 within the lower body 216. Numeral 220*a* depicts the reservoir 220 within the reservoir container 218 but outside of the lower body 216. Numeral 220*b* depicts the reservoir 220/220*a* outside of the reservoir container 218 and the lower body 216.

In some embodiments, the reservoir 220 is selectively removable. In some embodiments, the reservoir 220 can be removed from the reservoir container 218. In some embodiments, the reservoir 220 can be replaced. In some embodiments, the reservoir 220 can be refilled with any of the ink compositions described herein. In some embodiments, the reservoir 220 can contain any of the ink compositions described herein. When the reservoir 220 is empty and/or low on ink, a user can remove the reservoir 220 from the lower body 216 and replace with another reservoir. In some embodiments, the reservoir 220 may not be empty but a user may wish to exchange an initial reservoir with a different reservoir of, for example, a different color. Exchanging a reservoir to a different color can in some embodiments, prompt a nib to be exchanged as well.

In some embodiments, a reservoir 220 of a particular color can correspond to one or more nib. In some embodiments, a reservoir 220 having a first color can correspond to one or more nibs such that when a change of color is desired by a user, the reservoir 220 having the first color is exchanged together with its corresponding nib and replaced with a different reservoir having a second color and corresponding to its respective one or more nibs.

In some embodiments, the lower body 216 can correspond to one or more nibs. In some embodiments, a lower body 216 having a first color can correspond to one or more nibs such that when a change of color is desired by a user, the lower body 216 having the first color is exchanged together with its corresponding nib and replaced with a different lower body having a second color and corresponding to its respective one or more nibs.

In some embodiments, the reservoir 220 can be refilled with any of the ink compositions described herein. In some embodiments, replacement ink compositions can be contained in a pouch with a spout or dropper and the ink composition can be dispensed via the pouch or dropper into the empty reservoir 220. The refilled reservoir 220 can be positioned back into the reservoir container 218 for operation.

In some embodiments, the lower body 216 can include a window. In some embodiments, the lower body 216 can include a window that is transparent such that the contents of a reservoir 220 can be viewed. For example, a window included in the lower body 216 can be operated by a user of the ink applicator to determine attributes of the ink within the reservoir 220. In some embodiments, the window can be used to determine an approximate amount of ink composition that is in the reservoir 220. In some embodiments, the window can be used to determine a color of ink composition that is included in the reservoir 220.

In some embodiments, in addition to a window or instead of a window, the lower body 216 can include graduations. In some embodiments, the lower body 216 is made from a material that is opaque or translucent such that a level or color of ink is visible without a window. In such embodiments, the lower body 216 can include graduations to provide the user with information regarding a level of remaining ink and/or a color of the ink. In some embodiments, the lower body 216 can include graduations on a window that is transparent such that the contents of a reservoir 220 can be viewed and amounts can be estimated. For example, a window with graduations included in the lower body 216 can be operated by a user of the ink applicator to determine attributes of the ink within the reservoir 220. In some embodiments, the window with graduations can be used to determine an approximate amount of ink composition that is in the reservoir 220. In some embodiments, the ink composition within the reservoir is liquid, and a level of the liquid ink composition can be viewed via a window with graduations.

The reservoir 220 and/or the reservoir container 218 can include an aperture to receive a nib or a transfer nib. In some embodiments, the reservoir 220 and/or the reservoir container 218 can include an aperture that permits a portion of a nib or a transfer nib to protrude into the reservoir 220 and/or the reservoir container 218 such that the nib or transfer nib can contact the ink composition. The ink composition from the reservoir 220 can flow from the reservoir 220 to the nib via capillary action such that the ink composition can exit the semi-permanent tattoo applicator and be deposited on a substrate (e.g., skin).

The reservoir container 218 can be substantially hollow such that the interior portion of the reservoir container 218 is a substantially empty void. Refilling the reservoir container 218 can include depositing a liquid ink composition and fill the void of the reservoir container 218. In such embodiments, the void can optionally include an agitator to prevent settling of the ink composition within the reservoir container 218. Such embodiments, are described in further detail in connection with FIG. 5.

The reservoir 220 can be substantially hollow such that the interior portion of the reservoir 220 is a substantially empty void. Refilling the reservoir 220 can include depositing a liquid ink composition and fill the void of the reservoir 220. In such embodiments, the void can optionally include an agitator to prevent settling of the ink composition within the reservoir 220. Such embodiments, are described in further detail in connection with FIG. 5. In some embodiments, the reservoir 220 contains a fibrous material that is saturated with any of the ink compositions described herein. In some embodiments, the fibrous material of reservoir 220 is a polyester material (e.g., polyethylene terephthalate, polyester, and/or polypropylene). In some embodiments, the fibrous material is polyethylene terephthalate.

The reservoir 220 can be about 30 mm to about 120 mm in length. In some embodiments, the reservoir 220 is about 30 mm to about 120 mm, about 35 mm to about 120 mm, about 40 mm to about 120 mm, about 45 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, about 50 mm to about 120 mm, or about 50 mm to about 120 mm.

In some embodiments, the diameter of the reservoir 220 is about 5 mm to about 12 mm. In some embodiments, the diameter of the reservoir 220 is about 5 mm to about 12 mm, about 6 mm to about 12 mm, about 7 mm to about 12 mm, about 8 mm to about 12 mm, about 9 mm to about 12 mm, about 10 mm to about 12 mm, or about 11 mm to about 12 mm. IN some embodiments, the diameter is the reservoir container is about 7 mm. A skilled practitioner would understand that the reservoir 220 inserts into the reservoir container 218 thus the diameter of the reservoir 220 is not the same as the diameter of the reservoir container 218.

Figure 3:
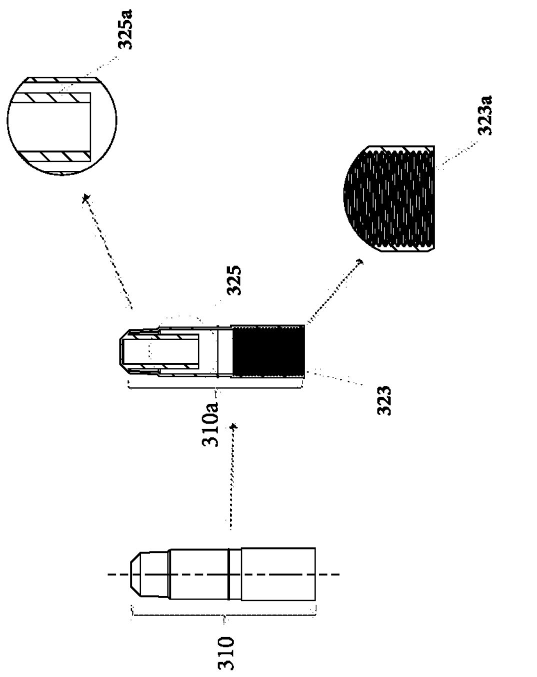
FIG. 3 is an exploded view of an upper body of an embodiment of an ink applicator.

Turning now to FIG. 3. FIG. 3 is an exploded view of an upper body of an embodiment of an ink applicator. FIG. 3 includes a upper body 310, internal threading 323 (zoomed view of internal threading 323*a*), and lip 325 (zoomed in view of lip 325). In the embodiment depicted in FIG. 3, upper body 310 includes one or more features of upper body 110 described above in connection with FIGS. 1A and 1B.

The internal threading 323/323*a* can couple to an external threading of a lower body (e.g., external threading 221 of lower body 216 of FIG. 2). The internal threading 323/323*a* can have a diameter of about 5 mm to about 15 mm. In some embodiments, internal threading 323/323*a* can include a diameter of about 5 mm to about 15 mm, about 7 mm to about 15 mm, about 9 mm to about 15 mm, or about 11 mm to about 15 mm. In some embodiments, the diameter of the internal threading 323/323*a* is about 10 mm. In some embodiment, the diameter of the external threading is about 11 mm.

As mentioned herein, the internal threading 323/323*a* can couple to an external threading of a lower body (e.g., external threading 221 of lower body 216 of FIG. 2). When the upper body 310 and lower body 216 of FIG. 2 are coupled together via the internal threading 323/323*a* and external threading 221 of FIG. 2 a lip 325/325*a* can contact the reservoir container and/or reservoir (e.g., reservoir container 218 and/or reservoir 220 of FIG. 2) and create a seal. In such embodiments, a nib (e.g., the nib 112 of FIG. 1) can be inserted in the upper body 310 and the lip 325/325*a* can provide a passage to the reservoir container 218 and/or reservoir 220 of FIG. 2.

Figure 4:
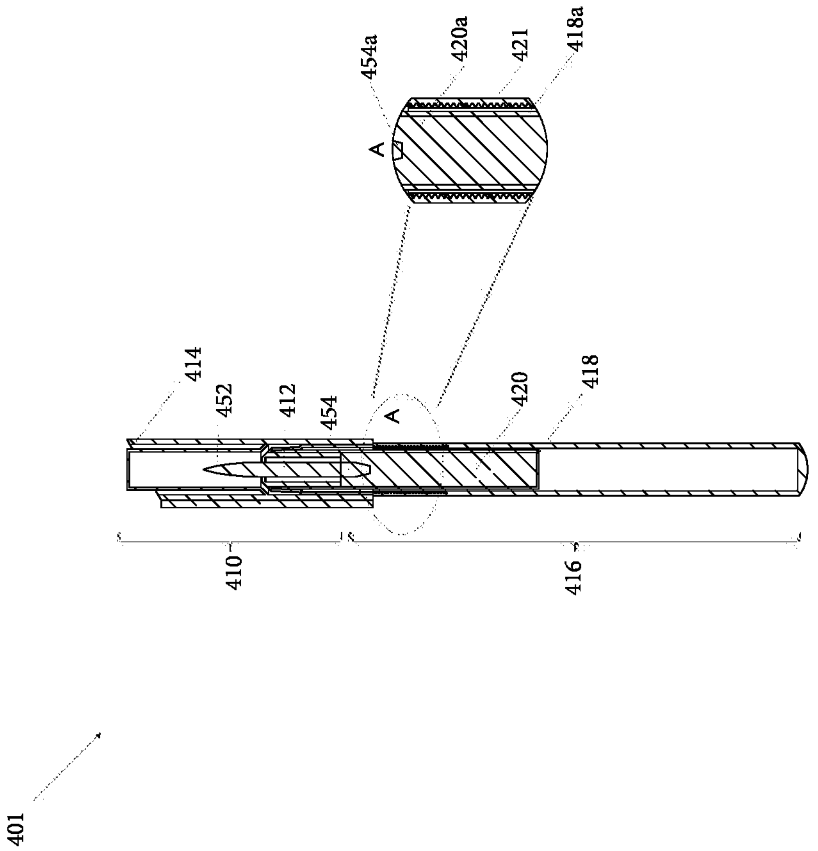
FIG. 4 depicts a cross-section view of an embodiment of an ink applicator.

Turning now to FIG. 4. FIG. 4 depicts a cross-section view of an embodiment of an ink applicator (e.g., semi-permanent tattoo applicator) 401. Semi-permanent tattoo applicator 401 includes an upper body 410 and a lower body 416, a cap 414, a nib 412, a reservoir 420 contained in a reservoir container 418. Detail A is identified by an oval of broken line and is illustrated as zoomed in portion A that identifies a second end 454*a* of nib 412, reservoir 420*a*, reservoir container 418*a*, and threading 421. In the embodiment depicted in FIG. 4, semi-permanent tattoo applicator 401 includes one or more features described above in connection with FIGS. 1A, 1B, 2, and 3.

Nib 412 includes a first end 452 and a second end 454. The first end 452 extends external to the upper body 410 and the second end 454 extends into the lower body 416 and into the reservoir 420 and/or the reservoir container 418 such that it can contact an ink composition. Detail A depicts second end 454*a* of nib 412 extending into the reservoir 420*a* which is contained in the reservoir container 418*a*. Threading 421 is a depiction of external threading (e.g., external threading 221 of FIG. 2) mated to internal threading (e.g., internal threading 323 of FIG. 3). Threading 421 illustrates the upper body 410 coupled to the lower body 416. In some embodiments, the threading 421 is unscrewed such that upper body 410 separates from the lower body 416. Decoupling the upper body 410 and the lower body 416 can permit a user to replace and/or refill a reservoir 420.

In some embodiments, upper body 410 can decouple from the lower body 416 via the threading 421 to expose the reservoir container 418 and reservoir 420. A user could, for example, remove an initial reservoir 420 and replace with a subsequent reservoir. After reservoir 420 replacement, the user could then re-couple the upper body 410 to the lower body 416 and resume operation of the semi-permanent tattoo applicator 401 where the second end 454*a* of the nib 412 is inserted into the newly replaced reservoir 420 and/or reservoir container 418.

In some embodiments, a reservoir 420 and/or the reservoir container 418 can be refilled with any of the ink compositions described herein. In some embodiments, upper body 410 can decouple from the lower body 416 via the threading 421 to expose the reservoir container 418 and reservoir 420. A user could, for example, remove reservoir 420 and refill it with liquid ink. After reservoir 420 is refilled, the user could then re-couple the upper body 410 to the lower body 416 and resume operation of the semi-permanent tattoo applicator 401 where the second end 454*a* of the nib 412 is inserted into the newly refilled reservoir 420.

In another embodiment, a user could remove reservoir container 418 and fill or refill it with liquid ink. After reservoir container 418 is filled or refilled, the user could then re-couple the upper body 410 to the lower body 416 and resume operation of the semi-permanent tattoo applicator 401 where the second end 454*a* of the nib 412 is inserted into the newly filled or refilled reservoir container 418.

The nib 412 can be replaced with a new or different nib. In some embodiments, upper body 410 can decouple from the lower body 416 via the threading 421 to expose the reservoir container 418 and the second end 454 of the nib 412. In some embodiments, a nib 412 is replaced by pulling on the nib 412 to remove it from the upper body 410. In some embodiments, a nib 412 can be removed from the upper body 410 using an instrument (e.g., forceps, tongs, or tweezers).

Figure 5:
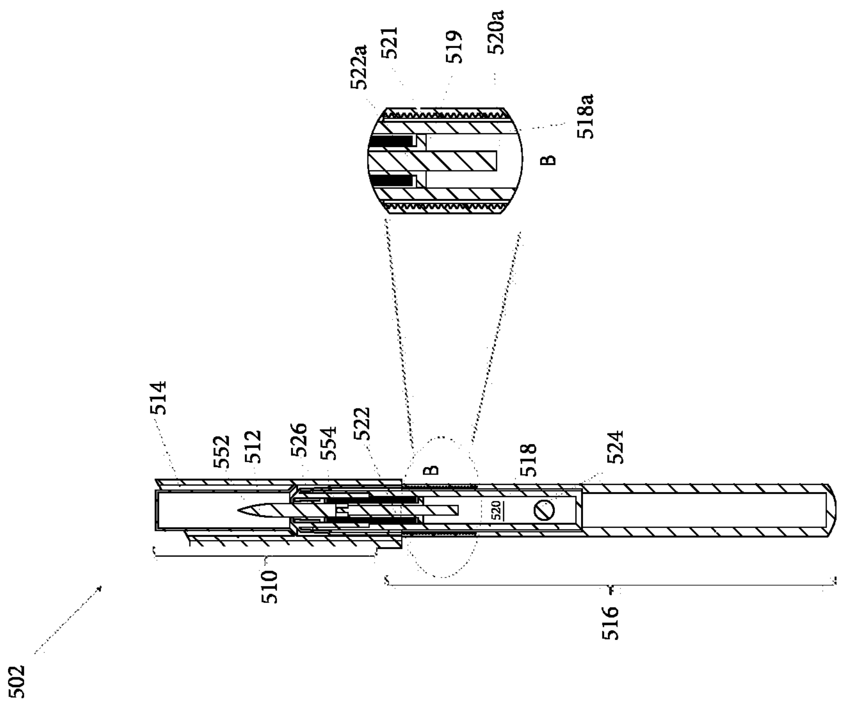
FIG. 5 depicts a cross-section view of an embodiment of an ink applicator that includes a transfer nib and an agitator.

Turning now to FIG. 5. FIG. 5 depicts a cross-section view of an embodiment of an ink applicator (e.g., semi-permanent tattoo applicator) 502. Semi-permanent tattoo applicator 502 includes an upper body 510 and a lower body 516, a cap 514, a nib 512, a transfer nib 522, a transfer casing 526, a reservoir 520, and an agitator 524. The ink applicator 502 optionally includes a reservoir 520 and/or reservoir container 518. In some embodiments, the reservoir 520 is optionally contained in a reservoir container 518. Detail B is identified by an oval of broken line and can be seen with zoomed in portion B that identifies a portion of the transfer nib 522*a* that is in reservoir 520*a*, reservoir container 518*a*, ridge 519, and threading 521. Embodiments, describing a reservoir 520 without a reservoir container 518 can be held in place within the lower body 516 with the ridge 519. The ridge 519 can prevent the reservoir 520*a* from moving substantially such that the transfer nib 522*a* can transfer ink composition from the reservoir 520*a* to the nib 512. In the embodiment depicted in FIG. 5, semi-permanent tattoo applicator 502 includes one or more features described above in connection with FIGS. 1A, 1B, 2, 3, and 4.

Agitator 524 can be configured to move in the reservoir 520, the reservoir container 518, or the space in the lower body 516 that is optionally occupied by the reservoir 520 or reservoir container 518. Agitator 524 can mix liquid ink composition and prevent settling of components of the liquid ink composition. For example, a user can shake the semi-permanent tattoo applicator 502 prior to using the ink applicator 502 and the agitator 524 can move within the reservoir 520, the reservoir container 518, or the space in the lower body 516 that is optionally occupied by the reservoir 520 or reservoir container 518 and mix the liquid ink. In some embodiments, the agitator is metallic. In some embodiments, the agitator 524 is a metal ball. In some embodiments, the reservoir 520 or reservoir container 518 contains a single agitator 524. In some embodiments, the reservoir 520 can include multiple agitators 524.

The transfer nib 522 operates to move an ink composition (e.g., any of the ink compositions described herein from the reservoir 520, the reservoir container 518, or the space in the lower body 516 that is optionally occupied by the reservoir 520 or reservoir container 518. In some embodiments, an ink composition can be included in a reservoir 520 that is contained in a reservoir container 518 within the lower body 516. In some embodiments, the transfer nib 522 contacts the ink composition within the reservoir 520 and delivers the ink composition to the nib 512. In some embodiments, the reservoir 520 include liquid ink composition and the transfer nib 522 absorbs the liquid ink composition to transfer to the nib 512. In some embodiments, the reservoir 520 includes a fiber (e.g., polyester fiber, acrylic fiber, nylon brush fibers, and sintered polyethylene) that includes an ink composition. A user can apply the first end 552 of the nib 512 to a substrate (e.g., skin). A user can replace or refill the reservoir 520 when empty. In some embodiments, a reservoir 520 can be refilled by removing the reservoir 520 from the reservoir container 518 and adding ink to the reservoir 520. In some embodiments, a reservoir 520 can be replaced by removing the reservoir 520 from the reservoir container 518, discarding, and inserting a different (e.g., new) reservoir 520 into the reservoir container 518.

In some embodiments, an ink composition can be included in a reservoir 520 that is contained within the lower body 516 (e.g., without a reservoir container 518). As shown in detail B, ridge 519 can secure the reservoir 520*a* in place such that transfer nib 522*a* contacts the ink composition contained in the reservoir 520*a*. In some embodiments, the transfer nib 522 contacts the ink composition within the reservoir 520 and delivers the ink composition to the nib 512 (e.g., the second end 554 of the nib 512). In some embodiments, the reservoir 520 includes a liquid ink composition and the transfer nib 522 absorbs the liquid ink composition to transfer to the nib 512. In some embodiments, the reservoir includes a fiber (e.g., polyester fiber, acrylic fiber, nylon brush fibers, and sintered polyethylene) that includes an ink composition. A user can apply the first end 552 of the nib 512 to a substrate (e.g., skin) to deposit the ink composition. A user can apply the first end 552 of the nib 512 to a substrate (e.g., skin). A user can replace or refill the reservoir 520 when empty. In some embodiments, a reservoir 520 can be refilled by removing the reservoir 520 from the lower body 516 and adding ink to the reservoir 520. In some embodiments, a reservoir 520 can be replaced by removing the reservoir 520 from the lower body 516, discarding, and inserting a different (e.g., new) reservoir 520 into the lower body 516.

In some embodiments, an ink composition can be included in a reservoir container 518 that is contained within the lower body 516 (e.g., without a reservoir 520). In some embodiments, the transfer nib 522 contacts the ink composition within the reservoir container 518 and delivers the ink composition to the nib 512 (e.g., the second end 554 of the nib 512). A user can apply the first end 552 of the nib 512 to a substrate (e.g., skin) to deposit the ink composition. A user can replace or refill the reservoir container 518 when empty of ink composition. In some embodiments, a reservoir container 518 can be refilled by removing the reservoir container 518 from the lower body 516 and adding ink to the reservoir container 518. In some embodiments, a reservoir container 518 can be replaced by removing the reservoir container 518 from the lower body 516, discarding, and inserting a different (e.g., new) reservoir container 518 into the lower body 516.

In some embodiments, an ink composition can be included in the lower body 516 (e.g., the space in the lower body 516 that is optionally occupied by the reservoir 520 or reservoir container 518). In some embodiments, the transfer nib 522 contacts the ink composition within the lower body 516 and delivers the ink composition to the nib 512 (e.g., the second end 554 of the nib 512). A user can apply the first end 552 of the nib 512 to a substrate (e.g., skin) to deposit the ink composition. A user can replace or refill the lower body 516 (e.g., the space in the lower body 516 that is optionally occupied by the reservoir 520 or reservoir container 518) when empty of ink composition. In some embodiments, the space in the lower body 516 that is optionally occupied by the reservoir 520 or reservoir container 518 can be refilled by adding ink to the space in the lower body 516 that is optionally occupied by the reservoir 520 or reservoir container 518. In some embodiments, a lower body 516 can be replaced by decoupling the lower body 516 from the upper body 510, discarding, and inserting a different (e.g., new) lower body 516.

The transfer casing 526 can be configured to connect the transfer nib 522 to the nib 512. In some embodiments, the transfer casing is made of a porous sponge material. In some embodiments, the transfer nib 522 is a slotted cylindrical attachment that serves to retain ink compositions. In some embodiments, the transfer nib 522 is made from a porous material and operates to transfer the ink composition from the reservoir 520 (or the reservoir container 518 or the lower body 516) to the second end 554 of the nib 512. The transfer nib 522 is optional for some nib 512 types. As discussed herein in connection with FIGS. 6-10, some types of nibs are configured for operation with a transfer nib 522.

In some embodiments, the ink applicator 502 includes a reservoir container 518 but does not include a reservoir 520. In such embodiments, any ink composition described herein can be included in the reservoir container 518 and the ink composition can be drawn from the reservoir container 518 to the nib 512 via the transfer nib 522.

In embodiments that do not include a reservoir container 518 or a reservoir 520, a user can add or refill an ink composition by disconnecting the upper body 510 from the lower body 516. In other embodiments that do not include a reservoir container 518 or a reservoir 520, a user can add or refill an ink composition by disconnecting the upper body 510 from an initial lower body 516 and reattach the upper body 510 to a different lower body 516.

Figure 6:
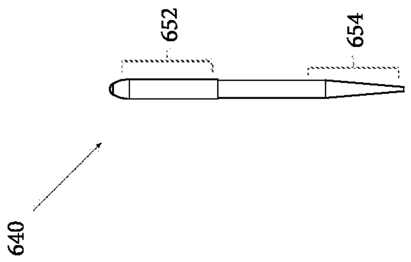
FIG. 6 depicts an embodiment of a nib with a firm round tip.

FIGS. 6-10 depict different types and styles of nibs. Turning now to FIG. 6. FIG. 6 depicts an embodiment of a nib with a firm round tip. Nib 640 includes a first end 652 and a second end 654. In an embodiment, nib 640 includes one or more features of the nibs described in connection with FIGS. 1A, 1B, 2, 3, 4, and 5. The nib 640 includes a firm round tip at the first end 652. In some embodiments, a firm round tip may provide a desired effect of ink application to a substrate such as skin.

For example, a firm round tip may provide aesthetically pleasing detail and outlines for designs. A user can use a firm round tip nib such as nib 640 in conjunction with a semi-permanent tattoo applicator (e.g., ink applicator 100 of FIG. 1) can allow a user the creative freedom to create freehand designs with fine detail. Additionally, a firm round tip such as the first end 652 of nib 640 can provide the precision and/or accuracy for writing text, characters, and script.

The second end 654 of the nib 640 can contact the ink composition. In some embodiments, the second end 654 of the nib 640 can contact the ink composition contained in a reservoir (e.g., reservoir 420*a* of FIG. 4). The nib 640 can have a length of about 20 mm to about 40 mm. In some embodiments, the length of the nib from the first end 652 to the second end 654 is about 20 mm to about 40 mm, about 25 mm to about 40 mm, about 30 mm to about 40 mm, or about 35 mm to about 40 mm. In some embodiments the diameter of the top of the first end 652 is about 0.2 mm to about 1.0 mm. In some embodiments, the diameter of the first end is about 0.2 mm to about 1.0 mm, about 0.4 mm to about 1.0 mm, about 0.6 mm to about 1.0 mm, or about 0.8 mm to about 1.0 mm.

Figure 7:
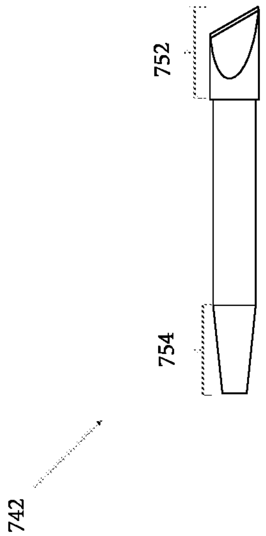
FIG. 7 depicts an embodiment of a nib with a chiseled tip.

Turning now to FIG. 7. FIG. 7 depicts an embodiment of a nib with a chiseled tip. FIG. 7 Nib 742 includes a first end 752 and a second end 754. In an embodiment, nib 742 includes one or more features of the nibs described in connection with FIGS. 1A, 1B, 2, 3, 4, 5, and 6. The nib 742 includes a chiseled tip at the first end 752. In some embodiments, a chiseled tip may provide a desired effect of ink application to a substrate such as skin.

For example, a chiseled tip may provide aesthetically pleasing detail and outlines for designs. Using a chiseled tip nib such as nib 742 in conjunction with a semi-permanent tattoo applicator (e.g., ink applicator 100 of FIG. 1) can allow a user the creative freedom to create freehand designs with fine detail. A chiseled tip such as the first end 752 of nib 742 can provide the precision and/or accuracy for writing text, characters, such as calligraphy and script. A chiseled tip such as the first end 752 of nib 742 can further provide the precision and/or accuracy for filling in larger areas of space with the ink composition. In some embodiments, an ink applicator 100 of FIG. 1 can be fitted with a first nib to draw an outline of a design (e.g., nib 640 of FIG. 6). The first nib 640 can be removed and a second nib 742 can be installed to the ink applicator 100 and a user can fill in the space within the outlined design.

The second end 754 of the nib 742 can contact the ink composition. In some embodiments, the second end 754 of the nib 742 can contact the ink composition contained in a reservoir (e.g., reservoir 420*a* of FIG. 4). The nib 742 can have a length of about 20 mm to about 40 mm. In some embodiments, the length of the nib from the first end 752 to the second end 754 is about 20 mm to about 40 mm, about 25 mm to about 40 mm, about 30 mm to about 40 mm, or about 35 mm to about 40 mm. In some embodiments, the angle of the first end 752 chisel is about 100° to 140°. In some embodiments, the angle of the first end 754 is about 100° to about 140°, about 110° to about 140°, about 120° to about 140°, or about 130° to about 140°.

Figure 8:
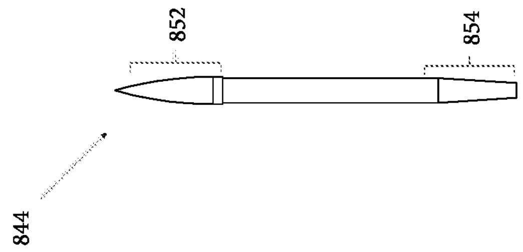
FIG. 8 depicts an embodiment of a nib with a thin tip.

Turning now to FIG. 8. FIG. 8 depicts an embodiment of a nib with a thin tip. Nib 844 includes a first end 852 and a second end 854. In an embodiment, nib 844 includes one or more features of the nibs described in connection with FIGS. 1A, 1B, 2, 3, 4, 5, 6, and 7. The nib 844 includes a fine pointed tip at the first end 852. In some embodiments, a fine pointed tip may provide a desired effect of ink application to a substrate such as skin.

For example, a fine pointed tip may provide aesthetically pleasing detail and outlines for designs. A user can use a fine pointed tip nib such as nib 844 in conjunction with a semi-permanent tattoo applicator (e.g., ink applicator 100 of FIG. 1) can allow a user the creative freedom to create freehand designs with fine detail. Additionally, a fine pointed tip such as the first end 852 of nib 844 can provide the precision and/or accuracy for writing text, characters, and script. In another embodiment, the fine pointed tip such as the first end 852 of nib 844 can provide stylistic and creative details such as a pointillism effect.

The second end 854 of the nib 844 can contact the ink composition. In some embodiments, the second end 854 of the nib 844 can contact the ink composition contained in a reservoir (e.g., reservoir 420*a* of FIG. 4). The nib 844 can have a length of about 20 mm to about 60 mm. In some embodiments, the length of the nib from the first end 852 to the second end 854 is about 20 mm to about 60 mm, about 25 mm to about 60 mm, about 30 mm to about 60 mm, about 35 mm to about 60 mm, about 40 mm to about 60 mm, about 45 mm to about 60 mm, about 50 mm to about 60 mm, or about 55 mm to about 60 mm.

Figure 9:
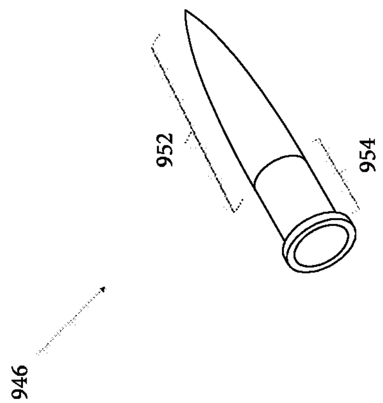
FIG. 9 depicts an embodiment of a nib with a nylon brush tip.

Turning now to FIG. 9. FIG. 9 depicts an embodiment of a nib with a nylon brush tip. In an embodiment, nib 946 includes one or more features of the nibs described in connection with FIGS. 1A, 1B, 2, 3, 4, 5, 6, 7, and 8. The nib 946 includes nylon brush fibers at the first end 952. In some embodiments, nylon brush fibers may provide a desired effect of ink application to a substrate such as skin.

For example, a nylon brush fibers may provide aesthetically pleasing detail and outlines for designs. A user can use nylon brush fiber tip nib such as nib 946 in conjunction with a semi-permanent tattoo applicator (e.g., ink applicator 100 of FIG. 1) can allow a user the creative freedom to create freehand designs with fine detail. Additionally, a nylon brush fiber tip such as the first end 952 of nib 946 can provide the precision and/or accuracy for writing text, characters, and script. In another embodiment, the nylon brush fiber tip such as the first end 952 of nib 946 can provide stylistic and creative details such as a pointillism effect or a water color effect.

The nib 946 includes an opening at the second end 954. In some embodiments, the opening at the second end 954 can be used in conjunction with transfer nib 522 of FIG. 5. The transfer nib 522 of FIG. 5 can absorb the ink composition and deliver the composition to the nylon brush fibers at the first end 952. The nib 946 can have a length from the first end 952 to the second end 954 of about 10 mm to about 25 mm. In some embodiments, the nib 946 can have a length of about 10 mm to about 25 mm, about 15 mm to about 25 mm, or about 20 mm to about 25 mm.

Figure 10:
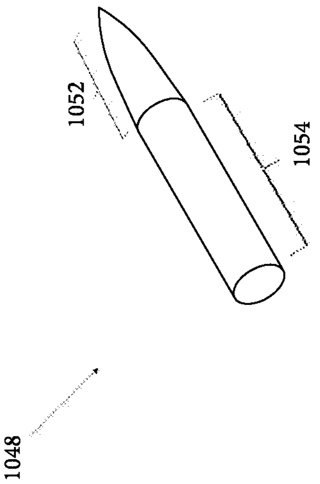
FIG. 10 depicts an embodiment of a nib with a fiber tip.

Turning now to FIG. 10. FIG. 10 depicts an embodiment of a nib with a fiber tip. In an embodiment, nib 1048 includes one or more features of the nibs described in connection with FIGS. 1A, 1B, 2, 3, 4, 5, 6, 7, 8 and 9. The nib 1048 includes a porous and flexible tip at the first end 1052. In some embodiments, the porous and flexible tip may provide a desired effect of ink application to a substrate such as skin.

For example, a porous and flexible tip may provide aesthetically pleasing detail and outlines for designs. A user can use porous and flexible tip nib such as nib 1048 in conjunction with a semi-permanent tattoo applicator (e.g., ink applicator 100 of FIG. 1) can allow a user the creative freedom to create freehand designs with fine detail. Additionally, a porous and flexible tip such as the first end 1052 of nib 1048 can provide the precision and/or accuracy for writing text, characters, and script. In another embodiment, the porous and flexible tip such as the first end 1052 of nib 1048 can provide stylistic and creative details such as a pointillism effect or a water color effect. In some embodiments, an ink applicator 100 of FIG. 1 can be fitted with a first nib to draw an outline of a design (e.g., nib 640 of FIG. 6). The first nib 640 can be removed and a second nib 1048 can be installed to the ink applicator 100 and a user can fill in the space within the outlined design using the porous and flexible tip.

The nib 1048 includes an opening at the second end 1054. In some embodiments, the opening at the second end 1054 can be used in conjunction with transfer nib 522 of FIG. 5. The transfer nib 522 of FIG. 5 can absorb the ink composition from a reservoir 520 of FIG. 5 and deliver the composition to the nylon brush fibers at the first end 1052. The nib 1048 can have a length from the first end 1052 to the second end 1054 of about 10 mm to about 30 mm. In some embodiments, the nib 1048 can have a length of about 10 mm to about 30 mm, about 15 mm to about 30 mm, about 20 mm to about 30 mm, or about 25 mm to about 30 mm.

In some embodiments described herein, an ink applicator (e.g., semi-permanent tattoo applicator 100) can include an upper body (e.g., upper body 110) without a reservoir (e.g., reservoir 220) and/or a reservoir container (e.g., reservoir container 218). In some embodiments, an ink applicator can include a lower body (e.g., lower body 116) coupled to an upper body, where the upper body includes a nib (e.g., nib 112) comprising a first end (e.g., first end 452) that is external to the upper body and a second end (e.g., second end 454) internal to the upper body, wherein the nib is configured to dispense a semi-permanent ink. The reservoir and/or reservoir container can be added to the ink applicator by decoupling the upper body from the lower body and positioning the reservoir container and/or the reservoir into the lower body. When the upper body is recoupled to the lower body, the second end of the nib can penetrate the reservoir such that the ink composition within the reservoir can be dispensed via the nib onto a substrate (e.g., paper or skin).

In some embodiments, the ink applicator can include the reservoir within the ink applicator. In some embodiments, an ink applicator can include a lower body, a reservoir container contained in a cavity of the lower body, a reservoir contained in a cavity of the reservoir container; and a semi-permanent ink contained in the reservoir. An upper body can be coupled to the lower body, the upper body where the upper body includes a nib comprising a first end that is external to the upper body and a second end internal to the upper body. The internal portion of the nib can penetrate into the reservoir. In some embodiments, the reservoir includes a fibrous component (e.g., polyethylene terephthalate) and the fibrous component is saturated in the ink composition. In some embodiments, the reservoir does not include a fibrous component.

In some embodiments, the reservoir can include a liquid ink composition. In some embodiments, the reservoir can be refilled with the liquid ink composition. In such embodiments, the ink applicator can include a transfer nib (e.g., transfer nib 522) that facilitates the movement of the liquid ink composition from the reservoir to the nib. In some embodiments, the ink applicator can include a reservoir container contained in a cavity of the lower body, a reservoir contained in a cavity of the reservoir container, and a semi-permanent ink contained in the reservoir. The upper body coupled to the lower body can include a nib comprising a first end that is external to the upper body and a second end internal to the upper body, and a transfer nib that contacts the second end of the nib and the semi-permanent ink contained in the reservoir. To mitigate settling of components of the liquid ink composition in the reservoir, in some embodiments, the reservoir can include an agitator. In some embodiments, the agitator is a metallic sphere.

In some instances, a user may wish to switch colors or types of ink composition. In such incidences, embodiments described herein can include an ink applicator system having a plurality of nibs that correspond to a reservoir and/or a refillable vessel of ink composition. In some embodiments, a plurality of nibs (e.g., nibs 640, 742, 844, 946, 1048) can correspond to a particular ink composition. In some embodiments, a first plurality of nibs can correspond to a first color of ink composition. In some embodiments, a second plurality of nibs can correspond to a second color of ink composition. In some embodiments, a third plurality of nibs can correspond to a liquid ink composition (e.g., a reservoir determined to be filled with liquid ink composition). In some embodiments, a fourth plurality of nibs can correspond to a reservoir which includes a fiber (e.g., polyester fiber, acrylic fiber, nylon brush fibers, and sintered polyethylene). In some embodiments, an ink applicator system can include nibs corresponding to multiple different metrics of ink composition (e.g., color, liquid, refillable reservoir, ink composition saturated reservoir, ink volume, ink composition viscosity).

Methods

Also described herein are methods for using the ink applicator and applying ink compositions. In some embodiments, methods for applying ink onto skin include coupling a nib (e.g., nibs 640, 742, 844, 946, and/or 1048) to an upper body (e.g., upper body 110) of an ink applicator (e.g., semi-permanent tattoo applicator 100) comprising any of the ink compositions described herein; and applying the ink composition of the ink applicator to a portion of the skin.

In some embodiments, the ink applicator is a marker. In some embodiments, the ink applicator is a pen. The ink composition, in some embodiments, is a liquid. In some embodiments, an agitator is included in the reservoir (e.g., reservoir 220) of ink to facilitate mixing of the ink composition. In some embodiments, a method can further comprise agitating the ink applicator to begin the flow of ink composition from a reservoir of the ink applicator to the nib.

In some instances, a user may wish to switch colors, types of ink composition, refill, or replace the ink composition in the reservoir. In some embodiments, the method can include decoupling the upper body of the ink applicator from a lower body (e.g., lower body 116) of the ink applicator, removing the reservoir from the lower body; and replacing the reservoir with a different reservoir.

In some embodiments, the reservoir may be empty of ink a refill. I such embodiments, the reservoir can be refilled. In some embodiments, methods described herein can further include decoupling the upper body of the ink applicator from a lower body of the ink applicator, removing the reservoir from the lower body, and filling the reservoir with additional ink composition.

In some embodiments, a user may wish to change a nib to attain a desired aesthetic or effect. In some embodiments, methods disclosed herein can further include decoupling the nib from the ink applicator, coupling a different nib to the ink applicator, and applying the ink from the ink applicator and different nib to the portion of the skin.

Compositions

In some embodiments, the compositions provided herein include a semi-permanent colorant (e.g., genipin, a genipin derivative, lawsone, a lawsone derivative, or a combination thereof, e.g., any of the combinations described herein); a solvent; and a humectant. In some embodiments, the compositions provided herein include a semi-permanent colorant (e.g., genipin, a genipin derivative, lawsone, a lawsone derivative, or a combination thereof, e.g., any of the combinations described herein); a solvent; and a thickening agent. In some embodiments, the compositions provided herein include a semi-permanent colorant; a solvent; and a humectant. In some embodiments, the compositions provided herein include a semi-permanent colorant; a solvent; a thickening agent, and a humectant. In some embodiments, the composition further includes a film-forming agent. In some embodiments, the composition includes a preservative. In some embodiments, the ink compositions provided herein include a semi-permanent colorant; a solvent; and a film-forming agent. In some embodiments, the ink compositions described herein can be suitable for application to skin using an ink applicator (e.g., semi-permanent tattoo applicator 100). International Application No. PCT/CA2021/050790 describes genipin-based compositions that can be suitable for inkjet printing and is incorporated herein by reference in its entirety. As used herein, a "semi-permanent colorant" refers to a colorant that penetrates one or more layers of the skin and is unable to be removed from the skin without physical disruption or natural desquamation of the skin. In some embodiments, a semi-permanent colorant can include a colorant precursor, for example, a molecule, such as genipin, that expresses color upon reaction with one or more other molecules. In some embodiments, a semi-permanent colorant may penetrate the stratum corneum and react with other molecules, e.g., other colorant molecules and/or other molecules present in the stratum corneum, such that the semi-permanent colorant is immobilized within the stratum corneum. In some embodiments, the semi-permanent colorant may cross-link with collagen or keratin found in the stratum corneum. In some embodiments, the semi-permanent colorant may react with other molecules, e.g., other colorant molecules and/or other molecules present in the stratum corneum, to form a molecule that is too large to diffuse out of the stratum corneum. In some embodiments, the semi-permanent colorant may react with other molecules, e.g., other colorant molecules and/or other molecules present in the stratum corneum to form a molecule that is incorporated into the structure of the stratum corneum. In some embodiments, wherein the semi-permanent colorant penetrates the stratum corneum, the colorant residence time is determined by the natural skin desquamation process. In some embodiments, the semi-permanent colorant cannot be washed off, for example, by water, soap, and/or isopropanol. In some embodiments, a semi-permanent colorant includes a natural or synthetic pigment or dye. Non-limiting examples of semi-permanent colorants include genipin, a genipin derivative, lawsone, and a lawsone derivative.

As used herein, "genipin" refers to genipin extract, partially purified genipin extract, and/or purified genipin, as described further herein. Genipin is derived from an iridoid glycoside called geniposide, which is present in nearly 40 plant species. Additionally, genipin is a precursor to gardenia blue that undergoes a transformative reaction upon exposure to amine groups to form a blue colorant (see, for example, Touyama et al., *Chem. Pharm. Bull.* 42:668-673, 1994; and Touyama et al., *Chem. Pharm. Bull.* 42(8):1571-1578, 1994; both of which are incorporated by reference herein in their entireties). When placed in contact with skin, genipin can react with the amines in skin to generate the polymer-based and/or oligomer-based blue color in situ.

A "genipin derivative" is a compound having a genipin core. In some embodiments, a genipin derivative is a compound having the following core structure:

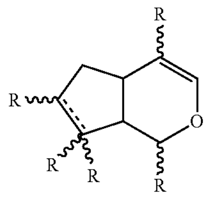

Non-limiting examples of genipin derivatives include those described in International Application No. PCT/US2021/045767, which is incorporated herein by reference in its entirety. In some embodiments, genipin derivatives can include compounds of Formula I:

I

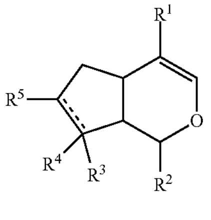

or a salt (e.g., pharmaceutically acceptable salt) thereof, wherein:

$R^1$ is —C(═O)O$R^6$, $C_{1-6}$ alkyl, or $C_{6-10}$ aryl, wherein said $C_{1-6}$ alkyl and $C_{6-10}$ aryl are each optionally substituted with 1-5 $R^7$;

$R^6$ is H, $C_{1-6}$ alkyl, or $C_{6-10}$ aryl, wherein said $C_{1-6}$ alkyl and $C_{6-10}$ aryl are each optionally substituted with 1-5 $R^7$;

each $R^7$ is independently an electron withdrawing or an electron donating group;

$R^2$ is H, —O$R^9$, or OC(═O)$R^{9A}$;

$R^9$ is selected from the group consisting of: H, $C_{1-6}$ alkyl, $C_{6-10}$ aryl, and a hydroxyl-protecting group;

$R^{9A}$ is selected from $C_{1-6}$ alkyl and $C_{6-10}$ aryl; and the dotted line indicates the optional presence of a double bond;

wherein if the double bond is absent, then $R^4$ and $R^5$ together with the carbon atoms to which they are attached form a 3-4 membered heterocyclic ring and $R^3$ is —OH or —$CH_2$OH; or if the double bond is present, then $R^4$ and $R^5$ are absent and $R^3$ is selected from the group consisting of: —N$R^7R^8$, —$CH_2$N$R^7R^8$, —C(═O)O$R^{10}$, —C(═O)N $R^{10}R^{10}$, —CH(═O), phenyl, —CH$R^{10}R^{10}$, —CH═CH$R^{10}$, —CH═C$R^{10}R^{10}$, —$CH_2$O$R^{10}$, and phenyl substituted with 1-5 $R^7$;

wherein $R^{10}$ is selected from H, $C_{1-6}$ alkyl, alkoxy, oxo, —OH, —CH(═O), —C(═O)O$R^6$, phenyl, and phenyl substituted with 1-5 $R^7$; and $R^8$ is H or $R^7$.

In some embodiments:

$R^1$ is —C(═O)O$R^6$ or phenyl substituted with 1-5 $R^7$;

$R^6$ is H, $C_{1-6}$ alkyl, or phenyl substituted with 1-5 $R^7$;

$R^2$ is H, —O$R^9$, or OC(═O)$R^9$;

$R^9$ is H or $C_{1-6}$ alkyl;

if the double bond is present, then $R^4$ and $R^5$ are absent and $R^3$ is selected from the group consisting of: —N$R^7R^8$, —$CH_2$N$R^7R^8$, —C(═O)O$R^{10}$, —CH(═O), phenyl, —CH$R^{10}R^{10}$, —CH═CH$R^{10}$, —$CH_2$O$R^{10}$, diethyl malonate, and phenyl substituted with 1-5 $R^7$; and $R^{10}$ is selected from H, $C_{1-6}$ alkyl, alkoxy, oxo, —OH, —CH(═O) and phenyl substituted with 1-5 $R^7$.

In some embodiments:

$R^3$ is selected from the group consisting of: —N$R^7R^8$, —$CH_2$N$R^7R^8$, —C(═O)O$R^{10}$, —C(═O)N $R^{10}R^{10}$, —CH(═O), phenyl, —CH$R^{10}R^{10}$, —CH═CH$R^{10}$, —CH═C$R^{10}R^{10}$, —$CH_2$O$R^{10}$, and phenyl substituted with 1-5 $R^7$;

$R^1$ is —C(═O)OH;

$R^2$ is —OH; and $R^{10}$ is selected from H, $C_{1-6}$ alkyl, alkoxy, oxo, —OH, —CH(═O), —C(═O)O$R^6$, phenyl, and phenyl substituted with 1-5 $R^7$.

Non-limiting examples of genipin derivatives include compounds of Formula I:

I

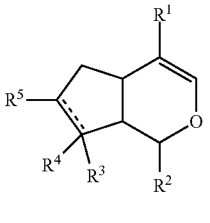

wherein:

$R^1$ is —C(═O)O$R^6$ or phenyl substituted with 1-5 $R^7$;

$R^6$ is H, $C_{1-6}$ alkyl, or phenyl substituted with 1-5 $R^7$;

each $R^7$ is independently an electron withdrawing or an electron donating group;

$R^2$ is H, —O$R^9$, or —OC(═O)$R^9$;

$R^9$ is H or $C_{1-6}$ alkyl; and the dotted line indicates the optional presence of a double bond;

wherein if the double bond is absent, then $R^4$ and $R^5$ together with the carbon atoms to which they are attached form a 3-4 membered heterocyclic ring and $R^3$ is —OH or —$CH_2OH$; or if the double bond is present, then $R^4$ and $R^5$ are absent and $R^3$ is selected from the group consisting of: —$NR^7R^8$, —$CH_2NR^7R^8$, —C(═O)$OR^{10}$, —CH(═O), phenyl, —$CHR^{10}R^{10}$, —CH═$CHR^{10}$, —$CH_2OR^{10}$, diethyl malonate, and phenyl substituted with 1-5 $R^7$;

wherein each $R^{10}$ is independently selected from H, $C_{1-6}$ alkyl, alkoxy, —OH, —CH(═O), and phenyl substituted with 1-5 $R^7$; and $R^8$ is H or $R^7$.

In some embodiments, the Formula I has formula:

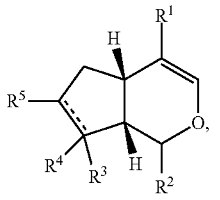

or a salt (e.g., pharmaceutically acceptable salt) thereof.

In some embodiments, the Formula I has formula

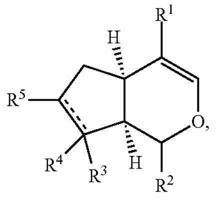

or a salt (e.g., pharmaceutically acceptable salt) thereof.

In some embodiments, the Formula I has formula

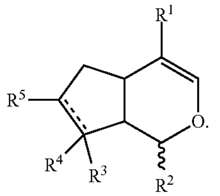

In some embodiments, the Formula I has formula:

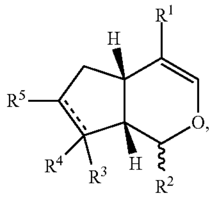

or a salt (e.g., pharmaceutically acceptable salt) thereof.

In some embodiments, $R^6$ methyl. In some embodiments, $R^1$ is —C(═O)$OR^6$ and $R^6$ is methyl. In some embodiments, $R^1$ is —C(═O)$OR^6$ and $R^6$ is phenyl substituted with 1-5 $R^7$.

In some embodiments, $R^2$ is —OC(═O)$CH_3$. In some embodiments, $R^2$ is —OH.

In some embodiments, $R^2$ is $OR^9$ or OC(═O)$R^{9A}$.

In some embodiments, $R^2$ is $OR^9$.

In some embodiments, $R^2$ is OC(═O)$R^{9A}$.

In some embodiments, $R^9$ is selected from the group consisting of: H, $C_{1-6}$ alkyl, and $C_{6-10}$ aryl.

In some embodiments, $R^9$ is a hydroxyl-protecting group. Suitable examples of protecting groups are described in Greene, Wuts, at al., Protective groups in organic synthesis, Fourth Edition, 2006 (ISBN: 9780471697541), and include t-butyl, allyl, methoxymethyl (MOM), tri($C_{1-6}$ alkyl)silyl (e.g., tert-butyldimethylsilyl (TBS), trimethylsilyl (TMS), or triethylsilyl (TES)), acyl (e.g., benzoyl, pivaloyl, or acetyl), acetonide, tetrahydropyranyl (THP), and benzylidene acetal. In some embodiments, the hydroxyl-protecting group is tri($C_{1-6}$ alkyl)silyl. In some embodiments, the hydroxyl-protecting group is tert-butyldimethylsilyl (TBS), trimethylsilyl (TMS), or triethylsilyl (TES).

In some embodiments, $R^{9A}$ is $C_{1-6}$ alkyl.

In some embodiments, $R^{9A}$ is $C_{6-10}$ aryl.

In some embodiments, the double bond is absent. In some embodiments, $R^4$ and $R^5$ together with the carbon atoms to which they are attached form a 3-membered heterocyclic ring and $R^3$ is —$CH_2OH$. In some embodiments, $R^4$ and $R^5$ together with the carbon atoms can form:

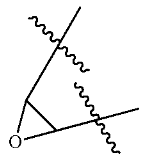 [SMILES: *C1OC1*]

In some embodiments, $R^4$ and $R^5$ together with the carbon atoms to which they are attached form a 4-membered heterocyclic ring and $R^3$ is —OH. In some embodiments, $R^4$ and $R^5$ together with the carbon atoms can form:

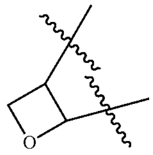

In some embodiments, the double bond is present. In some embodiments, $R^1$ is phenyl substituted with 1-3 $R^7$. In some embodiments, $R^1$ is —C(═O)$OR^6$ and $R^6$ is phenyl substituted with 1-3 $R^7$. In some embodiments, $R^2$ is —OH and $R^3$ is $CH_2OH$.

In some embodiments, $R^1$ is $C_{6-10}$ aryl, optionally substituted with 1-5 $R^7$.

In some embodiments, $R^6$ is $C_{6-10}$ aryl, optionally substituted with 1-5 $R^7$.

In some embodiments, $R^3$ is selected from the group consisting of: —$NR^7R^8$, —$CH_2$—$NR^7R^8$, —C(═O)$OR^{10}$, —CH(═O), phenyl, —$CHR^{10}R^{10}$, —CH═$CHR^{10}$, —$CH_2OR^{10}$, diethyl malonate, and phenyl substituted with 1-5 $R^7$; $R^1$ is —C(═O)OH; and $R^2$ is —OH.

In some embodiments, $R^3$ is selected from —$CH_2NR^7R^8$, —C(=O)$OR^{10}$, —C(=O)N $R^{10}R^{10}$, —CH(=O), phenyl, —CH(OH)$R^{10}$, —CH=$CHR^{10}$, —CH=$CR^{10}R^{10}$, —$CH_2OR^{10}$, and phenyl substituted with 1-5 $R^7$.

In some embodiments, $R^{10}$ is selected from H, $C_{1-6}$ alkyl, —OH, —CH(=O), —C(=O)$OR^6$, phenyl, and phenyl substituted with 1-5 $R^7$.

In some embodiments, $R^{10}$ is selected from H, $C_{1-6}$ alkyl, —CH(=O), —C(=O)$OR^6$, phenyl, and phenyl substituted with 1-5 $R^7$.

In some embodiments, $R^{10}$ is selected from H, $C_{1-6}$ alkyl, phenyl, and phenyl substituted with 1-5 $R^7$.

In some embodiments, $R^{10}$ is H.

In some embodiments, $R^{10}$ is selected from $C_{1-6}$ alkyl, phenyl, and phenyl substituted with 1-5 $R^7$.

In some embodiments, $R^3$ is —CH(OH)$R^{10}$; and $R^{10}$ is $C_{1-6}$ alkyl, phenyl, or phenyl substituted with 1-5 $R^7$.

In some embodiments, $R^3$ is —C(=O)N $R^{10}R^{10}$.

In some embodiments, $R^3$ is —CH=$CHR^{10}$; and $R^{10}$ is $C_{1-6}$ alkyl, phenyl, or phenyl substituted with 1-5 $R^7$. In some embodiments, $R^{10}$ is phenyl or phenyl substituted with 1-5 $R^7$.

In some embodiments, $R^3$ is phenyl.

In some embodiments, $R^3$ is phenyl substituted with 1-5 $R^7$.

In some embodiments, $R^3$ is —CH=$CR^{10}R^{10}$; each $R^{10}$ is independently —CH(=O) or —C(=O)$OR^6$; and $R^6$ is $C_{1-6}$ alkyl, optionally substituted with 1-5 $R^7$. In some embodiments, $R^3$ is diethyl malonate.

In some embodiments, the genipin derivative is a compound selected from the group consisting of the compounds in Table 1.

TABLE 1

| Compound # | Structure |
|---|---|
| 1 | 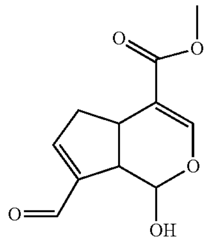 |
| 2 | 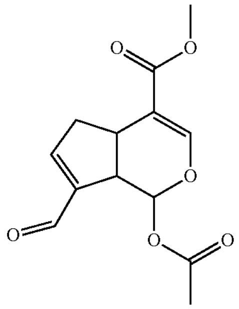 [SMILES: COC(=O)C1=COC(OC(C)=O)C2C(C=O)=CCC12] |

TABLE 1-continued

| Compound # | Structure |
|---|---|
| 3 | 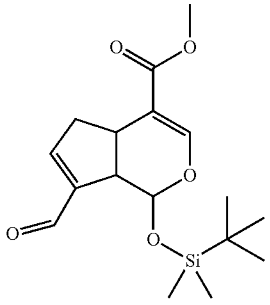 [SMILES: COC(=O)C1=COC(O[Si](C)(C)C(C)(C)C)C2C(C=O)=CCC12] |
| 4 | 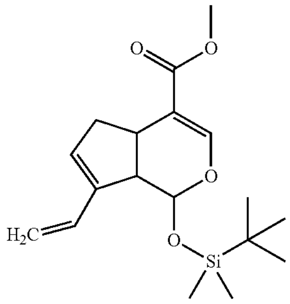 [SMILES: C=CC1=CCC2C(C(=O)OC)=COC(O[Si](C)(C)C(C)(C)C)C12] |
| 5 | 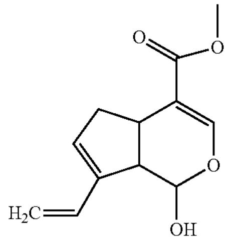 [SMILES: C=CC1=CCC2C(C(=O)OC)=COC(O)C12] |
| 6 | 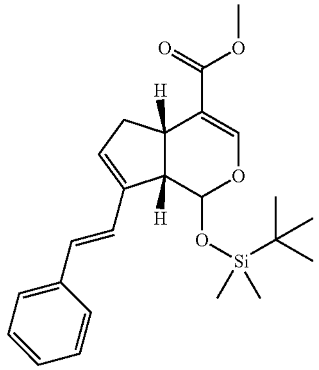 [SMILES: COC(=O)C1=COC(O[Si](C)(C)C(C)(C)C)[C@@H]2C(/C=C/c3ccccc3)=CC[C@H]12] |
| 7 | 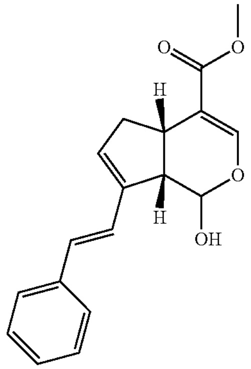 [SMILES: COC(=O)C1=COC(O)[C@@H]2C(/C=C/c3ccccc3)=CC[C@H]12] |

TABLE 1-continued
| Compound # | Structure |
| --- | --- |
| 8 | 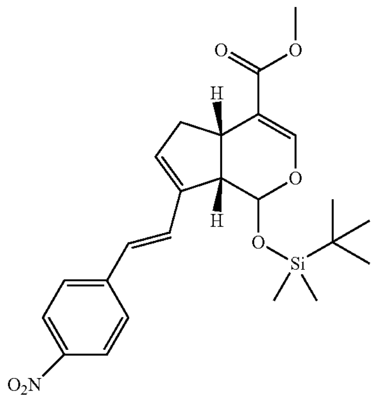 [SMILES: COC(=O)C1=COC(O[Si](C)(C)C(C)(C)C)[C@@H]2C(/C=C/c3ccc([N+](=O)[O-])cc3)=CC[C@H]12] |
| 9 | 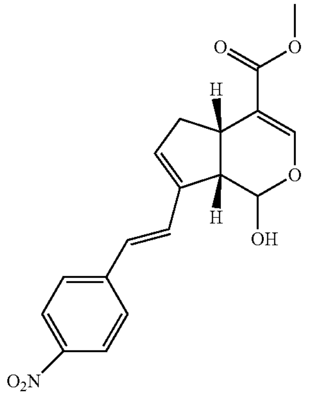 [SMILES: COC(=O)C1=COC(O)[C@@H]2C(/C=C/c3ccc([N+](=O)[O-])cc3)=CC[C@H]12] |
| 10 | 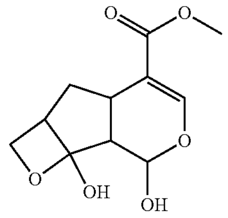 [SMILES: COC(=O)C1=COC(O)C2C1CC1COC12O] |
| 11 | 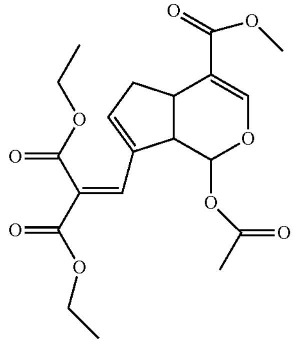 [SMILES: CCOC(=O)C(=CC1=CCC2C(C(=O)OC)=COC(OC(C)=O)C12)C(=O)OCC] |
TABLE 1-continued
| Compound # | Structure |
| --- | --- |
| 12 | 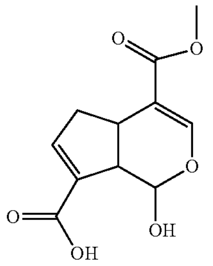 [SMILES: COC(=O)C1=COC(O)C2C(C(=O)O)=CCC12] |
| 13 | 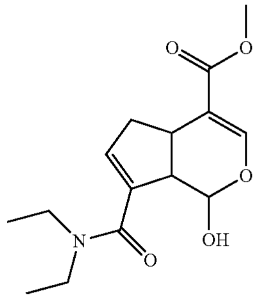 [SMILES: CCN(CC)C(=O)C1=CCC2C(C(=O)OC)=COC(O)C12] |
| 15 | 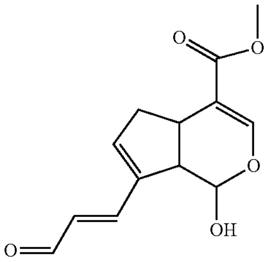 [SMILES: COC(=O)C1=COC(O)C2C(/C=C/C=O)=CCC12] |
| 16 | 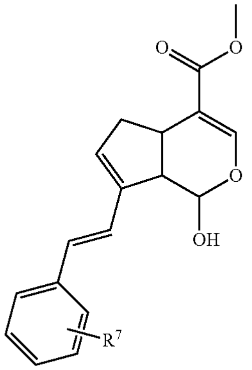 |
| 17 | 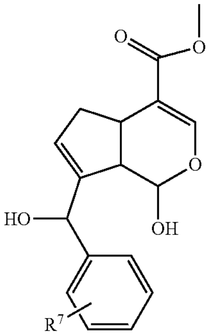 |

TABLE 1-continued

| Compound # | Structure |
| --- | --- |
| 18 | 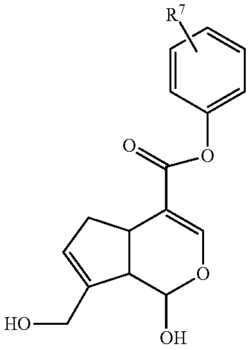 |
| 19 | 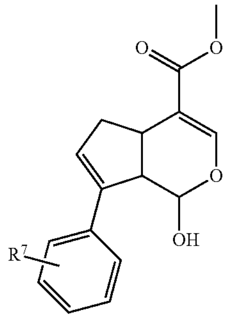 |
| 20 | 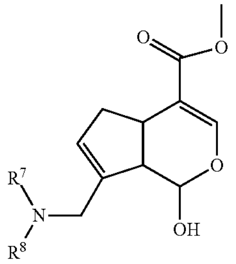 |
| 21 | 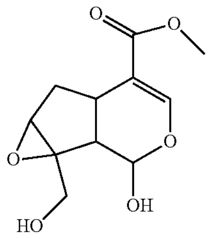 [SMILES: COC(=O)C1=COC(O)C2C1CC1OC12CO] |
| 22 | 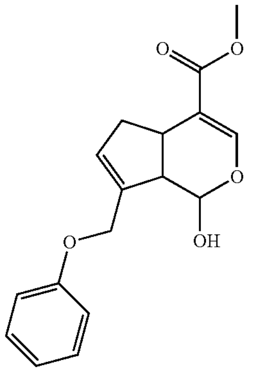 [SMILES: COC(=O)C1=COC(O)C2C(COc3ccccc3)=CCC12] |

TABLE 1-continued

| Compound # | Structure |
| --- | --- |
| 23 | 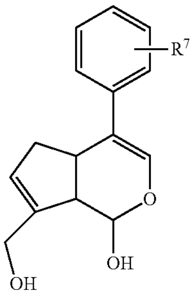 |

In some embodiments, the electron withdrawing or electron donating group of $R^7$ is selected from the group consisting of: —($C_{1-9}$ alkyl), —($C_{2-9}$ alkenyl), phenyl, —$NR^8R^8$, —$OR^8$, —NHC(═O)$R^8$, —OC(═O)$R^8$, —$SR^8$, —$CO_2^-$, —$SO_2CF_3$, —$NO_2$, —$SO_2R^8$, —CN, —$CR^{93}$, —$COR^9$, —CHO, —$CO_2R^8$, —C(═O)$NR^8$ $R^8$, halide, and —NO. In some embodiments, the electron withdrawing or electron donating group of $R^7$ is selected from the group consisting of: —($C_{1-9}$ alkyl), —($C_{2-9}$ alkenyl), phenyl, —$NR^8R^8$, —$OR^8$, —OC(═O)$R^8$, —$SR^8$, —$CO_2^-$, —$SO_2CF_3$, —$NO_2$, —$SO_2R^8$, —CN, —$CR^9_3$, —$COR^9$, —CHO, —$CO_2R^8$, —C(═O)$NR^8$ $R^8$, and —NO.

In some embodiments, $R^8$ is H or $R^7$. In some embodiments, $R^8$ is selected from the group consisting of: H, —($C_{1-9}$ alkyl), and —($C_{2-9}$ alkenyl); and $R^9$ is halide. In some embodiments, $R^8$ is H.

In some embodiments, a genipin derivative is a compound of Formula IIa:

IIa

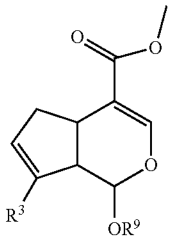

or a salt (e.g., a pharmaceutically acceptable salt) thereof, wherein:

$R^9$ is selected from the group consisting of: H, $C_{1-6}$ alkyl, $C_{6-10}$ aryl, and a hydroxyl-protecting group, wherein said $C_{1-6}$ alkyl and $C_{6-10}$ aryl are each optionally substituted with 1-5 $R^7$;

$R^3$ is selected from the group consisting of: —$CH_2NR^7R^8$, —C(═O)$OR^{10}$, —C(═O)N $R^{10}R^{10}$, —CH(═O), —$CHR^{10}R^{10}$, —CH═$CHR^{10}$, —CH═$CR^{10}R^{10}$, —$CH_2OR^{10}$, phenyl, and phenyl substituted with 1-5 $R^7$;

wherein each $R^{10}$ is independently selected from H, $C_{1-6}$ alkyl, —OH, —CH(═O), C(═O)$OR^9$, phenyl, and phenyl substituted with 1-5 $R^7$; and $R^7$ is an electron withdrawing or an electron donating group; and $R^8$ is H or $R^7$.

In some embodiments:

$R^3$ is selected from —C(═O)$OR^{10}$, —CH(═O), and —$CH_2OR^{10}$;

$R^{10}$ is selected from H, $C_{1-6}$ alkyl, phenyl, and phenyl substituted with 1-5 $R^7$; and $R^9$ is selected from $C_{1-6}$ alkyl, $C_{6-10}$ aryl, and a hydroxyl-protecting group, wherein said $C_{1-6}$ alkyl and $C_{6-10}$ aryl are each optionally substituted with 1-5 $R^7$.

In some embodiments, $R^3$ is —C(=O)$OR^{10}$.

In some embodiments, $R^3$ is —CH(=O).

In some embodiments, $R^3$ is —$CH_2OR^{10}$.

In some embodiments:

$R^3$ is —CH=$CR^{10}R^{10}$;

each $R^{10}$ is independently CH(=O) or C(=O)$OR^9$; and $R^9$ is selected from $C_{1-6}$ alkyl, $C_{6-10}$ aryl, and a hydroxyl-protecting group, wherein said $C_{1-6}$ alkyl and $C_{6-10}$ aryl are each optionally substituted with 1-5 $R^7$.

In some embodiments:

$R^3$ is selected from —$CH_2NR^7R^8$, —C(=O)N $R^{10}R^{10}$, —CH(OH)$R^{10}$, —CH=$CHR^{10}$, phenyl, and phenyl substituted with 1-5 $R^7$; and each $R^{10}$ is independently selected from $C_{1-6}$ alkyl, phenyl, and phenyl substituted with 1-5 $R^7$.

In some embodiments, $R^9$ is a hydroxyl-protecting group. In some embodiments, R9 is selected from the group consisting of: t-butyl, allyl, methoxymethyl, tri($C_{1-6}$ alkyl)silyl (e.g., tert-butyldimethylsilyl (TBS), trimethylsilyl (TMS), or triethylsilyl (TES)), acyl (e.g., benzoyl, pivaloyl, or acetyl), acetonide, and benzylidene acetal. In some embodiments, the hydroxyl-protecting group is tri($C_{1-6}$ alkyl)silyl. In some embodiments, the hydroxyl-protecting group is tert-butyldimethylsilyl (TBS), trimethylsilyl (TMS), or triethylsilyl (TES).

In some embodiments, $R^9$ is $C_{1-6}$ alkyl.

In some embodiments, $R^9$ is $C_{6-10}$ aryl.

In some embodiments, the Formula IIa has formula:

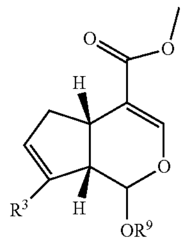

or a salt (e.g., a pharmaceutically acceptable salt) thereof.

In some embodiments, the Formula IIa has formula:

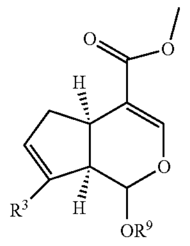

or a salt (e.g., a pharmaceutically acceptable salt) thereof.

In some embodiments, the Formula IIa has formula:

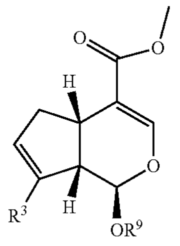

or a salt (e.g., a pharmaceutically acceptable salt) thereof.

In some embodiments, the Formula IIa has formula:

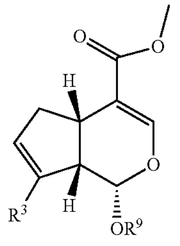

or a salt (e.g., a pharmaceutically acceptable salt) thereof.

In some embodiments, the Formula IIa has formula:

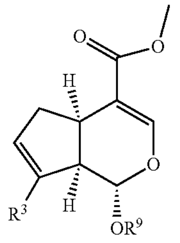

or a salt (e.g., a pharmaceutically acceptable salt) thereof.

In some embodiments, the Formula IIa has formula:

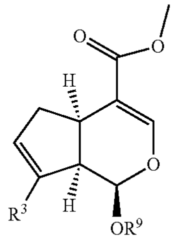

or a salt (e.g., a pharmaceutically acceptable salt) thereof.

In some embodiments, the genipin derivative is a compound of Formula IIa:

IIa

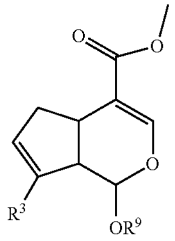

wherein:

$R^9$ is selected from the group consisting of: H, $C_{1-6}$ alkyl, $C_{6-10}$ aryl, and a hydroxyl-protecting group, wherein said $C_{1-6}$ alkyl and $C_{6-10}$ aryl are each optionally substituted with 1-5 $R^7$;

$R^3$ is selected from the group consisting of: —C(═O)OR$^{10}$, —CH(═O), —CHR$^{10}$R$^{10}$, —CH═CHR$^{10}$, —CH$_2$OR$^{10}$, —C(═O)NR$^{10}$R$^{10}$, phenyl, and phenyl substituted with 1-5 $R^7$;

wherein each $R^{10}$ is independently selected from H, —OH, —CH(═O), diethyl malonate, phenyl, and phenyl substituted with 1-5 $R^7$; and $R^7$ is an electron withdrawing or an electron donating group, e.g., any of the electron withdrawing or an electron donating group described herein.

In some embodiments, $R^9$ is tert-butyldimethylsilyl (TBS). In some embodiments, $R^3$ is selected from the group consisting of: —C(═O)OR$^{10}$, —CH(═O), —CH═CHR$^{10}$, —CH$_2$OR$^{10}$, and —C(═O)NR$^{10}$R$^{10}$. In some embodiments, each $R^{10}$ is independently selected from H, $C_{1-6}$ alkyl, —CH(═O), -phenyl, and phenyl substituted with 1-5 $R^7$. In some embodiments, $R^{10}$ is phenyl substituted with —NO$_2$. In some embodiments, $R^3$ is —C(═O)OR$^{10}$ and $R^{10}$ is H. In some embodiments, $R^3$ is —CH═CHR$^{10}$ and $R^{10}$ is selected from the group consisting of: H, CH(═O), phenyl, and phenyl substituted with 1-5 $R^7$. In some embodiments, $R^3$ is —CH═CHR$^{10}$ and $R^{10}$ is phenyl substituted with —NO$_2$. In some embodiments, $R^3$ is —CH$_2$OR$^{10}$ and $R^{10}$ is H or phenyl. In some embodiments, $R^3$ is C(═O)NR$^{10}$R$^{10}$ and $R^{10}$ is $C_{1-6}$ alkyl. In some embodiments, $R^3$ is C(═O)NR$^{10}$R$^{10}$ and $R^{10}$ is ethyl.

In some embodiments, $R^9$ is —OH. In some embodiments, $R^3$ is selected from the group consisting of: —C(═O)OR$^{10}$, —CH(═O), —CH═CHR$^{10}$, —CH$_2$OR$^{10}$, and —C(═O)NR$^{10}$R$^{10}$. In some embodiments, each $R^{10}$ is independently selected from H, $C_{1-6}$ alkyl, —CH(═O), -phenyl, and phenyl substituted with 1-5 $R^7$. In some embodiments, $R^{10}$ is phenyl substituted with —NO$_2$. In some embodiments, $R^3$ is —C(═O)OR$^{10}$ and $R^{10}$ is H. In some embodiments, $R^3$ is —CH═CHR$^{10}$ and $R^{10}$ is selected from the group consisting of: H, CH(═O), phenyl, and phenyl substituted with 1-5 $R^7$. In some embodiments, $R^3$ is —CH═CHR$^{10}$ and $R^{10}$ is phenyl substituted with —NO$_2$. In some embodiments, $R^3$ is —CH$_2$OR$^{10}$ and $R^{10}$ is H or phenyl. In some embodiments, $R^3$ is C(═O)NR$^{10}$R$^{10}$ and $R^{10}$ is $C_{1-6}$ alkyl. In some embodiments, $R^3$ is C(═O)NR$^{10}$R$^{10}$ and $R^{10}$ is ethyl.

In some embodiments, the genipin derivative is a compound as delineated in Table 2.

TABLE 2

| Compound # | Structure |
|---|---|
| 1 | 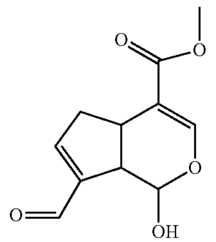 [SMILES: COC(=O)C1=COC(O)C2C(C=O)=CCC12] |
| 3 | 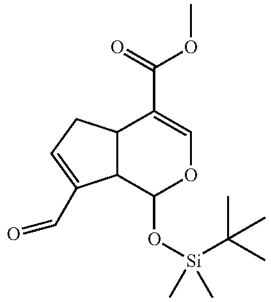 [SMILES: COC(=O)C1=COC(O[Si](C)(C)C(C)(C)C)C2C(C=O)=CCC12] |
| 4 | 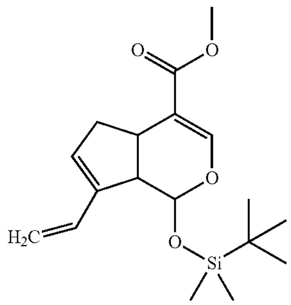 [SMILES: C=CC1=CCC2C(C(=O)OC)=COC(O[Si](C)(C)C(C)(C)C)C12] |
| 5 | 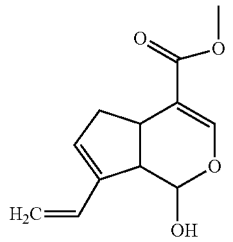 [SMILES: C=CC1=CCC2C(C(=O)OC)=COC(O)C12] |
| 6 | 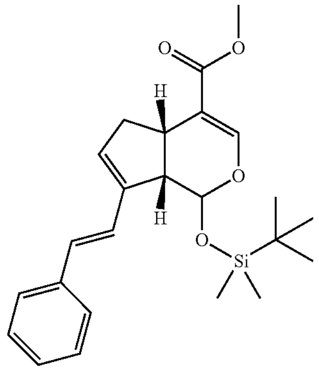 [SMILES: COC(=O)C1=COC(O[Si](C)(C)C(C)(C)C)[C@@H]2C(/C=C/c3ccccc3)=CC[C@H]12] |

TABLE 2-continued
| Compound # | Structure |
| --- | --- |
| 7 | 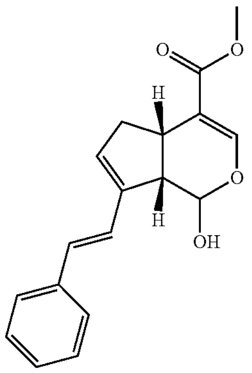 [SMILES: COC(=O)C1=COC(O)[C@@H]2C(/C=C/c3ccccc3)=CC[C@H]12] |
| 8 | 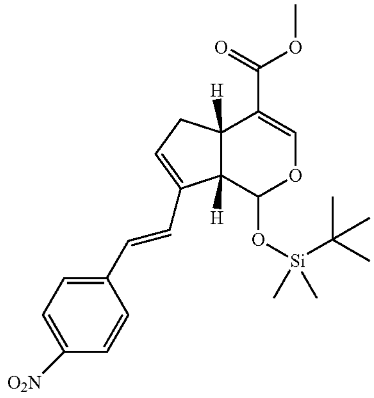 [SMILES: COC(=O)C1=COC(O[Si](C)(C)C(C)(C)C)[C@@H]2C(/C=C/c3ccc([N+](=O)[O-])cc3)=CC[C@H]12] |
| 9 | 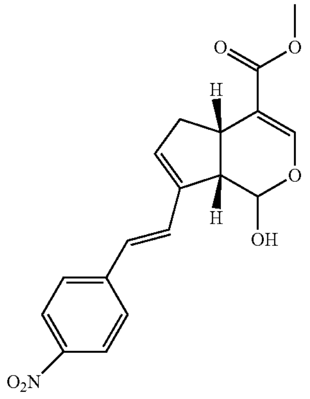 [SMILES: COC(=O)C1=COC(O)[C@@H]2C(/C=C/c3ccc([N+](=O)[O-])cc3)=CC[C@H]12] |
| 12 | 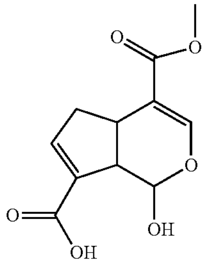 |
TABLE 2-continued
| Compound # | Structure |
| --- | --- |
| 13 | 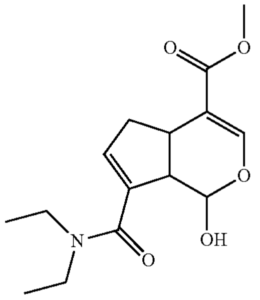 [SMILES: CCN(CC)C(=O)C1=CCC2C(C(=O)OC)=COC(O)C12] |
| 15 | 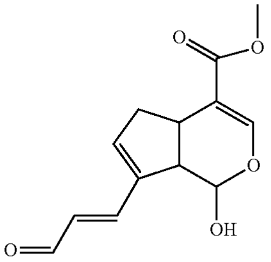 [SMILES: COC(=O)C1=COC(O)C2C(/C=C/C=O)=CCC12] |
| 16 | 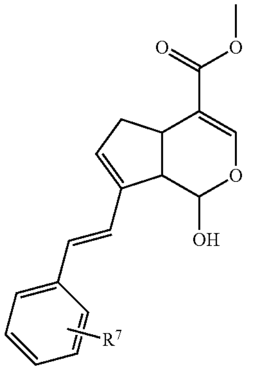 |
| 17 | 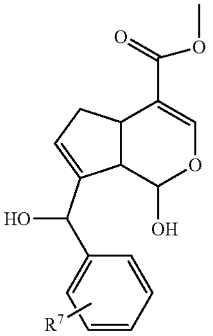 |
| 19 | 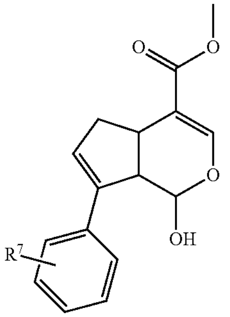 |

TABLE 2-continued

| Compound # | Structure |
|---|---|
| 20 | 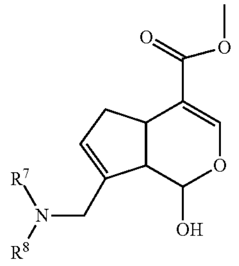 |
| 22 | 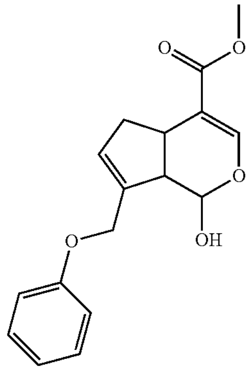 [SMILES: COC(=O)C1=COC(O)C2C(COc3ccccc3)=CCC12] |

In some embodiments, the compound has formula lib:

IIb

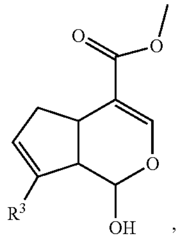
, or a pharmaceutically acceptable salt thereof.

In some embodiments:

$R^3$ is selected from the group consisting of:—$CH_2NR^7R^8$, —C(═O)$OR^{10}$, —CH(═O), —$CHR^{10}R^{10}$, —CH═$CHR^{10}$, —$CH_2OR^{10}$, and phenyl substituted with 1-5 $R^7$;

each $R^{10}$ is independently selected from H, —OH, —CH (═O) and phenyl substituted with 1-5 $R^7$.

In some embodiments, the genipin derivative is a compound of Formula IIb:

IIb

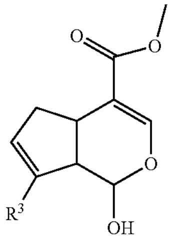

wherein:

$R^3$ is selected from the group consisting of: —$CH_2NR^7R^8$, —C(═O)$OR^{10}$, —CH(═O), —$CHR^{10}R^{10}$, —CH═$CHR^{10}$, —$CH_2OR^{10}$, and phenyl substituted with 1-5 $R^7$;

wherein each $R^{10}$ is independently selected from H, —OH, —CH(═O), and phenyl substituted with 1-5 $R^7$; and $R^7$ is an electron withdrawing or an electron donating group, e.g., any of the electron withdrawing or an electron donating group described herein.

In some embodiments, $R^3$ is selected from the group consisting of: —C(═O)$OR^{10}$, —CH(═O), —CH═$CHR^{10}$, —$CH_2OR^{10}$, and —C(═O)$NR^{10}R^{10}$.

In some embodiments, each $R^{10}$ is independently selected from H, $C_{1-6}$ alkyl, —CH(═O), -phenyl, and phenyl substituted with 1-5 $R^7$. In some embodiments, $R^{10}$ is phenyl substituted with —$NO_2$.

In some embodiments, $R^3$ is —C(═O)$OR^{10}$ and $R^{10}$ is H.

In some embodiments, $R^3$ is —CH═$CHR^{10}$ and $R^{10}$ is selected from the group consisting of: H, CH(═O), phenyl, and phenyl substituted with 1-5 $R^7$. In some embodiments, $R^3$ is —CH═$CHR^{10}$ and $R^{10}$ is phenyl substituted with —$NO_2$.

In some embodiments, $R^3$ is —$CH_2OR^{10}$ and $R^{10}$ is H or phenyl.

In some embodiments, $R^3$ is C(═O)$NR^{10}R^{10}$ and $R^{10}$ is $C_{1-6}$ alkyl.

In some embodiments, $R^3$ is C(═O)$NR^{10}R^{10}$ and $R^{10}$ is ethyl.

In some embodiments, the genipin derivative is a compound as delineated in Table 3.

TABLE 3

| Compound # | Structure |
|---|---|
| 1 | 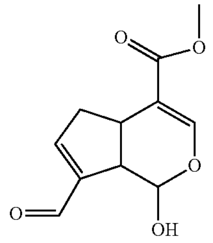 [SMILES: COC(=O)C1=COC(O)C2C(C=O)=CCC12] |
| 5 | 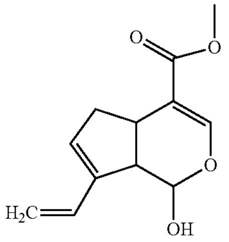 [SMILES: C=CC1=CCC2C(C(=O)OC)=COC(O)C12] |

TABLE 3-continued
| Compound # | Structure |
|---|---|
| 7 | 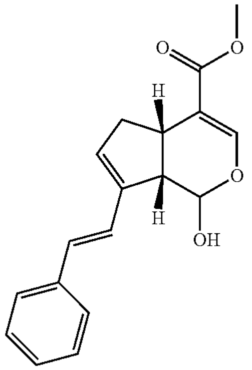 [SMILES: COC(=O)C1=COC(O)[C@@H]2C(/C=C/c3ccccc3)=CC[C@H]12] |
| 9 | 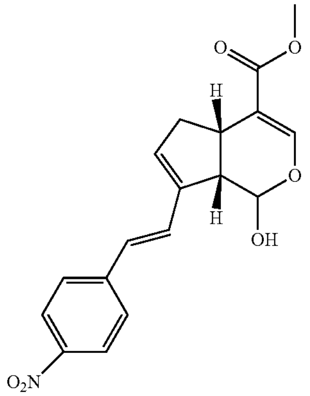 [SMILES: COC(=O)C1=COC(O)[C@@H]2C(/C=C/c3ccc([N+](=O)[O-])cc3)=CC[C@H]12] |
| 12 | 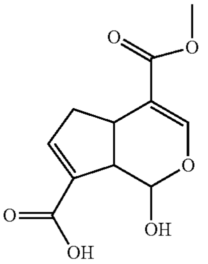 |
| 13 | 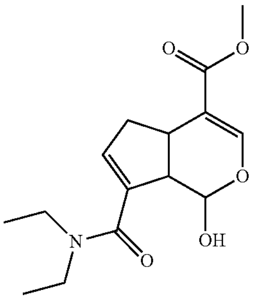 [SMILES: CCN(CC)C(=O)C1=CCC2C(C(=O)OC)=COC(O)C12] |
TABLE 3-continued
| Compound # | Structure |
|---|---|
| 15 | 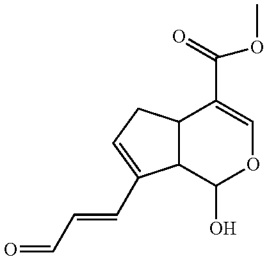 [SMILES: COC(=O)C1=COC(O)C2C(/C=C/C=O)=CCC12] |
| 16 | 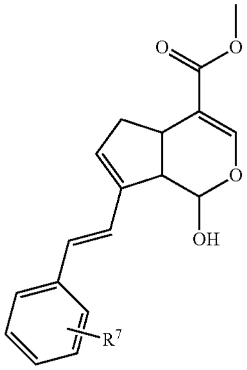 |
| 17 | 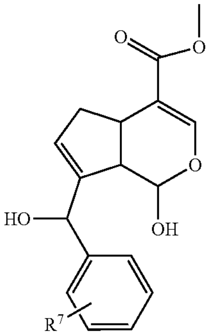 |
| 19 | 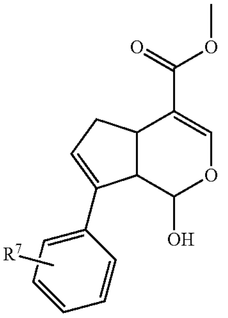 |
| 20 | 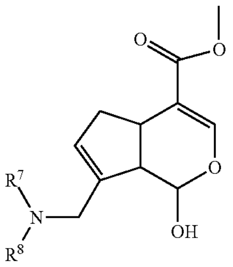 |

TABLE 3-continued

| Compound # | Structure |
|---|---|
| 22 | 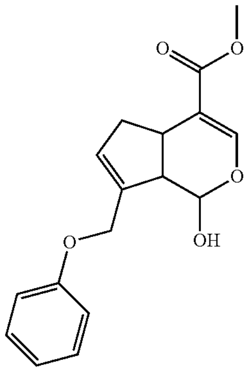 [SMILES: COC(=O)C1=COC(O)C2C(COc3ccccc3)=CCC12] |

In some embodiments, $R^7$ is selected from the group consisting of: —($C_{1-9}$ alkyl), —($C_{2-9}$ alkenyl), phenyl, —$NR^8R^8$, —$OR^8$, —NHC(═O)$R^8$, —OC(═O)$R^8$, —$SR^8$, —$CO_2^-$, —$SO_2CF_3$, —$NO_2$, —$SO_2R^8$, —CN, —$CR^{93}$, —$COR^9$, —CHO, —$CO_2R^8$, —C(═O)$NR^8$ $R^8$, halide, and —NO; wherein $R^8$ is selected from the group consisting of: H, —($C_{1-9}$ alkyl), —($C_{2-9}$ alkenyl), unsubstituted —($C_{2-9}$ alkynyl); and $R^9$ is halide. In some embodiments, $R^7$ is selected from the group consisting of: —($C_{1-9}$ alkyl), —($C_{2-9}$ alkenyl), phenyl, —$NR^8R^8$, —$OR^8$, —OC(═O)$R^8$, —$SR^8$, —$CO_2^-$, —$SO_2CF_3$, —$NO_2$, —$SO_2R^8$, —CN, —$CR^{93}$, —$COR^9$, —CHO, —$CO_2R^8$, —C(═O)$NR^8$ $R^8$, and —NO.

In some embodiments, the chiral carbon atoms in the Formula IIb have the same configuration as in Formula IIa (R or S).

Without being bound by any theory, it is believed that the penetration profile of genipin or a genipin derivative can dictate the color concentration profile in the stratum corneum as the polymer-based and/or oligomer-based colorant is too large to penetrate the skin at relevant concentrations. For example, the average molecular weight of the polymer-based and/or oligomer-based blue colorant from genipin has been reported to be 8900±600 Daltons, and the polymer-based and/or oligomer-based blue colorant comprises 40 to 44 monomer units (see, for example, Touyama et al., *Chem. Pharm. Bull.* 42:668-673, 1994). In some embodiments, the average molecular weight of the monomeric, polymerized and/or oligomerized genipin or a genipin derivative present in the compositions described herein can range from about 200 Daltons to about 15000 Daltons. In some embodiments, the average molecular weight of the polymerized and/or oligomerized genipin or a genipin derivative present in the compositions described herein can range from about 500 Daltons to about 15000 Daltons. In some embodiments, a plurality of different molecular weights of genipin or a genipin derivative can be used. In some embodiments, the compositions described herein can comprise genipin having an average molecular weight from about 200 Daltons to about 15000 Daltons. In some embodiments, the compositions described herein can comprise genipin or a genipin derivative having an average molecular weight of from about 200 to about 1000 Daltons, about 500 to about 1500 Daltons, about 1000 to about 2000 Daltons, about 1500 to about 2500 Daltons, about 2000 to about 3500 Daltons, 3500 to about 5000 Daltons, 5000 to about 6500 Daltons, 6000 to about 8300 Daltons, from about 8300 to about 9500 Daltons, and combinations thereof.

As used herein, "lawsone" refers to 2-hydroxy-1,4-naphthoquinone, also known as hennotannic acid. Lawsone is a red-orange dye present in the leaves of the henna plant (*Lawsonia inermis*) and in the flower of the water hyacinth (*Eichhornia crassipes*).

Lawsone reacts with proteins such as keratin in skin and hair, and the semi-permanent colorant lasts until the skin or hair is shed.

As used herein, "lawsone derivative" refers to a compound having a lawsone core. In some embodiments, a lawsone derivative is a compound having the following core structure:

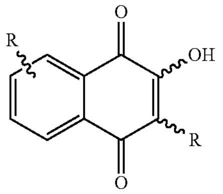

A non-limiting example of a lawsone derivative is the compound as delineated in Table 4.

TABLE 4

| Compound # | Structure |
|---|---|
| 14 | 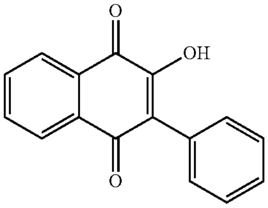 [SMILES: O=C1C(O)=C(c2ccccc2)C(=O)c2ccccc21] |

Further non-limiting examples of lawsone derivatives include compounds of Formula III:

III

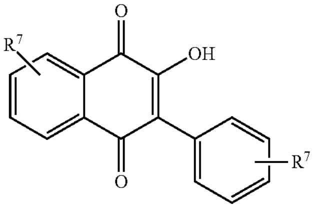

wherein $R^7$ is selected from the group consisting of: —($C_{1-9}$ alkyl), —($C_{2-9}$ alkenyl), phenyl, —$NR^8R^8$, —$OR^8$, —NHC(═O)$R^8$, —OC(═O)$R^8$, —$SR^8$, —$CO_2^-$, —$SO_2CF_3$, —$NO_2$, —$SO_2R^8$, —CN, —$CR^9_3$, —$COR^9$, —CHO, —$CO_2R^8$, —C(═O)$NR^8$ $R^8$, halogen, and —NO; wherein $R^8$ is selected from the group consisting of: H, —($C_{1-9}$ alkyl), and —($C_{2-9}$ alkenyl); and $R^9$ is halide.

In some embodiments, the electron withdrawing or electron donating group of $R^7$ is selected from the group consisting of: —($C_{1-9}$ alkyl), —($C_{2-9}$ alkenyl), phenyl, —$NR^8R^8$, —$OR^8$, —OC(═O)$R^8$, —$SR^8$, —$CO_2^-$, —$SO_2CF_3$, —$NO_2$, —$SO_2R^8$, —CN, —$CR^{93}$, —$COR^9$, —CHO, —$CO_2R^8$, —C(═O)$NR^8$ $R^8$, and —NO.

In some embodiments, the semi-permanent colorant (e.g., genipin, genipin derivative, lawsone, lawsone derivative, or combinations thereof) is purified. The presence of amines, for example, amines that are endogenously present in plant extracts or exogenously introduced, in a genipin or other semi-permanent colorant solution can shorten the shelf life of the semi-permanent colorant solution. For example, with time, the reactive precursors can develop into the polymer-based and/or oligomer-based colorant prior to application to the skin, limiting the penetration of the semi-permanent colorant to the stratum corneum. Penetration of the genipin or other semi-permanent colorant into the deeper layers of the stratum corneum can allow for the subsequent development and retention of the semi-permanent colorant (e.g., polymer-based and/or oligomer-based semi-permanent colorant) in the skin, which can lead to increased semi-permanent tattoo longevity. The semi-permanent tattoo longevity, or the semi-permanent colorant residence time in the skin, can then be limited by the natural skin desquamation process. In some embodiments, the purified semi-permanent colorant has a purity of greater than about 85% w/w. In some embodiments, the purified semi-permanent colorant has a purity of greater than about 86%, about 88%, about 90%, about 92%, about 94%, about 96%, about 98%, about 99%, or about 99.5% w/w of the semi-permanent colorant solution.

In some embodiments, a salt of any of the compounds described herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of this disclosure include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β3-hydroxybutyrate, glycolate, maleate, tartrate, methanesu1fonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of this disclosure include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2—OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the semi-permanent colorant is a combination of two or more semi-permanent colorants (e.g., a combination of two or more of genipin, a genipin derivative, lawsone, and a lawsone derivative). A combination of two or more semi-permanent colorants can include, for example, a combination of two or more genipin derivatives; a combination of one or more genipin derivatives and lawsone; a combination of one or more genipin derivatives and one or more lawsone derivatives; a combination of lawsone and one or more lawsone derivatives; and a combination of one or more genipin derivatives, lawsone, and one or more lawsone derivatives. In some embodiments, the semi-permanent colorant comprises a combination of two or more of: a compound of Formula I, a compound of Formula IIa, a compound of Formula IIb, and a compound of Formula III.

In some embodiments, the semi-permanent colorant comprises two semi-permanent colorants, e.g., a first semi-permanent colorant and a second semi-permanent colorant. In some embodiments, the semi-permanent colorant can comprise genipin and a genipin derivative or the semi-permanent colorant can comprise two different genipin derivatives (e.g., any two of the genipin derivatives described herein). In some embodiments, the first semi-permanent colorant is genipin and the second semi-permanent colorant is Compound 1. In some embodiments, the first semi-permanent colorant is genipin and the second semi-permanent colorant is Compound 12. In some embodiments, the first semi-permanent colorant is Compound 1 and the second semi-permanent colorant is Compound 12. In some embodiments, the first semi-permanent colorant is genipin and the second semi-permanent colorant is Compound 14. In some embodiments, the first semi-permanent colorant is Compound 1 and the second semi-permanent colorant is Compound 14. In some embodiments, the first semi-permanent colorant is Compound 7 and the second semi-permanent colorant is Compound 9. In some embodiments, the first semi-permanent colorant is Compound 7 and the second semi-permanent colorant is Compound 16. In some embodiments, the first semi-permanent colorant is Compound 9 and the second semi-permanent colorant is Compound 16.

In some embodiments, the first semi-permanent colorant and the second semi-permanent colorant are present at a ratio of about 10:1 to about 1:10 first semi-permanent colorant:second semi-permanent colorant. In some embodiments, about 1:10 to 10:1, about 2:10 to 10:2, about 3:10 to 10:3, about 4:10 to 10:4, about 6:10 to 10:6, about 7:10 to 10:7, about 8:10 to 10:8, or about 9:10 to 10:9. In some embodiments, about 1:8 to 8:1, about 3:8 to 8:3, about 5:8 to 8:5, or about 7:8 to 8:7. In some embodiments, about 1:4 to about 1:3, about 1:4 to about 1:2, about 1:4 to about 1:1, about 1:4 to about 2:1, about 1:4 to about 3:1, about 3:1 to about 4:1, about 3:4 to about 4:3, about 2:1 to about 4:1, about 1:1 to about 4:1, about 1:2 to about 4:1, or about 1:3 to about 4:1 first semi-permanent colorant:second semipermanent colorant. In some embodiments, the first semi-permanent colorant and the second semi-permanent colorant are present at a ratio of about 1:4, about 1:3, about 1:2, about 1:1, about 2:1, about 1:1, about 2:1, about 3:1, or about 4:1 first semi-permanent colorant:second semi-permanent colorant. In some embodiments, the first semi-permanent colorant and the second semi-permanent colorant are present at a ratio of about 1:1 first semi-permanent colorant:second semi-permanent colorant.

In some embodiments, the semi-permanent colorant comprises three semi-permanent colorants, e.g., a first semi-permanent colorant, a second semi-permanent colorant, and a third semi-permanent colorant. In some embodiments, the semi-permanent colorant can comprise genipin and two different genipin derivatives or the semi-permanent colorant can comprise three different genipin derivatives (e.g., any three of the genipin derivatives described herein). In some embodiments, the first semi-permanent colorant is genipin, the second semi-permanent colorant is Compound 1, and the third semi-permanent colorant is Compound 12. In some embodiments, the first semi-permanent colorant is genipin, the second semi-permanent colorant is Compound 1, and the third semi-permanent colorant is Compound 14. In some embodiments, the first semi-permanent colorant is Compound 7, the second semi-permanent colorant is Compound 9, and the third semi-permanent colorant is Compound 16.

In some embodiments, the first semi-permanent colorant, the second semi-permanent colorant, and the third semi-permanent colorant are present at a ratio of about 1:4:1 to about 4:1:1 first semi-permanent colorant:second semi-permanent colorant:third semi-permanent colorant. In some embodiments, about 1:4:1 to about 1:3:1, about 1:4:1 to about 1:2:1, about 1:4:1 to about 1:1:1, about 1:4:1 to about 2:1:1, about 1:4:1 to about 3:1:1, about 3:1:1 to about 4:1:1, about 2:1:1 to about 4:1:1, about 1:1:1 to about 4:1:1, about 1:2:1 to about 4:1:1, or about 1:3:1 to about 4:1:1 first semi-permanent colorant:second semi-permanent colorant: third semi-permanent colorant. In some embodiments, the first semi-permanent colorant, the second semi-permanent colorant, and the third semi-permanent colorant are present at a ratio of about 1:4:1, about 1:3:1, about 1:2:1, about 1:1:1, about 2:1:1, about 1:1:1, about 2:1:1, about 3:1:1, or about 4:1:1 first semi-permanent colorant:second semi-permanent colorant:third semi-permanent colorant. In some embodiments, the first semi-permanent colorant, the second semi-permanent colorant, and the third semi-permanent colorant are present at a ratio of about 1:1:1 first semi-permanent colorant:second semi-permanent colorant:third semi-permanent colorant.

In some embodiments, the semi-permanent colorant (e.g., a genipin derivative, lawsone, a lawsone derivative, or a combination thereof, e.g., any of the combinations described herein) is present in an amount of about 0.1% to about 25% w/w of the composition. In some embodiments, about 0.1% to about 24%, about 0.1% to about 22%, about 0.1% to about 20%, about 0.1% to about 18%, about 0.1% to about 16%, about 0.1% to about 14%, about 0.1% to about 12%, about 0.1% to about 10%, about 0.1% to about 8%, about 0.1% to about 6%, about 0.1% to about 4%, about 0.1% to about 2%, about 24% to about 25%, about 22% to about 25%, about 20% to about 25%, about 18% to about 25%, about 16% to about 25%, about 14% to about 25%, about 12% to about 25%, about 10% to about 25%, about 8% to about 25%, about 6% to about 25%, about 4% to about 25%, or about 2% to about 25% w/w of the composition. In some embodiments, the semi-permanent colorant is present in an amount of about 0.1% to about 3%, about 0.1% to about 1%, about 0.5% to about 1%, about 0.5% to about 1.5%, or about 0.5% to about 3% w/w of the composition. In some embodiments, the semi-permanent colorant is present in an amount of about 0.5% to about 1.5% w/w of the composition. In some embodiments, the semi-permanent colorant is present in an amount of about 5% to about 15%, about 10% to about 15%, about 10% to about 20%, about 15% to about 20%, about 8% to about 12%, about 10% to about 14%, about 12% to about 16%, about 14% to about 18%, or about 16% to about 20% w/w of the composition. In some embodiments, the semi-permanent colorant is present in an amount of about 12% to about 16% w/w of the composition. In some embodiments, the semi-permanent colorant is present in an amount of about 9% to about 11% w/w of the composition. In some embodiments, the semi-permanent colorant is present in an amount of about 0.5%, about 0.9%, about 1%, about 2%, about 3%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 15%, about 16%, about 17%, about 18%, about 19%, about 20%, about 21%, about 22%, about 23%, about 24%, or about 25% w/w of the composition. In some embodiments, the semi-permanent colorant is present in an amount of about 14% w/w of the composition. In some embodiments, the semi-permanent colorant is present in an amount of about 10% w/w of the composition. In some embodiments, the semi-permanent colorant comprises a genipin derivative, lawsone, a lawsone derivative, or a combination thereof.

Non-limiting examples of solvents include water, methanol, ethanol, isopropanol, and diethylene glycol monoethyl ether. In some embodiments, the solvent is a volatile solvent, e.g., the solvent can evaporate or vaporize at room temperature. Non-limiting examples of volatile solvents include water, methanol, ethanol, and isopropanol. In some embodiments, the solvent is selected to have a low toxicity profile when used as described herein. In some embodiments, the solvent can be selected such that the amount of any residual solvent left after a composition (e.g., a composition described herein) has dried on an applicator is not a toxic amount for contact with a human skin surface.

In some embodiments, the solvent (e.g., any of the solvents described herein) is present in an amount of about 1% to about 95% w/w of the composition. In some embodiments, about 10% to about 95%, about 20% to about 95%, about 30% to about 95%, about 40% to about 95%, about 50% to about 95%, about 60% to about 95%, about 70% to about 95%, about 80% to about 95%, about 1% to about 20%, about 1% to about 30%, about 1% to about 40%, about 1% to about 50%, about 1% to about 60%, about 1% to about 70%, about 1% to about 80%, or about 1% to about 90% w/w of the composition. In some embodiments, the solvent is present in an amount of about 50% to about 75%, about 55% to about 80%, about 60% to about 85%, about 65% to about 90%, about 55% to about 75%, about 60% to about 80%, about 65% to about 85%, about 70% to about 90%, about 75% to about 95%, about 60% to about 70%, about 65% to about 75%, about 70% to about 80%, or about 75% to about 85% w/w of the composition. In some embodiments, about 60% to about 65%, about 62% to about 67%, about 65% to about 70%, about 68% to about 72%, about 70% to about 75%, about 72% to about 76%, about 75% to about 80%, about 77% to about 82%, about 80% to about 85%, about 82% to about 87%, about 85% to about 90%, about 87% to about 92%, or about 90% to about 95% w/w of the composition. In some embodiments, the solvent is present in an amount of about 80% to about 90% w/w of the composition.

In some embodiments, the solvent is present in an amount of about 76% to about 79% w/w of the composition. In some embodiments, the solvent is present in an amount of about 77% to about 78% w/w of the composition. In some embodiments, the solvent is present in an amount of about 72% to about 76% w/w of the composition. In some embodiments, the solvent is present in an amount of about 69% to about 71% w/w of the composition. In some embodiments, the solvent is present in an amount of about 70% to about 71% w/w of the composition. In some embodiments, the solvent is present in an amount of about 50%, about 55%, about 60%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or about 95% w/w of the composition. In some embodiments, the solvent is present in an amount of about 74% w/w of the composition. In some embodiments, the solvent is present in an amount of about 77% w/w of the composition. In some embodiments, the solvent is present in an amount of about 71% w/w of the composition. In some embodiments, the solvent is present in an amount of about 86% w/w of the composition.

In some embodiments, the solvent is a combination of two or more solvents, e.g., two or more of water, methanol, ethanol, isopropanol, and diethylene glycol monoethyl ether. In some embodiments, each solvent is independently present in an amount of about 5% to about 80% w/w of the composition. In some embodiments, each solvent can be independently present in an amount of about 5% to about 10%, about 5% to about 20%, about 5% to about 30%, about 5% to about 40%, about 5% to about 50%, about 5% to about 60%, about 5% to about 70%, about 70% to about 80%, about 60% to about 80%, about 50% to about 80%, about 40% to about 80%, about 30% to about 80%, about 20% to about 80%, or about 10% to about 80% w/w of the composition. In some embodiments, the solvent is independently present in an amount of 10% to about 20%, about 15% to about 25%, about 20% to about 30%, about 25% to about 35%, about 30% to about 40%, about 35% to about 45%, about 40% to about 50%, about 45% to about 50%, about 50% to about 60%, or about 65% to about 75% w/w of the composition. In some embodiments, each solvent can be independently present in an amount of about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 60%, about 65%, about 70%, or about 72%, w/w of the composition.

In some embodiments, the solvent is a combination of water and ethanol. In some embodiments, the water is present in an amount of about 15% to about 40% w/w of the composition and the ethanol is present in an amount of about 30% to about 55% w/w of the composition. In some embodiments, the water is present in an amount of about 20% to about 30%, about 25% to about 35%, about 25% to about 30%, or about 28% to about 32% w/w of the composition and the ethanol is present in an amount of about 35% to about 45%, about 40% to about 50%, about 40% to about 55%, about 45% to about 55%, about 45% to about 50%, about 40% to about 45%, about 42% to about 47%, or about 45% to about 50% w/w of the composition. In some embodiments, the water is present in an amount of about 25% to about 30% w/w of the composition and the ethanol is present in an amount of about 40% to about 50% w/w of the composition. In some embodiments, the water is present in an amount of about 28% to about 32% w/w of the composition and the ethanol is present in an amount of about 45% to about 50% w/w of the composition. In some embodiments, the water is present in an amount of about 15% to about 25%, about 18% to about 22%, or about 19% to about 21% w/w of the composition and the ethanol is present in an amount of about 45% to about 55%, about 48% to about 52%, or about 49% to about 51% w/w of the composition. In some embodiments, the water is present in an amount of about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35%, w/w of the composition and the ethanol is present in an amount of about 40%, about 41%, about 42%, about 43%, about 44%, about 45%, about 46%, about 47%, about 48%, about 49%, about 50%, about 51%, about 52%, about 53%, about 54%, or about 55% w/w of the composition. In some embodiments, the water is present in an amount of about 28% w/w of the composition and the ethanol is present in an amount of about 46% w/w of the composition.

In some embodiments, the water is present in an amount of about 65% to about 75% w/w of the composition and the ethanol is present in an amount of about 10% to about 20% w/w of the composition. In some embodiments, the water is present in an amount of about 72% w/w of the composition and the ethanol is present in an amount of about 14% w/w of the composition. In some embodiments, the water is present in an amount of about 30% w/w of the composition and the ethanol is present in an amount of about 48% w/w of the composition. In some embodiments, the water is present in an amount of about 21% w/w of the composition and the ethanol is present in an amount of about 50% w/w of the composition.

As used herein, a "thickening agent" refers to an agent that increases the viscosity of a liquid. In some embodiments, the thickening agent increases the viscosity of the liquid without substantially changing other properties of the liquid. Non-limiting examples of thickening agents include starches, gums (e.g., natural and synthetic gums), cellulosics, and arabinogalactan. Non-limiting examples of starches include aluminum starch octenylsuccinate. Non-limiting examples of gums include xanthan gum, sclerotium gum, tragacanth gum, pectin, gum karaya, gum arabic, agar, guar gum, carrageenan, locust bean gum, alginate, alginin, gelatin, tara gum, gum ghatti, gellan gum, konjac gum, cassia gum, spruce gum, chicle gum, dammar, curdlan gum, and pullulan. Non-limiting examples of cellulosics include hydroxyethylcellulose, hydroxypropyl cellulose, hydroxypropyl methylcellulose, ethylcellulose, soybean hemicellulose, and sodium carboxy methylcellulose.

In some embodiments, the thickening agent is present in an amount of about 0.1% to about 10% w/w of the composition. In some embodiments, about 0.1% to about 8%, about 0.1% to about 6%, about 0.1% to about 5%, about 0.1% to about 4%, about 0.1% to about 3%, about 0.1% to about 2%, about 0.1% to about 1%, about 8% to about 10%, about 6% to about 10%, about 4% to about 10%, about 3% to about 10%, about 2% to about 10%, or about 1% to about 10% w/w of the composition. In some embodiments, the thickening agent is present in an amount of about 1% to about 5% w/w of the composition. In some embodiments, the thickening agent is present in an amount of about 0.25%, about 0.5%, about 1%, about 1.5%, about 2%, about 2.5%, about 3%, about 3.5%, about 4%, about 4.5%, about 5%, about 5.5%, about 6%, about 7%, about 8%, about 9%, or about 10% w/w of the composition. In some embodiments, the thickening agent is present in an amount of about 4% w/w of the composition.

In some embodiments, the thickening agent is present in an amount of about 0.01% to about 1% w/w of the composition. In some embodiments about 0.01% to about 0.05%, about 0.01% to about 0.1%, about 0.01% to about 0.15%, about 0.01% to about 0.2%, about 0.01% to about 0.3%, about 0.01% to about 0.4%, about 0.01% to about 0.5%, about 0.01% to about 0.6%, about 0.01% to about 0.7%, about 0.01% to about 0.8%, about 0.01% to about 0.9%, about 0.9% to about 1%, about 0.8% to about 1%, about 0.7% to about 1%, about 0.6% to about 1%, about 0.5% to about 1%, about 0.4% to about 1%, about 0.3% to about 1%, about 0.2% to about 1%, about 0.15% to about 1%, about 0.1% to about 1%, or about 0.05% to about 1% w/w of the composition. In some embodiments, the thickening agent is present in an amount of about 0.05% to about 0.25%, about 0.05% to about 0.2%, about 0.1% to about 0.2%, or about 0.1% to about 0.15% w/w of the composition. In some embodiments, the thickening agent is present in an amount of about 0.05% to about 0.2% w/w of the composition. In some embodiments, the thickening agent is present in an amount of about 0.01%, about 0.05%, 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.2%, about 0.22%, about 0.24%, about 0.26%, about 0.28%, about 0.3%, about 0.4%, about 0.5%, about 0.6%, about 0.8%, about 0.9% or about 1% w/w of the composition. In some embodiments, the thickening agent is present in an amount of about 0.12% w/w of the composition.

In some embodiments, the thickening agent is xanthan gum. In some embodiments, the xanthan gum is present in an amount of about 0.1% to about 10% w/w of the composition. In some embodiments, about 0.1% to about 8%, about 0.1% to about 6%, about 0.1% to about 5%, about 0.1% to about 4%, about 0.1% to about 3%, about 0.1% to about 2%, about 0.1% to about 1%, about 8% to about 10%, about 6% to about 10%, about 4% to about 10%, about 3% to about 10%, about 2% to about 10%, or about 1% to about 10% w/w of the composition. In some embodiments, the xanthan gum is present in an amount of about 1% to about 5% w/w of the composition. In some embodiments, the xanthan gum is present in an amount of about 0.25%, about 0.5%, about 1%, about 1.5%, about 2%, about 2.5%, about 3%, about 3.5%, about 4%, about 4.5%, about 5%, about 5.5%, about 6%, about 7%, about 8%, about 9%, or about 10% w/w of the composition. In some embodiments, the xanthan gum is present in an amount of about 4% w/w of the composition.

In some embodiments, the thickening agent is a combination of two or more thickening agents, e.g., two or more of arabinogalactan, aluminum starch octenylsuccinate, xanthan gum, sclerotium gum, tragacanth gum, pectin, gum karaya, gum arabic, agar, guar gum, carrageenan, locust bean gum, alginate, alginin, gelatin, tara gum, gum ghatti, gellan gum, konjac gum, cassia gum, spruce gum, chicle gum, dammar, curdlan gum, pullulan, hydroxyethylcellulose, hydroxypropyl cellulose, hydroxypropyl methylcellulose, ethylcellulose, soybean hemicellulose, and sodium carboxy methylcellulose. In some embodiments, each thickening agent is independently present in an amount of about 0.01% to about 0.5% w/w of the composition In some embodiments, each thickening agent can be independently present in an amount of about 0.01% to about 0.05%, about 0.01% to about 0.1%, about 0.01% to about 0.15%, about 0.01% to about 0.2%, about 0.01% to about 0.25%, about 0.01% to about 0.3%, about 0.01% to about 0.35% w/w of the composition. about 0.01% to about 0.4%, about 0.01% to about 0.45%, about 0.45% to about 0.5%, about 0.4% to about 0.5%, about 0.35% to about 0.5%, about 0.3% to about 0.5%, about 0.25% to about 0.5%, about 0.2% to about 0.5%, about 0.15% to about 0.5%, about 0.1% to about 0.15%, or about 0.05% to about 0.15% w/w of the composition. In some embodiments, each thickening agent is independently present in an amount of about 0.01% to about 0.04%, about 0.02% to about 0.06%, about 0.03% to about 0.07%, 0.04% to about 0.08%, about 0.06% to about 0.1%, or about 0.08% to about 0.12%, or about 0.1% to about 0.14% w/w of the composition. In some embodiments, each thickening agent can be independently present in an amount of about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.22%, about 0.24%, about 0.26%, about 0.28%, about 0.3%, about 0.4%, about 0.5%, about 0.6%, about 0.8%, about 0.9% or about 1% w/w of the composition.

In some embodiments, the thickening agent is a combination of hydroxyethylcellulose and xanthan gum. In some embodiments, the hydroxyethylcellulose is present in an amount of about 0.01% to about 0.5% w/w of the composition and xanthan gum is present in an amount of about 0.01% to about 0.5% w/w of the composition. In some embodiments, the hydroxyethylcellulose is present in an amount of about 0.01% to about 0.04%, about 0.02% to about 0.06%, about 0.03% to about 0.07%, 0.04% to about 0.08%, about 0.06% to about 0.1%, or about 0.08% to about 0.12%, or about 0.1% to about 0.14% w/w of the composition and xanthan gum is present in an amount of about 0.01% to about 0.04%, about 0.02% to about 0.06%, about 0.03% to about 0.07%, 0.04% to about 0.08%, about 0.06% to about 0.1%, or about 0.08% to about 0.12%, or about 0.1% to about 0.14% w/w of the composition. In some embodiments, the hydroxyethylcellulose is present in an amount of about 0.04% to about 0.08% w/w of the composition and xanthan gum is present in an amount of about 0.04% to about 0.08% w/w of the composition. In some embodiments, the hydroxyethylcellulose is present in an amount of about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, or about 0.2% w/w of the composition and xanthan gum is present in an amount of about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, or about 0.2% w/w of the composition. In some embodiments, the hydroxyethylcellulose is present in an amount of about 0.06% w/w of the composition and the xanthan gum is present in an amount of about 0.06% w/w of the composition.

A "humectant" as used herein refers to a substance that attracts water. In some embodiments, a humectant may attract water to bring moisture to the skin. Non-limiting examples of humectants include polyhydric alcohols, for example, polyalkylene glycols (e.g., alkylene polyols and their derivatives), alpha hydroxy acids, sugars, Aloe vera gel, vegetable oil, lithium chloride, allantoin, urea, and dicyanamide. Non-limiting examples of polyhydric alcohols include glycerol, lactic acid, propylene glycol, propanediol, polyethylene glycol, dipropylene glycol, polypropylene glycol, polyethylene glycol and derivatives thereof, hexylene glycol, 1,3-butylene glycol, 1,2,6-hexanetriol, ethoxylated glycerol, propoxylated glycerol, glyceryl triacetate, sorbitol, hydroxypropyl sorbitol, xylitol, maltitol, hyaluronic acid, Tremella extract, sodium lactate, sodium L-pyroglutamate urea, and pyrrolidone carboxylic acid.

In some embodiments, the humectant is present in an amount of about 0.1% to about 20% w/w of the composition. In some embodiments, about 0.1% to about 1%, about 0.1% to about 5%, about 0.1% to about 10%, about 0.1% to about 15%, about 15% to about 20%, about 10% to about 20%, about 5% to about 20%, or about 1% to about 20% w/w of the composition. In some embodiments, the humectant is present in an amount of about 0.5% to about 2%, about 0.5% to about 5%, about 1% to about 10%, about 1% to about 5%, about 2% to about 7%, about 5% to about 10%, about 7% to about 12%, or about 10% to about 15% w/w of the composition. In some embodiments, the humectant is present in an amount of about 0.5% to about 1.5% w/w of the composition. In some embodiments, the humectant is present in an amount of about 2% to about 6% w/w of the composition. In some embodiments, the humectant is present in an amount of about 0.1%, about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, or about 20% w/w of the composition. In some embodiments, the humectant is present in an amount of about 4% w/w of the composition. In some embodiments, the humectant is present in an amount of about 1% w/w of the composition.

In some embodiments, the humectant is propanediol. In some embodiments, the propanediol is present in an amount of about 0.1% to about 20% w/w of the composition. In some embodiments, about 0.1% to about 1%, about 0.1% to about 5%, about 0.1% to about 10%, about 0.1% to about 15%, about 15% to about 20%, about 10% to about 20%, about 5% to about 20%, or about 1% to about 20% w/w of the composition. In some embodiments, the propanediol is present in an amount of about 0.5% to about 2%, about 0.5% to about 5%, about 1% to about 10%, about 1% to about 5%, about 2% to about 7%, about 5% to about 10%, about 7% to about 12%, or about 10% to about 15% w/w of the composition. In some embodiments, the propanediol is present in an amount of about 0.5% to about 1.5% w/w of the composition. In some embodiments, the propanediol is present in an amount of about 2% to about 6% w/w of the composition. In some embodiments, the propanediol is present in an amount of about 0.1%, about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, or about 20% w/w of the composition. In some embodiments, the propanediol is present in an amount of about 4% w/w of the composition. In some embodiments, the propanediol is present in an amount of about 1% w/w of the composition.

In some embodiments, the humectant is glycerin. In some embodiments, the glycerin is present in an amount of about 0.1% to about 20% w/w of the composition. In some embodiments, about 0.1% to about 1%, about 0.1% to about 5%, about 0.1% to about 10%, about 0.1% to about 15%, about 15% to about 20%, about 10% to about 20%, about 5% to about 20%, or about 1% to about 20% w/w of the composition. In some embodiments, the glycerin is present in an amount of about 1% to about 10%, about 1% to about 5%, about 2% to about 7%, about 5% to about 10%, about 7% to about 12%, or about 10% to about 15% w/w of the composition. In some embodiments, the glycerol is present in an amount of about 2% to about 6% w/w of the composition. In some embodiments, the glycerol is present in an amount of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, or about 20% w/w of the composition. In some embodiments, the glycerol is present in an amount of about 4% w/w of the composition.

In some embodiments, the humectant is vegetable oil. In some embodiments, the vegetable oil is present in an amount of about 0.1% to about 20% w/w of the composition. In some embodiments, about 0.1% to about 1%, about 0.1% to about 5%, about 0.1% to about 10%, about 0.1% to about 15%, about 15% to about 20%, about 10% to about 20%, about 5% to about 20%, or about 1% to about 20% w/w of the composition. In some embodiments, the vegetable oil is present in an amount of about 1% to about 10%, about 1% to about 5%, about 2% to about 7%, about 5% to about 10%, about 7% to about 12%, or about 10% to about 15% w/w of the composition. In some embodiments, the vegetable oil is present in an amount of about 7% to about 11% w/w of the composition. In some embodiments, the vegetable oil is present in an amount of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, or about 20% w/w of the composition. In some embodiments, the vegetable oil is present in an amount of about 9% w/w of the composition.

In some embodiments, the composition further includes a film-forming agent. As used herein, a "film-forming agent" refers to a compound that can produce a continuous film on skin. In some embodiments, a film-forming agent is a compound that produces a continuous film on skin upon drying. Non-limiting examples of film-forming agents include volatile silicone resins, polyvinylpyrrolidone, acrylates, acrylamides, copolymers, and isododecane resins. Non-limiting examples of volatile silicone resins include polymethylsilsesquioxane, trimethylsiloxysilicate, polypropylsilsesquioxane, dimethicone, cyclopentasiloxane, dimethiconol crosspolymer, polysilicone-6, polysilicone-8, polysilicone-11, and polysilicone-14. Non-limiting examples of copolymers include acrylates copolymer, styrene/acrylates copolymer, acrylates/C12-22 alkyl methacrylate copolymer, acrylates/polytrimethylsiloxymethacrylate copolymer, polyvinylpyrrolidone/vinyl acetate (VP/VA) copolymer, VP/dimethiconylacrylate/polycarbamyl/polyglycol ester, VP/dimethylaminoethylmethacrylate copolymer, VP/dimethylamino ethylmethacrylate/polycarbamyl polyglycol ester, VP/eicosene copolymer, VP/hexadecene copolymer, VP/methacrylamide/vinyl imidazole copolymer, VP/polycarbamyl polyglycol ester, VP/VA copolymer, polyester-1, polyester-2, polyester-3, polyester-4, polyester-5, polyester-7, polyester-8, and polyester-10.

In some embodiments, the film-forming agent is present in an amount of about 0.1% to about 20% w/w of the composition. In some embodiments, about 0.1% to about 1%, about 0.1% to about 5%, about 0.1% to about 10%, about 0.1% to about 15%, about 15% to about 20%, about 10% to about 20%, about 5% to about 20%, or about 1% to about 20% w/w of the composition. In some embodiments, the film-forming agent is present in an amount of about 1% to about 10%, about 1% to about 5%, about 2% to about 7%, about 5% to about 10%, about 7% to about 12%, or about 10% to about 15% w/w of the composition. In some embodiments, the film-forming agent is present in an amount of about 4% to about 6% w/w of the composition. In some embodiments, the film-forming agent is present in an amount of about 6% to about 9% w/w of the composition. In some embodiments, the film-forming agent is present in an amount of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, or about 20% w/w of the composition. In some embodiments, the film-forming agent is present in an amount of about 5% w/w of the composition. In some embodiments, the film-forming agent is present in an amount of about 7.5% w/w of the composition.

In some embodiments, the film-forming agent is a combination of two or more film-forming agents. In some embodiments, two or more of polymethylsilsesquioxane, trimethylsiloxysilicate, polypropylsilsesquioxane, dimethicone, cyclopentasiloxane, dimethiconol crosspolymer, polysilicone-6, polysilicone-8, polysilicone-11, polysilicone-14, acrylates copolymer, styrene/acrylates copolymer, polyvinylpyrrolidone, acrylates/C12-22 alkyl methacrylate copolymer, acrylates/polytrimethylsiloxymethacrylate copolymer, polyvinylpyrrolidone/vinyl acetate (VP/VA) copolymer, VP/dimethiconylacrylate/polycarbamyl/polyglycol ester, VP/dimethylaminoethylmethacrylate copolymer, VP/dimethylamino ethylmethacrylate/polycarbamyl polyglycol ester, VP/eicosene copolymer, VP/hexadecene copolymer, VP/methacrylamide/vinyl imidazole copolymer, VP/polycarbamyl polyglycol ester, VP/VA copolymer, polyester-1, polyester-2, polyester-3, polyester-4, polyester-5, polyester-7, polyester-8, and polyester-10. In some embodiments, each film-forming agent is independently present in an amount of about 0.1% to about 15% w/w of the composition. In some embodiments, about 0.1% to about 1%, about 0.1% to about 5%, about 0.1% to about 10%, about 10% to about 15%, about 5% to about 15%, or about 1% to about 15% w/w of the composition. In some embodiments, each film-forming agent is present in an amount of about 0.1% to about 2%, about 0.5% to about 2%, about 1% to about 10%, about 1% to about 5%, about 2% to about 7%, about 5% to about 10%, about 7% to about 12%, or about 10% to about 15% w/w of the composition. In some embodiments, the film-forming agent is present in an amount of about 1% to about 10%, about 1% to about 5%, about 2% to about 7%, about 5% to about 10%, about 7% to about 12%, or about 10% to about 15% w/w of the composition. In some embodiments, about 0.1%, about 0.25%, about 0.5%, about 0.75%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, or about 20% w/w of the composition.

In some embodiments, the film-forming agent is a combination of polymethylsilsesquioxane and acrylates/C12-22 alkyl methacrylate copolymer. In some embodiments, the polymethylsilsesquioxane is present in an amount of about 0.5% to about 10% w/w of the composition and the acrylates/C12-22 alkyl methacrylate copolymer is present in an amount of about 0.5% to about 10% w/w of the composition. In some embodiments, the polymethylsilsesquioxane is present in an amount of about 0.05% to about 1%, about 0.05% to about 5%, about 0.05% to about 8%, about 8% to about 10%, about 5% to about 10%, about 1% to about 10%, or about 1% to about 5% w/w of the composition and the acrylates/C12-22 alkyl methacrylate copolymer is present in an amount of about 0.05% to about 1%, about 0.05% to about 5%, about 0.05% to about 8%, about 8% to about 10%, about 5% to about 10%, about 1% to about 10%, or about 1% to about 5% w/w of the composition. In some embodiments, the polymethylsilsesquioxane is present in an amount of about 1% to about 5% w/w of the composition and the acrylates/C12-22 alkyl methacrylate copolymer is present in an amount of about 1% to about 5% w/w of the composition. In some embodiments, the polymethylsilsesquioxane is present in an amount of about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% w/w of the composition and the acrylates/C12-22 alkyl methacrylate copolymer is present in an amount of about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% w/w of the composition. In some embodiments, the polymethylsilsesquioxane is present in an amount of about 2% w/w of the composition and the acrylates/C12-22 alkyl methacrylate copolymer is present in an amount of about 3% w/w of the composition.

In some embodiments, the film-forming agent is a combination of acrylates copolymer, polyvinylpyrrolidone, and styrene/acrylates copolymer. In some embodiments, the acrylates copolymer is present in an amount of about 0.1% to about 10% w/w of the composition; the polyvinylpyrrolidone is present in an amount of about 0.1% to about 10% w/w of the composition; and the styrene/acrylates copolymer is present in an amount of about 0.1% to about 10% w/w of the composition. In some embodiments, the acrylates copolymer is present in an amount of about 0.1% to about 1%, about 0.1% to about 5%, about 0.1% to about 8%, about 8% to about 10%, about 5% to about 10%, or about 1% to about 10% w/w of the composition; the polyvinylpyrrolidone is present in an amount of about 0.1% to about 1%, about 0.1% to about 5%, about 0.1% to about 8%, about 8% to about 10%, about 5% to about 10%, or about 1% to about 10% w/w of the composition; and the styrene/acrylates copolymer is present in an amount of about 0.1% to about 1%, about 0.1% to about 5%, about 0.1% to about 8%, about 8% to about 10%, about 5% to about 10%, or about 1% to about 10% w/w of the composition. In some embodiments, the acrylates copolymer is present in an amount of about 0.1% to about 1% w/w of the composition; the polyvinylpyrrolidone is present in an amount of about 0.5% to about 1.5% w/w of the composition; and the styrene/acrylates copolymer is present in an amount of about 5% to about 7% w/w of the composition. In some embodiments, the acrylates copolymer is present in an amount of about 0.1%, about 0.25%, about 0.5%, about 1%, about 1.5%, about 2%, about 2.5%, about 3%, about 3.5%, about 4%, about 4.5%, or about 5% w/w of the composition; the polyvinylpyrrolidone is present in an amount of about 0.25%, about 0.5%, about 1%, about 1.5%, about 2%, about 2.5%, about 3%, about 3.5%, about 4%, about 4.5%, about 5%, about 5.5%, or about 6% w/w of the composition; and the styrene/acrylates copolymer is present in an amount of about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% w/w of the composition. In some embodiments, the acrylates copolymer is present in an amount of about 0.25% w/w of the composition; the polyvinylpyrrolidone is present in an amount of about 1% w/w of the composition; and the styrene/acrylates copolymer is present in an amount of about 6% w/w of the composition.

In some embodiments, the composition can further include an amine. Non-limiting examples of amines include: arginine, alanine, asparagine, aspartic acid, cysteine, glutamic acid, glutamine, glycine, histidine, isoleucine, leucine, lysine, methionine, phenylalanine, proline, serine, threonine, tryptophan, tyrosine, valine, b-aminolevulinic acid, 4-aminobenzoic acid, and γ-aminobutyric acid.

In some embodiments, the amine is present in an amount of about 0.01% to about 1% w/w of the composition. In some embodiments, about 0.01% to about 0.05%, about 0.01% to about 0.1%, about 0.01% to about 0.5%, about 0.5% to about 1%, about 0.1% to about 1%, about 0.05% to about 1%, or about 0.1% to about 1% w/w of the composition. In some embodiments, the amine is present in an amount of about 0.02% w/w of the composition.

In some embodiments, the composition can further include a temporary colorant. In some embodiments, the temporary colorant can be used to show what the semi-permanent tattoo will look like, outline the location of the semi-permanent tattoo on an applicator, provide a logo, e.g., a brand logo, that does not transfer to the skin or transfers but is present for a short time as compared to the duration of the semi-permanent tattoo. In some embodiments, the temporary colorant can be used to provide a changing semi-permanent tattoo that changes appearance with time, e.g., with semi-permanent colorant duration and temporary colorant duration. Non-limiting examples of temporary colorants include iron oxide black ($Fe_3O_4$), iron oxide (FeO), carbon, logwood, ochre, cinnabar (HgS), cadmium red (CdSe), iron (III) oxide ($Fe_2O_3$), naphthol-AS pigment, disazodiarylide, disazopyrazolone, cadmium seleno-sulfide, cadmium yellow (CdS, CdZnS), curcuma yellow, chrome yellow ($PbCrO_4$), disazodiarylide, chromium oxide ($Cr_2O_3$), malachite [$Cu_2(CO_3)(OH)_2$], a ferrocyanide, a ferricyanide, lead chromate, monoazo pigment, Cu/Al phthalocyanine, Cu phthalocyanine, azure blue, cobalt blue, Cu-phthalocyanine, manganese violet (manganese ammonium pyrophosphate), an aluminum salt, quinacridone, dioxazine/carbazole, lead white (lead carbonate), titanium dioxide ($TiO_2$), barium sulfate ($BaSO_4$), zinc oxide, anthraquinone dyes and derivatives, annatto, caramel, β-carotene, bismuth citrate, disodium EDTA copper, potassium sodium copper chlorophyllin, dihydroxyacetone, bismuth oxychloride, guaiazulene, henna, ferric ammonium ferrocyanide, ferric ferrocyanide, chromium hydroxide green, chromium oxide greens, guanine, lead acetate, pyrophillite, mica, silver, titanium dioxide, aluminum powder, bronze powder, copper powder, ultramarines, manganese violet, zinc oxide, luminescent zinc sulfide, D&C Black Nos. 2 and 3, FD&C Blue No. 1 (e.g., acid blue 9), D&C Blue No. 4, D&C Brown No. 1, FD&C Green No. 3, D&C Green Nos. 5, 6, and 8, D&C Orange Nos. 4, 5, 10 and 11, FD&C Red Nos. 4, D&C Red Nos. 6, 7, 17, 21, 22, 27, 28, 30, 32, 33, 34, 36 and 40, D&C Violet No. 2, Ext. D&C Violet No. 2, FD&C Yellow Nos. 5 and 6, D&C Yellow Nos. 7, 8, 10 and 11, and Ext. D&C Yellow No. 7. In some embodiments, the temporary colorant does not contain an amine group. In some embodiments, the temporary colorant is ultramarine blue.

In some embodiments, the temporary colorant is present in an amount of less than about 0.01% w/w of the composition. In some embodiments, the temporary colorant is present in an amount of about 0.001% to about 0.01% w/w of the composition.

In some embodiments, the composition can further include a preservative. "Preservative" as used herein refers to an agent that protects against decay, discoloration, and/or spoilage. Non-limiting examples of a preservative include ascorbic acid, an ascorbate, a palmitate, citric acid, a benzoate, a benzoic acid, a propionate, propionic acid, a sorbate, sorbic acid, a salicylic acid, a salicylate, hexa-2,4-dienoic acid, a hexa-2,4-dienoate, formaldehyde, a formaldehyde releaser, formic acid and its salts, 3-acetyl-6-methylpyran-2,4-(3H)-dione and its salts, 3,3'-dibromo-4,4'-hexamethylenedioxydibenzamidine and its salts, thiomersal, phenylmercuric salts, undec-10-enoic acid and its salts, 1,3-bis(2-ethylhexyl) hexahydro-5-methyl-5-pyrimidine, 5-bromo-5-nitro-1,3-dioxane, bronopol, 2,4-dichlorobenzyl alcohol, 1-(4-chlorophenyl)-3-(3,4-dichlorophenyl) urea, chlorocresol, chloroxylenol, 5-chloro-2-(2,4-dichlorophenoxy) phenol, N,N"-methylenebis[N'-[3-(hydroxymethyl)-2,5-dioxoimidazolidin-4-yl]urea], polyaminopropyl biguanide, methenamine, quaternium-15, climbazole, DMDM hydantoin, benzyl alcohol, 1-Hydroxy-4-methyl-6-(2,4,4-trimethylpentyl)-2-pyridon, piroctone olamine, bromochlorophene, o-cymen-5-ol, chlorophene, chloroacetaminde, methylchloroisothiazolinone, methylisothiazolinone, phenoxyisopropanol, chlorhexidine, chlorhexidine diacetate, chlorhexidine digluconate, chlorhexidine dihydrochloride, dimethyl oxazolidine, behentrimonium chloride, cetri-monium bromide, cetrimonium chloride, laurtrimonium bromide, laurtrimonium chloride, steartrimonium bromide, steartrimonium chloride, diazolidinyl urea, hexamidine, hexamidine diisethionate, hexamidine paraben, glutaral, 7-ethylbicyclooxazolidine, chlorphenesin, sodium hydroxymethylglycinate, silver chloride, benzethonium chloride, benzalkonium chloride, benza-lkonium bromide, benzalkonium saccharinate, benzylhemiformal, iodopropynyl butylcarbamate, biphenyl-2-ol and its salts, pyrithionine zinc, an erythorbate, a nitrite, ethylenediaminetetraacetic acid (EDTA), sodium lignosulfonate, butylated hydroxyanisole (BHA), butylated hydroxytoluene (BHT), capryllic acid, dilauryl thiodipropionate, erythorbic acid, gum guaiac, methylparaben, a sulfite, a bisulfite, a metabisulfite, propyl gallatepy, propylparaben, stannous chloride, sulfur dioxide, thiodipropionic acid, an isothiazoline, a paraben, phenoxyethanol, ethylhexylglycerin, a glycol, and a tocopherol.

In some embodiments, the preservative is present in an amount of about 0.05% to about 10% w/w of the composition. In some embodiments, about 0.05% to about 0.1%, about 0.05% to about 0.5%, about 0.05% to about 1%, about 0.05% to about 2%, about 0.05% to about 3%, about 0.05% to about 4%, about 0.05% to about 5%, about 0.05% to about 6%, about 0.05% to about 7%, about 0.05% to about 8%, about 0.05% to about 9%, about 9% to about 10%, about 8% to about 10%, about 7% to about 10%, about 6% to about 10%, about 5% to about 10%, about 4% to about 10%, about 3% to about 10%, about 2% to about 10%, about 1% to about 10%, about 0.5% to about 10%, or about 0.1% to about 10% w/w of the composition. In some embodiments, the preservative is present in an amount of about 1% to about 5% w/w of the composition.

In some embodiments, the preservative is present in an amount of 0.1% to about 2%, 0.5% to about 2.5%, about 1% to about 3%, about 1.5% to about 3.5%, about 2% to about 4%, about 2.5% to about 4.5%, or about 3% to about 5% w/w of the composition. In some embodiments, the preservative is present in an amount of about 0.5% to about 1.5%, about 0.5% to about 1.0%, about 1.5% to about 2%, about 1% to about 2%, about 0.5% to about 2%, or about 0.8% to about 2% w/w of the composition. In some embodiments, about 0.05% to about 0.4%, about 0.05% to about 0.2%, about 0.2% to about 0.5%, about 0.15% to about 0.25%, or about 0.1% to about 0.3% w/w of the composition. In some embodiments, the preservative is present in an amount of about 0.01%, about 0.05%, about 0.1%, about 0.5%, about 1%, about 1.5%, about 2%, about 2.5%, about 3%, about 3.5%, about 4%, about 4.5%, about 5%, about 5.5%, or about 6% w/w of the composition. In some embodiments, the preservatives is present in an amount of about 3% w/w of the composition. In some embodiments, the preservatives is present in an amount of about 1% w/w of the composition.

In some embodiments, the preservative is a combination of two or more preservatives. For example, two or more of ascorbic acid, an ascorbate, a palmitate, citric acid, a benzoate, a benzoic acid, a propionate, propionic acid, a sorbate, sorbic acid, a salicylic acid, a salicylate, hexa-2,4-dienoic acid, a hexa-2,4-dienoate, formaldehyde, a formaldehyde releaser, formic acid and its salts, 3-acetyl-6-methylpyran-2,4-(3H)-dione and its salts, 3,3'-dibromo-4,4'-hexamethylenedioxydibenzamidine and its salts, thiomersal, phenylmercuric salts, undec-10-enoic acid and its salts, 1,3-bis(2-ethylhexyl) hexahydro-5-methyl-5-pyrimidine, 5-bromo-5-nitro-1,3-dioxane, bronopol, 2,4-dichlorobenzyl alcohol, 1-(4-chlorophenyl)-3-(3,4-dichlorophenyl) urea, chlorocresol, chloroxylenol, 5-chloro-2-(2,4-dichlorophenoxy) phenol, N,N''-methylenebis[N'-[3-(hydroxymethyl)-2,5-dioxoimidazolidin-4-yl]urea], polyaminopropyl biguanide, methenamine, quaternium-15, climbazole, DMDM hydantoin, benzyl alcohol, 1-Hydroxy-4-methyl-6-(2,4,4-trimethylpentyl)-2-pyridon, piroctone olamine, bromochlorophene, o-cymen-5-ol, chlorophene, chloroacetaminde, methylchloroisothiazolinone, methylisothiazolinone, phenoxyisopropanol, chlorhexidine, chlorhexidine diacetate, chlorhexidine digluconate, chlorhexidine dihydrochloride, dimethyl oxazolidine, behentrimonium chloride, cetri-monium bromide, cetrimonium chloride, laurtrimonium bromide, laurtrimonium chloride, steartrimonium bromide, steartrimonium chloride, diazolidinyl urea, hexamidine, hexamidine diisethionate, hexamidine paraben, glutaral, 7-ethylbicyclooxazolidine, chlorphenesin, sodium hydroxymethylglycinate, silver chloride, benzethonium chloride, benzalkonium chloride, benza-lkonium bromide, benzalkonium saccharinate, benzylhemiformal, iodopropynyl butylcarbamate, biphenyl-2-ol and its salts, pyrithionine zinc, an erythorbate, a nitrite, ethylenediaminetetraacetic acid (EDTA), sodium lignosulfonate, butylated hydroxyanisole (BHA), butylated hydroxytoluene (BHT), capryllic acid, dilauryl thiodipropionate, erythorbic acid, gum guaiac, methylparaben, a sulfite, a bisulfite, a metabisulfite, propyl gallatepy, propylparaben, stannous chloride, sulfur dioxide, thiodipropionic acid, an isothiazoline, a paraben, phenoxyethanol, ethylhexylglycerin, a glycols, and a tocopherol. In some embodiments, each preservative is independently present in an amount of about 0.01% to about 8% w/w of the composition. In some embodiments, about 0.01% to about 0.05%, about 0.01% to about 0.1%, about 0.01% to about 0.5%, about 0.01% to about 1%, about 0.01% to about 2%, about 0.01% to about 3%, about 0.01% to about 4%, about 0.01% to about 5%, about 0.01% to about 6%, about 0.01% to about 7%, about 7% to about 8%, about 6% to about 8%, about 5% to about 8%, about 4% to about 8%, about 3% to about 8%, about 2% to about 8%, about 1% to about 8%, about 0.5% to about 8%, or about 0.1% to about 8% w/w of the composition. In some embodiments, each preservative is independently present in an amount of about 0.05% to about 8% w/w of the composition. In some embodiments, about 0.05% to about 0.1%, about 0.05% to about 0.5%, about 0.05% to about 1%, about 0.05% to about 2%, about 0.05% to about 3%, about 0.05% to about 4%, about 0.05% to about 5%, about 0.05% to about 6%, about 0.05% to about 7%, about 7% to about 8%, about 6% to about 8%, about 5% to about 8%, about 4% to about 8%, about 3% to about 8%, about 2% to about 8%, about 1% to about 8%, about 0.5% to about 8%, or about 0.1% to about 8% w/w of the composition. In some embodiments, the each preservative is independently present in an amount of about 1% to about 5% w/w of the composition. In some embodiments, each preservative is independently present in an amount of about 0.025% to about 0.1%, about 0.1% to about 2%, 0.5% to about 2.5%, about 1% to about 3%, about 1.5% to about 3.5%, about 2% to about 4%, about 2.5% to about 4.5%, or about 3% to about 5% w/w of the composition. In some embodiments, each preservative is independently present in an amount of about 0.5% to about 1.5%, about 0.5% to about 1.0%, about 1.5% to about 2%, about 1% to about 2%, about 0.5% to about 2%, or about 0.8% to about 2% w/w of the composition. In some embodiments, each preservative is independently present in an amount of about 0.01%, about 0.05%, about 0.1%, about 0.5%, about 1%, about 1.5%, about 2%, about 2.5%, about 3%, about 3.5%, about 4%, about 4.5%, about 5%, about 5.5%, or about 6% w/w of the composition.

In some embodiments, the preservative includes a combination of phenoxyethanol and ethylhexylglycerin. In some embodiments, the preservative further includes 1,2-hexanediol (e.g., the preservative is a combination of phenoxyethanol, ethylhexylglycerin, and 1,2-hexanediol). In some embodiments, the preservative further includes EDTA (e.g., the preservative is a combination of phenoxyethanol, ethylhexylglycerin, and EDTA). In some embodiments, the phenoxyethanol is present in an amount of about 0.1% and 5% w/w of the composition; the ethylhexylglycerin is present in an amount of about 0.01% to about 3% w/w of the composition; and the 1,2-hexanediol is present in an amount of about 0.1% to about 5% w/w of the composition. In some embodiments, the phenoxyethanol is present in an amount of about 0.1% to about 0.5%, about 0.1% to about 1%, about 0.1% to about 2%, about 0.1% to about 3%, about 0.1% to about 4%, about 4% to about 5%, about 3% to about 5%, about 2% to about 5%, about 1% to about 5%, about 0.5% to about 5%, about 0.5% to about 1%, about 0.5% to about 2.5%, about 1% to about 3%, about 1.5% to about 3.5%, about 2% to about 4%, or about 2.5% to about 4.5% w/w of the composition; the ethylhexylglycerin is present in an amount of about 0.01% to about 0.1%, 0.01% to about 0.5%, 0.01% to about 1%, about 0.01% to about 2%, about 2% to about 3%, about 1% to about 3%, about 0.1% to about 3%, about 0.05% to about 3%, about 0.05% to about 0.15%, about 0.05% to about 1%, 0.5% to about 2.5%, about 1% to about 3%, about 1.5% to about 3.5%, about 2% to about 4%, about 2.5% to about 4.5%, or about 3% to about 5% w/w of the composition; and the 1,2-hexanediol is present in an amount of about 0.1% to about 1%, about 0.1% to about 2%, about 0.1% to about 3%, about 0.1% to about 4%, about 4% to about 5%, about 3% to about 5%, about 2% to about 5%, about 1% to about 5%, 0.5% to about 2.5%, about 1% to about 3%, about 1.5% to about 3.5%, about 2% to about 4%, about 2.5% to about 4.5%, or about 3% to about 5% w/w of the composition. In some embodiments, the phenoxyethanol is present in an amount of about 0.5%, about 0.6%, about 0.7%, about 0.8%, about 0.9%, about 1%, about 1.1%, about 1.2%, about 1.3%, about 1.4%, about 1.5%, about 2%, about 2.5%, about 3%, about 3.5%, about 4%, or about 4.5% w/w of the composition; the ethylhexylglycerin is present in an amount of about 0.01%, about 0.05%, about 0.06%, about 0.07%, about 0.08%, about 0.09%, about 0.1%, about 0.12%, about 0.13%, about 0.14%, about 0.15%, about 0.25%, about 0.5%, about 1%, about 1.5%, about 2%, or about 2.5% w/w of the composition; and the 1,2-hexanediol is present in an amount of about 0.5%, about 1%, about 1.5%, about 2%, about 2.5%, about 3%, about 3.5%, about 4%, about 4.5%, about 5%, about 5.5%, or about 6% w/w of the composition.

In some embodiments, the preservative further includes EDTA (e.g., the preservative is a combination of phenoxyethanol, ethylhexylglycerin, and EDTA). In some embodiments, the phenoxyethanol is present in an amount of about 0.1% and 5% w/w of the composition; the ethylhexylglycerin is present in an amount of about 0.01% to about 3% w/w of the composition; and the EDTA is present in an amount of about 0.01% to about 2% w/w of the composition. In some embodiments, the phenoxyethanol is present in an amount of about 0.1% to about 0.5%, about 0.1% to about 1%, about 0.1% to about 2%, about 0.1% to about 3%, about 0.1% to about 4%, about 4% to about 5%, about 3% to about 5%, about 2% to about 5%, about 1% to about 5%, about 0.5% to about 5%, about 0.5% to about 1%, about 0.5% to about 2.5%, about 1% to about 3%, about 1.5% to about 3.5%, about 2% to about 4%, or about 2.5% to about 4.5% w/w of the composition; the ethylhexylglycerin is present in an amount of about 0.01% to about 0.1%, 0.01% to about 0.5%, 0.01% to about 1%, about 0.01% to about 2%, about 2% to about 3%, about 1% to about 3%, about 0.1% to about 3%, about 0.05% to about 3%, about 0.05% to about 0.15%, about 0.05% to about 1%, 0.5% to about 2.5%, about 1% to about 3%, about 1.5% to about 3.5%, about 2% to about 4%, about 2.5% to about 4.5%, or about 3% to about 5% w/w of the composition; and the EDTA is present in an amount of about 0.01% to about 0.05%, about 0.01% to about 0.1%, about 0.01% to about 0.5%, about 0.01% to about 1%, about 0.1% to about 1.5%, about 1.5% to about 2%, about 1% to about 2%, about 0.5% to about 2%, about 0.1% to about 2%, or about 0.05% to about 2% w/w of the composition. In some embodiments, the phenoxyethanol is present in an amount of about 0.5%, about 0.6%, about 0.7%, about 0.8%, about 0.9%, about 1%, about 1.1%, about 1.2%, about 1.3%, about 1.4%, about 1.5%, about 2%, about 2.5%, about 3%, about 3.5%, about 4%, or about 4.5% w/w of the composition; the ethylhexylglycerin is present in an amount of about 0.01%, about 0.05%, about 0.06%, about 0.07%, about 0.08%, about 0.09%, about 0.1%, about 0.12%, about 0.13%, about 0.14%, about 0.15%, about 0.25%, about 0.5%, about 1%, about 1.5%, about 2%, or about 2.5% w/w of the composition; and the EDTA is present in an amount of about 0.01%, about 0.05%, about 0.1%, about 0.5%, about 1%, about 1.5%, or about 2% w/w of the composition.

In some embodiments, the phenoxyethanol and ethylhexylglycerin are present in the composition at a ratio of about 9:1 phenoxyethanol:ethylhexylglycerin (e.g., EUXYL® PE9010).

In some embodiments, the EDTA is disodium EDTA.

In some embodiments, the preservative further includes sodium lignosulfonate.

In some embodiments, the ink composition can further include one or more temporary colorants. In some embodiments, the one or more temporary colorants are present in an amount of about 0.1% to about 10% w/w of the composition. In some embodiments, about 0.1% to about 1%, about 0.1% to about 5%, about 0.1% to about 8%, about 8% to about 10%, about 5% to about 10%, or about 1% to about 10% w/w of the composition. In some embodiments, the one or more temporary colorant are present in an amount of about 2% to about 3% w/w of the composition. In some embodiments, the one or more temporary colorant are present in an amount of about 2.5% w/w of the composition. In some embodiments, the one or more temporary colorants are selected from the group consisting of: iron oxide black ($Fe_3O_4$), iron oxide (FeO), carbon, logwood, ochre, cinnabar (HgS), cadmium red (CdSe), iron (III) oxide ($Fe_2O_3$), naphthol-AS pigment, disazodiarylide, disazopyrazolone, cadmium seleno-sulfide, cadmium yellow (CdS, CdZnS), curcuma yellow, chrome yellow ($PbCrO_4$), disazodiarylide, chromium oxide ($Cr_2O_3$), malachite [$Cu_2(CO_3)(OH)_2$], a ferrocyanide, a ferricyanide, lead chromate, monoazo pigment, Cu/Al phthalocyanine, Cu phthalocyanine, azure blue, cobalt blue, Cu-phthalocyanine, manganese violet (manganese ammonium pyrophosphate), an aluminum salt, quinacridone, dioxazine/carbazole, lead white (lead carbonate), titanium dioxide ($TiO_2$), barium sulfate ($BaSO_4$), zinc oxide, anthraquinone dyes and derivatives, annatto, caramel, β-carotene, bismuth citrate, disodium EDTA copper, potassium sodium copper chlorophyllin, dihydroxyacetone, bismuth oxychloride, guaiazulene, henna, ferric ammonium ferrocyanide, ferric ferrocyanide, chromium hydroxide green, chromium oxide greens, guanine, lead acetate, pyrophillite, mica, silver, titanium dioxide, aluminum powder, bronze powder, copper powder, ultramarines, manganese violet, zinc oxide, luminescent zinc sulfide, D&C Black Nos. 2 and 3, FD&C Blue No. 1 (e.g., acid blue 9), D&C Blue No. 4, D&C Brown No. 1, FD&C Green No. 3, D&C Green Nos. 5, 6, and 8, D&C Orange Nos. 4, 5, 10 and 11, FD&C Red Nos. 4, D&C Red Nos. 6, 7, 17, 21, 22, 27, 28, 30, 32, 33, 34, 36 and 40, D&C Violet No. 2, Ext. D&C Violet No. 2, FD&C Yellow Nos. 5 and 6, D&C Yellow Nos. 7, 8, 10 and 11, and Ext. D&C Yellow No. 7. In some embodiments, the temporary colorant does not contain an amine group. In some embodiments, the temporary colorant is D&C Black No. 2.

In some embodiments, a composition as provided herein includes:

a semi-permanent colorant (e.g., a genipin derivative, lawsone, a lawsone derivative, or a combination thereof, e.g., any of the combinations described herein) present in an amount of about 10% to about 20% w/w of the composition;

a solvent present in an amount of about 65% to about 80% w/w of the composition; and a thickening agent present in an amount of about 0.01% to about 0.3% w/w of the composition. In some embodiments, the solvent is a combination of water and ethanol. In some such embodiments, the water is present in an amount of about 25% to about 30% w/w of the composition, and the ethanol is present in an amount of about 40% to about 50% w/w of the composition. In some embodiments, the thickening agent is a combination of hydroxyethylcellulose and xanthan gum. In some such embodiments, the hydroxyethylcellulose is present in an amount of about 0.01% to about 0.1% w/w of the composition, and the xanthan gum is present in an amount of about 0.01% to about 0.1% w/w of the composition.

In some embodiments, the composition further includes a humectant present in an amount of about 1% to about 10% w/w of the composition. In some embodiments, the humectant is glycerol.

In some embodiments, the composition further includes a film-forming agent present in an amount of about 0.1% to about 10% w/w of the composition. In some embodiments, the film-forming agent is a combination of polymethylsilsesquioxane and acrylates/C12-22 alkyl methacrylate copolymer. In some such embodiments, the polymethylsilsesquioxane is present in an amount of about 1% to about 5% w/w of the composition, and the acrylates/C12-22 alkyl methacrylate copolymer is present in an amount of about 1% to about 5% w/w of the composition.

In some embodiments, the composition further includes a preservative present in an amount of about 0.1% to about 5% w/w of the composition. In some embodiments, the preservative includes a combination of phenoxyethanol and ethylhexylglycerin. In some embodiments, the preservative includes a combination of phenoxyethanol, ethylhexylglycerin, and 1,2-hexanediol. In some such embodiments, the phenoxyethanol and ethylhexylglycerin are together present in the composition in an amount of about 0.1% to about 2% w/w of the composition. In some such embodiments, the phenoxyethanol and ethylhexylglycerin are present in the composition at a ratio of about 9:1 phenoxyethanol:ethylhexylglycerin. In some such embodiments, the 1,2-hexanediol is present in an amount of about 1% to about 3% w/w of the composition.

In some embodiments, a composition as provided herein includes:

a semi-permanent colorant (e.g., a genipin derivative, lawsone, a lawsone derivative, or a combination thereof, e.g., any of the combinations described herein) present in an amount of about 10% to about 20% w/w of the composition;

a solvent present in an amount of about 65% to about 80% w/w of the composition; and a humectant present in an amount of about 1% to about 10% w/w of the composition. In some embodiments, the solvent is a combination of water and ethanol. In some embodiments, the water is present in an amount of about 25% to about 30% w/w of the composition. In some embodiments, the ethanol is present in an amount of about 40% to about 50% w/w of the composition. In some embodiments, the humectant is glycerol.

In some embodiments, the composition further includes a thickening agent present in an amount of about 0.01% to about 0.3% w/w of the composition. In some embodiments, the thickening agent is a combination of hydroxyethylcellulose and xanthan gum. In some such embodiments, the hydroxyethylcellulose is present in an amount of about 0.01% to about 0.1% w/w of the composition, and the xanthan gum is present in an amount of about 0.01% to about 0.1% w/w of the composition.

In some embodiments, the composition further includes a film-forming agent present in an amount of about 0.1% to about 10% w/w of the composition. In some embodiments, the film-forming agent is a combination of polymethylsilsesquioxane and acrylates/C12-22 alkyl methacrylate copolymer. In some such embodiments, the polymethylsilsesquioxane is present in an amount of about 1% to about 5% w/w of the composition, and the acrylates/C12-22 alkyl methacrylate copolymer is present in an amount of about 1% to about 5% w/w of the composition. In some embodiments, the composition further includes a humectant present in an amount of about 1% to about 10% w/w of the composition. In some embodiments, the humectant is glycerol.

In some embodiments, the composition further includes a preservative present in an amount of about 0.1% to about 5% w/w of the composition. In some embodiments, the preservative includes a combination of phenoxyethanol and ethylhexylglycerin. In some embodiments, the preservative includes a combination of phenoxyethanol, ethylhexylglycerin, and 1,2-hexanediol. In some such embodiments, the phenoxyethanol and ethylhexylglycerin are together present in the composition in an amount of about 0.1% to about 2% w/w of the composition. In some such embodiments, the phenoxyethanol and ethylhexylglycerin are present in the composition at a ratio of about 9:1 phenoxyethanol:ethylhexylglycerin. In some such embodiments, the 1,2-hexanediol is present in an amount of about 1% to about 3% w/w of the composition.

In some embodiments, a composition as provided herein includes:

a semi-permanent colorant (e.g., a genipin derivative, lawsone, a lawsone derivative, or a combination thereof, e.g., any of the combinations described herein) present in an amount of about 12% to about 16% w/w of the composition;

a solvent present in an amount of about 72% to about 76% w/w of the composition; and a thickening agent present in an amount of about 0.05% to about 0.20% w/w of the composition. In some embodiments, the solvent is a combination of water and ethanol. In some such embodiments, the water is present in an amount of about 25% to about 30% w/w of the composition, and the ethanol is present in an amount of about 45% to about 47% w/w of the composition. In some embodiments, the thickening agent is a combination of hydroxyethylcellulose and xanthan gum. In some such embodiments, the hydroxyethylcellulose is present in an amount of about 0.04% to about 0.08% w/w of the composition, and the xanthan gum is present in an amount of about 0.04% to about 0.08% w/w of the composition.

In some embodiments, the composition further includes a film-forming agent present in an amount of about 4% to about 6% w/w of the composition. In some embodiments, the film-forming agent is a combination of polymethylsilsesquioxane and acrylates/C12-22 alkyl methacrylate copolymer. In some such embodiments, the polymethylsilsesquioxane is present in an amount of about 1% to about 5% w/w of the composition, and the acrylates/C12-22 alkyl methacrylate copolymer is present in an amount of about 1% to about 5% w/w of the composition.

In some embodiments, the composition further includes a humectant present in an amount of about 2% to about 6% w/w of the composition. In some embodiments, the humectant is glycerol.

In some embodiments, the composition further includes a preservative present in an amount of 2% to about 4% w/w of the composition. In some embodiments, the preservative includes a combination of phenoxyethanol and ethylhexylglycerin. In some embodiments, the preservative includes a combination of phenoxyethanol, ethylhexylglycerin, and 1,2-hexanediol. In some such embodiments, the phenoxyethanol and ethylhexylglycerin are together present in the composition in an amount of about 0.1% to about 2% w/w of the composition. In some such embodiments, the phenoxyethanol and ethylhexylglycerin are present in the composition at a ratio of about 9:1 phenoxyethanol:ethylhexylglycerin. In some such embodiments, the 1,2-hexanediol is present in an amount of about 1% to about 3% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 12% to about 16% w/w of the composition;
- a solvent present in an amount of about 72% to about 76% w/w of the composition; and
- a humectant present in an amount of about 2% to about 6% w/w of the composition. In some embodiments, the solvent is a combination of water and ethanol. In some such embodiments, the water is present in an amount of about 25% to about 30% w/w of the composition, and the ethanol is present in an amount of about 45% to about 47% w/w of the composition. In some embodiments, the humectant is glycerol.

In some embodiments, the composition further includes a thickening agent present in an amount of about 0.05% to about 0.20% w/w of the composition. In some embodiments, the thickening agent is a combination of hydroxyethylcellulose and xanthan gum. In some such embodiments, the hydroxyethylcellulose is present in an amount of about 0.04% to about 0.08% w/w of the composition, and the xanthan gum is present in an amount of about 0.04% to about 0.08% w/w of the composition.

In some embodiments, the composition further includes a film-forming agent present in an amount of about 4% to about 6% w/w of the composition. In some embodiments, the film-forming agent is a combination of polymethylsilsesquioxane and acrylates/C12-22 alkyl methacrylate copolymer. In some such embodiments, the polymethylsilsesquioxane is present in an amount of about 1% to about 5% w/w of the composition, and the acrylates/C12-22 alkyl methacrylate copolymer is present in an amount of about 1% to about 5% w/w of the composition.

In some embodiments, the composition further includes a preservative present in an amount of 2% to about 4% w/w of the composition. In some embodiments, the preservative includes a combination of phenoxyethanol and ethylhexylglycerin. In some embodiments, the preservative includes a combination of phenoxyethanol, ethylhexylglycerin, and 1,2-hexanediol. In some such embodiments, the phenoxyethanol and ethylhexylglycerin are together present in the composition in an amount of about 0.1% to about 2% w/w of the composition. In some such embodiments, the phenoxyethanol and ethylhexylglycerin are present in the composition at a ratio of about 9:1 phenoxyethanol:ethylhexylglycerin. In some such embodiments, the 1,2-hexanediol is present in an amount of about 1% to about 3% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 14% w/w of the composition;
- a solvent present in an amount of about 74% w/w of the composition; and
- a thickening agent present in an amount of about 0.12% w/w of the composition. In some embodiments, the solvent is a combination of water and ethanol.

In some such embodiments, the water is present in an amount of about 28% w/w of the composition, and the ethanol is present in an amount of about 46% w/w of the composition. In some embodiments, the thickening agent is a combination of hydroxyethylcellulose and xanthan gum. In some embodiments, the hydroxyethylcellulose is present in an amount of about 0.06% w/w of the composition, and the xanthan gum is present in an amount of about 0.06% w/w of the composition.

In some embodiments, the composition further includes a film-forming agent present in an amount of about 5% w/w of the composition. In some embodiments, the film-forming agent is a combination of polymethylsilsesquioxane and acrylates/C12-22 alkyl methacrylate copolymer. In some such embodiments, the polymethylsilsesquioxane is present in an amount of about 2% w/w of the composition, and the acrylates/C12-22 alkyl methacrylate copolymer is present in an amount of about 3% w/w of the composition. In some embodiments, the composition further includes a humectant present in an amount of about 4% w/w of the composition. In some embodiments, the humectant is glycerol.

In some embodiments, the composition further includes a preservative present in an amount of 3% w/w of the composition. In some embodiments, the preservative includes a combination of phenoxyethanol and ethylhexylglycerin. In some embodiments, the preservative includes a combination of phenoxyethanol, ethylhexylglycerin, and 1,2-hexanediol. In some such embodiments, the phenoxyethanol and ethylhexylglycerin are together present in the composition in an amount of about 1% w/w of the composition. In some such embodiments, the phenoxyethanol and ethylhexylglycerin are present in the composition at a ratio of about 9:1 phenoxyethanol:ethylhexylglycerin. In some such embodiments, the 1,2-hexanediol is present in an amount of about 2% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 14% w/w of the composition;
- a solvent present in an amount of about 74% w/w of the composition; and
- a humectant present in an amount of about 4% w/w of the composition. In some embodiments, the solvent is a combination of water and ethanol. In some such embodiments, the water is present in an amount of about 28% w/w of the composition, and the ethanol is present in an amount of about 46% w/w of the composition. In some embodiments, the humectant is glycerol.

In some embodiments, the composition further includes a thickening agent present in an amount of about 0.12% w/w of the composition. In some embodiments, the thickening agent is a combination of hydroxyethylcellulose and xanthan gum. In some such embodiments, the hydroxyethylcellulose is present in an amount of about 0.06% w/w of the composition, and the xanthan gum is present in an amount of about 0.06% w/w of the composition.

In some embodiments, the composition further includes a film-forming agent present in an amount of about 5% w/w of the composition. In some embodiments, the film-forming agent is a combination of polymethylsilsesquioxane and acrylates/C12-22 alkyl methacrylate copolymer. In some such embodiments, the polymethylsilsesquioxane is present in an amount of about 2% w/w of the composition, and the acrylates/C12-22 alkyl methacrylate copolymer is present in an amount of about 3% w/w of the composition.

In some embodiments, the composition further includes a preservative present in an amount of 3% w/w of the composition. In some embodiments, the preservative includes a combination of phenoxyethanol and ethylhexylglycerin. In some embodiments, the preservative includes a combination of phenoxyethanol, ethylhexylglycerin, and 1,2-hexanediol. In some such embodiments, the phenoxyethanol and ethylhexylglycerin are together present in the composition in an amount of about 1% w/w of the composition. In some such embodiments, the phenoxyethanol and ethylhexylglycerin are present in the composition at a ratio of about 9:1 phenoxyethanol:ethylhexylglycerin. In some such embodiments, the 1,2-hexanediol is present in an amount of about 2% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 5% to about 15% w/w of the composition;
- a solvent present in an amount of about 65% to about 85% w/w of the composition; and
- a film-forming agent present in an amount of about 5% to about 10% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 9% to about 11% w/w of the composition;
- a solvent present in an amount of about 75% to about 80% w/w of the composition; and
- a film-forming agent present in an amount of about 6% to about 9% w/w of the composition.

In some embodiments, the solvent is a combination of water and ethanol. In some such embodiments, the water is present in an amount of about 25% to about 35% w/w of the composition, and the ethanol is present in an amount of about 45% to about 50% w/w of the composition. In some embodiments, the film-forming agent is a combination of acrylates copolymer, polyvinylpyrrolidone, and styrene/acrylates copolymer.

In some embodiments, the composition further includes a humectant present in an amount of about 0.5% to about 1.5% w/w of the composition. In some embodiments, the humectant is propanediol.

In some embodiments, the composition further includes a preservative present in an amount of 0.5% to about 1.5% w/w of the composition. In some embodiments, the preservative includes a combination of phenoxyethanol and ethylhexylglycerin. In some embodiments, the preservative includes a combination of phenoxyethanol, ethylhexylglycerin, and EDTA. In some such embodiments, the phenoxyethanol and ethylhexylglycerin are together present in the composition in an amount of about 0.1% to about 2% w/w of the composition. In some such embodiments, the phenoxyethanol and ethylhexylglycerin are present in the composition at a ratio of about 9:1 phenoxyethanol:ethylhexylglycerin. In some such embodiments, the EDTA is present in an amount of about 0.05% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 10% w/w of the composition;
- a solvent present in an amount of about 77% w/w of the composition; and
- a film-forming agent present in an amount of about 7.5% w/w of the composition.

In some embodiments, the solvent is a combination of water and ethanol. In some such embodiments, the water is present in an amount of about 30% w/w of the composition, and the ethanol is present in an amount of about 48% w/w of the composition. In some embodiments, the film-forming agent is a combination of acrylates copolymer, polyvinylpyrrolidone, and styrene/acrylates copolymer.

In some embodiments, the composition further includes a humectant present in an amount of about 1% w/w of the composition. In some embodiments, the humectant is propanediol.

In some embodiments, the composition further includes a preservative present in an amount of about 1.05% w/w of the composition. In some embodiments, the preservative includes a combination of phenoxyethanol and ethylhexylglycerin. In some embodiments, the preservative includes a combination of phenoxyethanol, ethylhexylglycerin, and EDTA. In some such embodiments, the phenoxyethanol and ethylhexylglycerin are together present in the composition in an amount of about 1% w/w of the composition. In some such embodiments, the phenoxyethanol and ethylhexylglycerin are present in the composition at a ratio of about 9:1 phenoxyethanol:ethylhexylglycerin. In some such embodiments, the EDTA is present in an amount of about 0.05% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 0.1% to about 1.5% w/w of the composition;
- a solvent present in an amount of about 80% to about 90% w/w of the composition; and
- a humectant present in an amount of about 10% to about 15% w/w of the composition.

In some embodiments, the solvent is a combination of water and ethanol. In some such embodiments, the water is present in an amount of about 65% to about 75% w/w of the composition, and the ethanol is present in an amount of about 10% to about 20% w/w of the composition. In some embodiments, the humectant is vegetable oil.

In some embodiments, the composition further includes a thickening agent present in an amount of about 1% to about 10% w/w of the composition. In some embodiments, the thickening agent is xanthan gum. In some embodiments, the composition further comprises a temporary colorant present in an amount of less than about 0.1% w/w of the composition. In some embodiments, the composition further comprises an amine present in an amount of about 0.01% to about 1% w/w of the composition.

In some embodiments, a composition as provided herein includes:

- a semi-permanent colorant (e.g., a genipin derivative, lawsone, a lawsone derivative, or a combination thereof, e.g., any of the combinations described herein) present in an amount of about 0.9% w/w of the composition;
- a solvent present in an amount of about 86% w/w of the composition; and
- a humectant present in an amount of about 9% w/w of the composition. In some embodiments, the solvent is a combination of water and ethanol. In some such embodiments, the water is present in an amount of about 71% w/w of the composition, and the ethanol is present in an amount of about 14% w/w of the composition. In some embodiments, the humectant is vegetable oil.

In some embodiments, the composition further includes a thickening agent present in an amount of about 4% w/w of the composition. In some embodiments, the thickening agent is xanthan gum. In some embodiments, the composition further comprises a temporary colorant present in an amount of less than about 0.1% w/w of the composition. In some embodiments, the composition further comprises an amine present in an amount of about 0.02% w/w of the composition.

OTHER EMBODIMENTS

Embodiment 1 is an ink applicator, comprising:

a lower body, comprising:

a reservoir container contained in a cavity of the lower body;

a reservoir contained in a cavity of the reservoir container; and a semi-permanent ink contained in the reservoir.

Embodiment 2 is an ink applicator, comprising:

a lower body, comprising:

a reservoir contained in a cavity of the lower body; and a semi-permanent ink contained in the reservoir.

Embodiment 3 is the ink applicator of embodiment 1 or embodiment 2, wherein the reservoir comprises polyethylene terephthalate.

Embodiment 4 is the ink applicator of embodiment 3, wherein the polyethylene terephthalate is saturated in the semi-permanent ink.

Embodiment 5 is the ink applicator of any one of embodiment 1-4, further comprising an agitator contained in the reservoir.

Embodiment 6 is the ink applicator of embodiment 5, wherein the agitator is metallic.

Embodiment 7 is an ink applicator, comprising:

a lower body, comprising:

a reservoir container contained in a cavity of the lower body; and a semi-permanent ink contained in the reservoir.

Embodiment 8 is an ink applicator, comprising:

a lower body comprising a semi-permanent ink contained in a cavity of the lower body.

Embodiment 9 is the ink applicator of any one of embodiments 1-8, wherein the lower body further comprises external threading coupleable to an upper body.

Embodiment 10 is the ink composition of embodiment 9, wherein the upper body comprises a nib comprising a first end that is external to the upper body and a second end internal to the upper body, wherein the nib is configured to dispense the semi-permanent ink.

Embodiment 11 is an ink applicator, comprising:

a lower body coupled to an upper body, the upper body comprising:

a nib comprising a first end that is external to the upper body and a second end internal to the upper body, wherein the nib is configured to dispense a semi-permanent ink.

Embodiment 12 is the ink applicator of embodiment 11, further comprising a reservoir container contained in a cavity of the lower body.

Embodiment 13 is the ink applicator of embodiment 12, further comprising a reservoir contained in a cavity of the reservoir container, wherein the semi-permanent ink is contained in the reservoir.

Embodiment 14 is the ink applicator of embodiment 12 or embodiment 13, wherein the reservoir comprises polyethylene terephthalate.

Embodiment 15 is the ink applicator of embodiment 14, wherein the polyethylene terephthalate is saturated in the semi-permanent ink.

Embodiment 16 is an ink applicator, comprising:

a lower body, comprising:

a reservoir container contained in a cavity of the lower body;

a reservoir contained in a cavity of the reservoir container; and a semi-permanent ink contained in the reservoir; and an upper body coupled to the lower body, the upper body comprising:

a nib comprising a first end that is external to the upper body and a second end internal to the upper body.

Embodiment 17 is the ink applicator of embodiment 16, wherein the reservoir comprises polyethylene terephthalate.

Embodiment 18 is the ink applicator of embodiment 17, wherein the polyethylene terephthalate is saturated in the semi-permanent ink.

Embodiment 19 is an ink applicator, comprising:

a lower body, comprising:

a reservoir container contained in a cavity of the lower body;

a reservoir contained in a cavity of the reservoir container; and a semi-permanent ink contained in the reservoir; and an upper body coupled to the lower body, the upper body comprising:

a nib comprising a first end that is external to the upper body and a second end internal to the upper body; and a transfer nib that contacts the second end of the nib and the semi-permanent ink contained in the reservoir.

Embodiment 20 is the ink applicator of embodiment 19, further comprising an agitator contained in the reservoir.

Embodiment 21 is the ink applicator of embodiment 20, wherein the agitator is metallic.

Embodiment 22 is the ink applicator of embodiment 20 or embodiment 21, wherein the agitator is a metallic bead.

Embodiment 23 is the ink applicator of any one of embodiments 19-22, wherein the nib includes nylon brush fibers and is configured to couple to the transfer nib.

Embodiment 24 is the ink applicator of any one of embodiments 19-22, wherein the nib includes a flexible and porous tip and is configured to couple to the transfer nib.

Embodiment 25 is the ink applicator of any one of embodiments 19-24, wherein the semi-permanent ink is absorbed by the transfer nib and the semi-permanent ink absorbed by the nib it transferred to the second end of the nib.

Embodiment 26 is the ink applicator of any one of embodiments 19-25, further comprising a transfer casing adjacent to the first end of the nib.

Embodiment 27 is the ink applicator of embodiment 26, wherein the transfer casing couples the transfer nib to the nib.

Embodiment 28 is the ink applicator of embodiment 27 or embodiment 26, wherein the transfer casing secures the transfer nib to the upper body.

Embodiment 29 is the ink applicator of any one of embodiments 26-28, wherein the transfer casing is configured to absorb excess semi-permanent ink from the reservoir.

Embodiment 30 is the ink applicator of any one of embodiments 16-29, wherein the second end of the nib contacts the semi-permanent ink contained in the reservoir.

Embodiment 31 is the ink applicator of any one of embodiments 16-29, wherein the first end of the nib is configured to deposit the semi-permanent ink composition onto a substrate Embodiment 32 is the ink applicator of embodiment 31, wherein the substrate is paper.

Embodiment 33 is the ink applicator of embodiment 31, wherein the substrate is animal skin.

Embodiment 34 is the ink applicator of any one of embodiments 16-33, wherein the reservoir is selectively removable.

Embodiment 35 is the ink applicator of any one of embodiments 16-34, wherein the lower body further comprises a transparent window.

Embodiment 36 is the ink applicator of embodiment 35, wherein the reservoir is visible via the transparent window.

Embodiment 37 is the ink applicator of any one of embodiments 11-36, further comprising:

external threading integrated to the lower body; and internal threading integrated to the upper body, wherein the external threading and the internal threading are complementary and couple the lower body to the upper body.

Embodiment 38 is the ink applicator of embodiment 37, wherein the internal threading and the external threading couple the upper body and the lower body such that the cavity of the lower body is sealed.

Embodiment 39 is the ink applicator of any one of embodiments 11-38, wherein the nib includes a firm round tip.

Embodiment 40 is the he ink applicator of any one of embodiments 11-38, wherein the nib includes a chiseled tip.

Embodiment 41 is the ink applicator of any one of embodiments 11-38, wherein the nib includes a fine pointed tip.

Embodiment 42 is the ink applicator of any one of embodiments 11-41, further comprising a lid configured to cover the first end of the nib that is external to the upper body.

Embodiment 43 is the ink applicator of embodiment 42, wherein the lid provides a seal between the lid and the upper body.

Embodiment 44 is the ink applicator of any one of embodiments 16-41, wherein the reservoir comprises a void.

Embodiment 45 is the ink applicator of embodiment 44, wherein the void is configured to contain a volume of semi-permanent ink.

Embodiment 46 is the ink applicator of embodiment 45, wherein the volume is about 0.5 mL to about 1.5 mL.

Embodiment 47 is the ink applicator of embodiment 45 or embodiment 46, wherein the volume is about 1.0 mL.

Embodiment 48 is the ink applicator of any one of embodiments 11-47, wherein the ink applicator is a pen.

Embodiment 49 is the ink applicator of any one of embodiments 11-48, wherein the ink applicator is a marker.

Embodiment 50 is an ink applicator system, comprising:

a reservoir comprising semi-permanent ink; and a plurality of nibs configured to contact the semi-permanent ink in the reservoir.

Embodiment 51 is the ink applicator system of embodiment 19, wherein a first nib of the plurality of nibs includes a firm round tip.

Embodiment 52 is the ink applicator system of any one of embodiments 50-51, wherein a second nib of the plurality of nibs includes a chiseled tip.

Embodiment 53 is the ink applicator system of any one of embodiments 50-52, wherein a third nib of the plurality of nibs includes a fine pointed tip.

Embodiment 54 is the ink applicator system of any one of embodiments 50-53, wherein a fourth nib of the plurality of nibs includes nylon brush fibers.

Embodiment 55 is the ink applicator system of any one of embodiments 50-54, wherein a fifth nib of the plurality of nibs includes a flexible porous tip.

Embodiment 56 is the ink applicator system of any one of embodiments 50-55, further comprising a pouch of the semi-permanent ink.

Embodiment 57 is the ink applicator system of embodiment 56, wherein the pouch includes a capacity of about 0.5 mL to about 1.5 mL for the semi-permanent ink.

Embodiment 58 is the ink applicator system of embodiment 56 or embodiment 57, wherein the pouch includes a capacity of about 1.0 mL for the semi-permanent tattoo composition.

Embodiment 59 is the ink applicator system of any one of embodiments 50-58, wherein the reservoir further comprises polyethylene terephthalate.

Embodiment 60 is the ink applicator system of embodiment 59, wherein the polyethylene terephthalate is saturated with the semi-permanent ink.

Embodiment 61 is the ink applicator system of any one of embodiments 50-60, wherein each of the plurality of nibs corresponds to a color of the semi-permanent ink.

Embodiment 62 is the ink applicator system of any one of embodiments 50-61, further comprising an ink applicator as set forth in any one of embodiments 1-49.

Embodiment 63 is a method for applying ink onto skin, the method comprising:

coupling a nib to an upper body of an ink applicator comprising an ink composition; and applying the ink composition of the ink applicator to a portion of the skin.

Embodiment 64 is the method of embodiment 63, wherein the ink applicator is a marker.

Embodiment 65 is the method of any one of embodiments 63-64, further comprising agitating the ink applicator to begin the flow of ink composition from a reservoir of the ink applicator to the nib.

Embodiment 66 is the method of embodiment 65, further comprising:

decoupling the upper body of the ink applicator from a lower body of the ink applicator;

removing the reservoir from the lower body; and replacing the reservoir with a different reservoir.

Embodiment 67 is the method of embodiment 66, further comprising:

decoupling the upper body of the ink applicator from a lower body of the ink applicator;

removing the reservoir from the lower body; and filling the reservoir with additional ink composition.

Embodiment 68 is the method of any one of embodiments 63-67, further comprising:

decoupling the nib from the ink applicator;

coupling a different nib to the ink applicator; and applying the ink via the ink applicator and different nib to the portion of the skin.

Embodiment 69 is the ink applicator of any one of embodiments 1-49, wherein the semi-permanent ink comprises:

a semi-permanent colorant, wherein the semi-permanent colorant comprises genipin, a genipin derivative, lawsone, a lawsone derivative, or combinations thereof;

a solvent; and a film-forming agent.

Embodiment 70 is the ink applicator of embodiment 69, wherein the genipin derivative is a compound of Formula I:

I

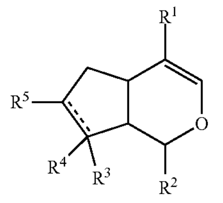

wherein:

$R^1$ is —C(═O)OR$^6$, $C_{1-6}$ alkyl, or $C_{6-10}$ aryl, wherein said $C_{1-6}$ alkyl and $C_{6-10}$ aryl are each optionally substituted with 1-5 $R^7$;

$R^6$ is H, $C_{1-6}$ alkyl, or $C_{6-10}$ aryl, wherein said $C_{1-6}$ alkyl and $C_{6-10}$ aryl are each optionally substituted with 1-5 $R^7$;

each $R^7$ is independently an electron withdrawing or an electron donating group;

$R^2$ is H, —OR$^9$, or OC(═O)R$^{9A}$;

$R^9$ is selected from the group consisting of: H, $C_{1-6}$ alkyl, $C_{6-10}$ aryl, and a hydroxyl-protecting group;

$R^{9A}$ is selected from $C_{1-6}$ alkyl and $C_{6-10}$ aryl; and the dotted line indicates the optional presence of a double bond;

wherein if the double bond is absent, then $R^4$ and $R^5$ together with the carbon atoms to which they are attached form a 3-4 membered heterocyclic ring and $R^3$ is —OH or —$CH_2OH$; or if the double bond is present, then $R^4$ and $R^5$ are absent and $R^3$ is selected from the group consisting of: —NR$^7$R$^8$, —CH$_2$NR$^7$R$^8$, —C(═O)OR$^{10}$, —C(═O)NR$^{10}$R$^{10}$, —CH(═O), phenyl, —CHR$^{10}$R$^{10}$, —CH═CHR$^{10}$, —CH═CR$^{10}$R$^{10}$, —CH$_2$OR$^{10}$, and phenyl substituted with 1-5 $R^7$;

wherein $R^{10}$ is selected from H, $C_{1-6}$ alkyl, alkoxy, oxo, —OH, —CH(═O), —C(═O)OR$^6$, phenyl, and phenyl substituted with 1-5 $R^7$; and $R^8$ is H or $R^7$.

Embodiment 71 is the ink applicator of embodiment 60, wherein:

$R^1$ is —C(═O)OR$^6$ or phenyl substituted with 1-5 $R^7$;

$R^6$ is H, $C_{1-6}$ alkyl, or phenyl substituted with 1-5 $R^7$;

$R^2$ is H, —OR$^9$, or OC(═O)R$^9$;

$R^9$ is H or $C_{1-6}$ alkyl;

if the double bond is present, then $R^4$ and $R^5$ are absent and $R^3$ is selected from the group consisting of: —NR$^7$R$^8$, —CH$_2$NR$^7$R$^8$, —C(═O)OR$^{10}$, —CH(═O), phenyl, —CHR$^{10}$R$^{10}$, —CH═CHR$^{10}$, —CH$_2$OR$^{10}$, diethyl malonate, and phenyl substituted with 1-5 $R^7$; and $R^{10}$ is selected from H, $C_{1-6}$ alkyl, alkoxy, oxo, —OH, —CH(═O) and phenyl substituted with 1-5 $R^7$.

Embodiment 72 is the compound of embodiment 70, wherein the hydroxyl-protecting group is tri($C_{1-6}$ alkyl)silyl.

Embodiment 73 is the compound of embodiment 70, wherein the hydroxyl-protecting group is tert-butyldimethylsilyl (TBS), trimethylsilyl (TMS), or triethylsilyl (TES).

Embodiment 74 is the ink applicator of any one of embodiments 70-73, wherein $R^6$ is methyl.

Embodiment 75 is the ink applicator of any one of embodiments 70-74, wherein $R^1$ is —C(═O)OR$^6$ and $R^6$ is methyl.

Embodiment 76 is the ink applicator of any one of embodiments 70-74, wherein $R^1$ is —C(═O)OR$^6$ and $R^6$ is phenyl substituted with 1-5 $R^7$.

Embodiment 77 is the ink applicator of any one of embodiments 70-76, wherein $R^2$ is —OC(═O)CH$_3$.

Embodiment 78 is the ink applicator of any one of embodiments 70-76, wherein $R^2$ is —OH.

Embodiment 79 is the ink applicator of any one of embodiments 70-76, wherein $R^2$ is —OR$^9$ and $R^9$ is selected from the group consisting of: H, $C_{1-6}$ alkyl, tert-butyldimethylsilyl (TBS), trimethylsilyl (TMS), triethylsilyl (TES), and $C_{6-10}$ aryl.

Embodiment 80 is the ink applicator of any one of embodiments 70-76 and 79, wherein $R^9$ is H.

Embodiment 81 is the ink applicator of any one of embodiments 70-76 and 79, wherein $R^9$ is tert-butyldimethylsilyl (TBS).

Embodiment 82 is the ink applicator of any one of embodiments 70-76 and 79, wherein $R^9$ is —OH.

Embodiment 83 is the ink applicator of any one of embodiments 70-82, wherein the double bond is absent.

Embodiment 84 is the ink applicator of embodiment 83, wherein then $R^4$ and $R^5$ together with the carbon atoms to which they are attached form a 3-membered heterocyclic ring and $R^3$ is —CH$_2$OH.

Embodiment 85 is the ink applicator of embodiment 84, wherein the 3-membered heterocyclic ring is:

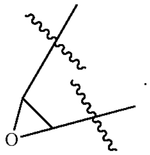 [SMILES: *C1OC1*]

Embodiment 86 is the ink applicator of embodiment 83, wherein then $R^4$ and $R^5$ together with the carbon atoms to which they are attached form a 4-membered heterocyclic ring and $R^3$ is —OH.

Embodiment 87 is the ink applicator of embodiment 86, wherein the 4-membered ring is:

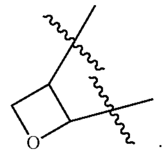 [SMILES: *C1COC1*]

.

Embodiment 88 is the ink applicator of any one of embodiments 70-82, wherein the double bond is present.

Embodiment 89 is the ink applicator of embodiment 88, wherein $R^1$ is phenyl substituted with 1-3 $R^7$.

Embodiment 90 is the ink applicator of embodiment 88, wherein $R^1$ is —C(═O)$OR^6$ and $R^6$ is phenyl substituted with 1-3 $R^7$.

Embodiment 91 is the ink applicator of any one of embodiments 88-90, wherein $R^2$ is —OH and $R^3$ is $CH_2OH$.

Embodiment 92 is the ink applicator of embodiment 88, wherein $R^3$ is selected from the group consisting of:

—$NR^7R^8$, —$CH_2NR^7R^8$, —C(═O)$OR^{10}$, —C(═O)N$R^{10}R^{10}$, —CH(═O), phenyl, —$CHR^{10}R^{10}$, —CH═$CHR^{10}$, —CH═$CR^{10}R^{10}$, —$CH_2OR^{10}$, and phenyl substituted with 1-5 $R^7$;

$R^1$ is —C(═O)OH;

$R^2$ is —OH; and $R^{10}$ is selected from H, $C_{1-6}$ alkyl, alkoxy, oxo, —OH, —CH(═O), —C(═O)$OR^6$, phenyl, and phenyl substituted with 1-5 $R^7$.

Embodiment 93 is the ink applicator of embodiment 88, wherein $R^3$ is selected from the group consisting of:

—$NR^7R^8$, —$CH_2$—$NR^7R^8$, —C(═O)$OR^{10}$, —CH(═O), phenyl, —$CHR^{10}R^{10}$, —CH═$CHR^{10}$, C(═O)$NR^{10}R^{10}$, —$CH_2OR^{10}$, and phenyl substituted with 1-5 $R^7$;

$R^1$ is —C(═O)OH; and $R^2$ is —$OR^9$ and $R^9$ is selected from the group consisting of: H, $C_{1-6}$ alkyl, tert-butyldimethylsilyl (TBS), trimethylsilyl (TMS), triethylsilyl (TES), and $C_{6-10}$ aryl.

Embodiment 94 is the ink applicator of embodiment 88, wherein $R^3$ is selected from the group consisting of:

—$NR^7R^8$, —$CH_2$—$NR^7R^8$, —C(═O)$OR^{10}$, —CH(═O), phenyl, —$CHR^{10}R^{10}$, —CH═$CHR^{10}$, —$CH_2OR^{10}$, diethyl malonate, and phenyl substituted with 1-5 $R^7$;

$R^1$ is —C(═O)OH; and $R^2$ is —OH.

Embodiment 95 is the ink applicator of any one of embodiments 69-70, wherein the genipin derivative is a compound selected from the group consisting of the compounds delineated in Table 1.

Embodiment 96 is the ink applicator of any one of embodiments 70-94, wherein $R^7$ is selected from the group consisting of: —($C_{1-9}$ alkyl), —($C_{2-9}$ alkenyl), phenyl, —$NR^8R^8$, —$OR^8$, —NHC(═O)$R^8$, —OC(═O)$R^8$, —$SR^8$, —$CO_2^-$, —$SO_2CF_3$, —NO, —$NO_2$, —$SO_2R^8$, —CN, —$CR^{11}$, —$COR^{11}$, —CHO, —$CO_2R^8$, —C(═O)$NR^8R^8$, and halide;

wherein $R^8$ is selected from the group consisting of: H, —($C_{1-9}$ alkyl), and —($C_{2-9}$ alkenyl); and $R^{11}$ is halide.

Embodiment 97 is the ink applicator of any one of embodiments 69-96, wherein the lawsone derivative is the compound delineated in Table 4.

Embodiment 98 is the ink applicator of any one of embodiments 69-97, wherein the lawsone derivative is a compound of Formula III:

III

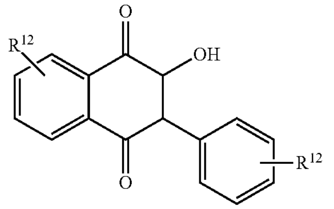

wherein $R^{12}$ is selected from the group consisting of: —($C_{1-9}$ alkyl), —($C_{2-9}$ alkenyl), phenyl, —$NR^8R^8$, —$OR^8$, —NHC(═O)$R^8$, —OC(═O)$R^8$, —$SR^8$, —$CO_2^-$,—$SO_2CF_3$, —NO, —$NO_2$, —$SO_2R^8$, —CN, —$CR^{11}_3$, —$COR^{11}$, —CHO, —$CO_2R^8$, —C(═O)$NR^8R^8$, and halide;

wherein $R^8$ is selected from the group consisting of: H, —($C_{1-9}$ alkyl), and —($C_{2-9}$ alkenyl); and $R^{11}$ is halide.

Embodiment 99 is the ink applicator of any one of embodiments 69-98, wherein the semi-permanent colorant is a combination of two or more of: genipin, a genipin derivative, lawsone, and a lawsone derivative.

Embodiment 100 is the ink applicator of any one of embodiments 69-99, wherein the semi-permanent colorant comprises a combination of two or more genipin derivatives.

Embodiment 101 is the ink applicator of any one of embodiments 69-99, wherein the semi-permanent colorant comprises a combination of two or more compounds as delineated in Table 1.

Embodiment 102 is the ink applicator of any one of embodiments 69-99 and 101, wherein the semi-permanent colorant comprises a combination of Compound 1 and Compound 12.

Embodiment 103 is the ink applicator of embodiment 102, wherein the ratio of Compound 1 to Compound 12 is about 4:1 to about 1:4 Compound 1:Compound 12.

Embodiment 104 is the ink applicator of any one of embodiments 69-99, wherein the semi-permanent colorant is a combination of genipin and Compound 1.

Embodiment 105 is the ink applicator of embodiment 104, wherein the ratio of genipin to Compound 1 is about 4:1 to about 1:4 genipin:Compound 1.

Embodiment 106 is the ink applicator of embodiment 105, wherein the ratio of genipin to Compound 1 is about 1:1 genipin:Compound 1.

Embodiment 107 is the ink applicator of any one of embodiments 69-99 and 101, wherein the semi-permanent colorant is a combination of Compound 1 and Compound 14.

Embodiment 108 is the ink applicator of embodiment 107, wherein the ratio of Compound 1 to Compound 14 is about 4:1 to about 1:4 Compound 1:Compound 14.

Embodiment 109 is the ink applicator of embodiment 108, wherein the ratio of Compound 1 to Compound 14 is about 1:1 Compound 1:Compound 14.

Embodiment 110 is the ink applicator of any one of embodiments 69-99, the semi-permanent colorant is a combination of genipin and Compound 14.

Embodiment 111 is the ink applicator of embodiment 110, wherein the ratio of genipin to Compound 14 is about 4:1 to about 1:4 genipin:Compound 14.

Embodiment 112 is the ink applicator of embodiment 111, wherein the ratio of genipin to Compound 14 is about 1:1 genipin:Compound 14.

Embodiment 113 is the ink applicator of any one of embodiments 69-99, the semi-permanent colorant is a combination of genipin, Compound 1, and Compound 14.

Embodiment 114 is the ink applicator of embodiment 113, wherein the ratio of genipin to Compound 1 to Compound 14 is about 4:1:1 to about 1:1:4 genipin:Compound 1:Compound 14.

Embodiment 115 is the ink applicator of embodiment 114, wherein the ratio of genipin to Compound 1 to Compound 14 is about 1:1:1 genipin: Compound 1:Compound 14.

Embodiment 116 is the ink applicator of any one of embodiments 69-115, wherein the semi-permanent colorant is present in an amount of about 5% to about 15% w/w of the composition.

Embodiment 117 is the ink applicator of any one of embodiments 69-116, wherein the semi-permanent colorant is present in an amount of about 9% to about 11% w/w of the composition.

Embodiment 118 is the ink applicator of any one of embodiments 69-117, wherein the semi-permanent colorant is present in an amount of about 10% w/w of the composition.

Embodiment 119 is the ink applicator of any one of embodiments 69-118, wherein the solvent is present in an amount of about 65% to about 85% w/w of the composition.

Embodiment 120 is the ink applicator of any one of embodiments 69-119, wherein the solvent is present in an amount of about 75% to about 80% w/w of the composition.

Embodiment 121 is the ink applicator of any one of embodiments 69-120, wherein the solvent is present in an amount of about 77% w/w of the composition.

Embodiment 122 is the ink applicator of any one of embodiments 69-121, wherein the solvent comprises water, methanol, ethanol, isopropanol, diethylene glycol monoethyl ether, or a combination thereof.

Embodiment 123 is the ink applicator of any one of embodiments 69-122, wherein the solvent is a combination of water and ethanol.

Embodiment 124 is the ink applicator of any one of embodiments 122-123, wherein the water is present in an amount of about 25% to about 35% w/w of the composition.

Embodiment 125 is the ink applicator of any one of embodiments 122-124, wherein the water is present in an amount of about 30% w/w of the composition.

Embodiment 126 is the ink applicator of any one of embodiments 122-125, wherein the ethanol is present in an amount of about 40% to about 55% w/w of the composition.

Embodiment 127 is the ink applicator of any one of embodiments 122-126, wherein the ethanol is present in an amount of about 45% to about 50% w/w of the composition.

Embodiment 128 is the ink applicator of any one of embodiments 122-127, wherein the ethanol is present in an amount of about 48% w/w of the composition.

Embodiment 129 is the ink applicator of any one of embodiments 69-128, wherein the film-forming agent is present in an amount of about 5% to about 10% w/w of the composition.

Embodiment 130 is the ink applicator of any one of embodiments 69-129, wherein the film-forming agent is present in an amount of about 6% to about 9% w/w of the composition.

Embodiment 131 is the ink applicator of any one of embodiments 69-130, wherein the film-forming agent is present in an amount of about 7.5% w/w of the composition.

Embodiment 132 is the ink applicator of any one of embodiments 69-131, wherein the film-forming agent comprises a volatile silicon resin, polyvinylpyrrolidone, an acrylate, an acrylamide, a copolymer, an isododecane resin, or a combination thereof.

Embodiment 133 is the ink applicator of any one of embodiments 69-132, wherein the film-forming agent comprises polymethylsilsesquioxane, trimethylsiloxysilicate, polypropylsilsesquioxane, dimethicone, cyclopentasiloxane, dimethiconol crosspolymer, polysilicone-6, polysilicone-8, polysilicone-11, polysilicone-14, acrylates copolymer, styrene/acrylates copolymer, polyvinylpyrrolidone, acrylates/C12-22 alkyl methacrylate copolymer, acrylates/polytrimethylsiloxymethacrylate copolymer, polyvinylpyrrolidone/vinyl acetate (VP/VA) copolymer, VP/dimethiconylacrylate/polycarbamyl/polyglycol ester, VP/dimethylaminoethylmethacrylate copolymer, VP/dimethylamino ethylmethacrylate/polycarbamyl polyglycol ester, VP/eicosene copolymer, VP/hexadecene copolymer, VP/methacrylamide/vinyl imidazole copolymer, VP/polycarbamyl polyglycol ester, VP/VA copolymer, polyester-1, polyester-2, polyester-3, polyester-4, polyester-5, polyester-7, polyester-8, and polyester-10, or a combination thereof.

Embodiment 134 is the ink applicator of any one of embodiments 69-133 wherein the film-forming agent is a combination of acrylates copolymer, polyvinylpyrrolidone, and styrene/acrylates copolymer.

Embodiment 135 is the ink applicator of any one of embodiment 133 or 134, wherein the acrylates copolymer is present in an amount of about 0.1% to about 10% w/w of the composition.

Embodiment 136 is the ink applicator of any one of embodiments 133-135, wherein the acrylates copolymer is present in an amount of about 0.1% to about 1% w/w of the composition.

Embodiment 137 is the ink applicator of any one of embodiments 133-136, wherein the acrylates copolymer is present in an amount of about 0.25% w/w of the composition.

Embodiment 138 is the ink applicator of any one of embodiments 133-137, wherein the polyvinylpyrrolidone is present in an amount of about 0.1% to about 10% w/w of the composition.

Embodiment 139 is the ink applicator of any one of embodiments 133-138, wherein the polyvinylpyrrolidone is present in an amount of about 0.5% to about 1.5% w/w of the composition.

Embodiment 140 is the ink applicator of any one of embodiments 133-139, wherein the polyvinylpyrrolidone is present in an amount of about 1% w/w of the composition.

Embodiment 141 is the ink applicator of any one of embodiments 133-140, wherein the styrene/acrylates copolymer is present in an amount of about 0.1% to about 10% w/w of the composition.

Embodiment 142 is the ink applicator of any one of embodiments 133-141, wherein the styrene/acrylates copolymer is present in an amount of about 5% to about 7% w/w of the composition.

Embodiment 143 is the ink applicator of any one of embodiments 133-142, wherein the styrene/acrylates copolymer is present in an amount of about 6% w/w of the composition.

Embodiment 144 is the ink applicator of any one of embodiments 69-143, wherein the composition further comprises a humectant.

Embodiment 145 is the ink applicator of embodiment 144, wherein the humectant is present in an amount of about 0.1% to about 10% w/w of the composition.

Embodiment 146 is the ink applicator of any one of embodiments 144-145, wherein the humectant is present in an amount of about 0.5% to about 1.5% w/w of the composition.

Embodiment 147 is the ink applicator of any one of embodiments 144-146, wherein the humectant is present in an amount of about 1% w/w of the composition.

Embodiment 148 is the ink applicator of any one of embodiments 144-147, wherein the humectant comprises Aloe vera gel, lithium chloride, allantoin, urea, dicyanamideglycerol, lactic acid, propylene glycol, polyethylene glycol, dipropylene glycol, polypropylene glycol, polyethylene glycol, propanediol, hexylene glycol, 1,3-butylene glycol, 1,2,6-hexanetriol, ethoxylated glycerol, propoxylated glycerol, glyceryl triacetate, sorbitol, hydroxypropyl sorbitol, xylitol, maltitol, hyaluronic acid, Tremella extract, sodium lactate, sodium L-pyroglutamate urea, and pyrrolidone carboxylic acid, or a combination thereof.

Embodiment 149 is the ink applicator of any one of embodiments 144-148, wherein the humectant is propanediole.

Embodiment 150 is the ink applicator of any one of embodiments 69-149, wherein the composition further comprises a preservative.

Embodiment 151 is the ink applicator of embodiment 150, wherein the preservative is present in an amount of about 0.1% to about 5% w/w of the composition.

Embodiment 152 is the ink applicator of embodiment 150 or 151, wherein the preservative is present in an amount of about 0.5% to about 1.5% w/w of the composition.

Embodiment 153 is the ink applicator of any one of embodiment 150-152, wherein the preservative is present in an amount of about 1% w/w of the composition.

Embodiment 154 is the ink applicator of any one of embodiment 150-153, wherein the preservative comprises ascorbic acid, an ascorbate, a palmitate, citric acid, a benzoate, a benzoic acid, a propionate, propionic acid, a sorbate, sorbic acid, a salicylic acid, a salicylate, hexa-2,4-dienoic acid, a hexa-2,4-dienoate, formaldehyde, a formaldehyde releaser, formic acid and its salts, 3-acetyl-6-methylpyran-2,4-(3H)-dione and its salts, 3,3'-dibromo-4,4'-hexamethylenedioxydibenzamidine and its salts, thiomersal, phenylmercuric salts, undec-10-enoic acid and its salts, 1,3-bis(2-ethylhexyl) hexahydro-5-methyl-5-pyrimidine, 5-bromo-5-nitro-1,3-dioxane, bronopol, 2,4-dichlorobenzyl alcohol, 1-(4-chlorophenyl)-3-(3,4-dichlorophenyl) urea, chlorocresol, chloroxylenol, 5-chloro-2-(2,4-dichlorophenoxy) phenol, N,N"-methylenebis[N'-[3-(hydroxymethyl)-2,5-dioxoimidazolidin-4-yl]urea], polyaminopropyl biguanide, methenamine, quaternium-15, climbazole, DMDM hydantoin, benzyl alcohol, 1-Hydroxy-4-methyl-6-(2,4,4-trimethylpentyl)-2-pyridon, piroctone olamine, bromochlorophene, o-cymen-5-ol, chlorophene, chloroacetaminde, methylchloroisothiazolinone, methylisothiazolinone, phenoxyisopropanol, chlorhexidine, chlorhexidine diacetate, chlorhexidine digluconate, chlorhexidine dihydrochloride, dimethyl oxazolidine, behentrimonium chloride, cetri-monium bromide, cetrimonium chloride, laurtrimonium bromide, laurtrimonium chloride, steartrimonium bromide, steartrimonium chloride, diazolidinyl urea, hexamidine, hexamidine diisethionate, hexamidine paraben, glutaral, 7-ethylbicyclooxazolidine, chlorphenesin, sodium hydroxymethylglycinate, silver chloride, benzethonium chloride, benzalkonium chloride, benzalkonium bromide, benzalkonium saccharinate, benzylhemiformal, iodopropynyl butylcarbamate, biphenyl-2-ol and its salts, pyrithionine zinc, an erythorbate, a nitrite, ethylenediaminetetraacetic acid (EDTA), butylated hydroxyanisole (BHA), butylated hydroxytoluene (BHT), capryllic acid, dilauryl thiodipropionate, erythorbic acid, gum guaiac, methylparaben, a sulfite, a bisulfite, a metabisulfite, propyl gallatepy, propylparaben, stannous chloride, sulfur dioxide, thiodipropionic acid, an isothiazoline, a paraben, phenoxyethanol, ethylhexylglycerin, a glycol, a tocopherol, 1,2-hexanediol, or a combination thereof.

Embodiment 155 is the ink applicator of any one of embodiment 150-154, wherein the preservative comprises a combination of phenoxyethanol and ethylhexylglycerin.

Embodiment 156 is the ink applicator of embodiment 155, wherein the combination of phenoxyethanol and ethylhexylglycerin is present in the composition at a ratio of about 9:1 phenoxyethanol:ethylhexylglycerin.

Embodiment 157 is the ink applicator of embodiment 155 or 156, wherein the combination of phenoxyethanol and ethylhexylglycerin is present in an amount of about 0.1% to about 2% w/w of the composition.

Embodiment 158 is the ink applicator of any one of embodiments 155-157, wherein the combination of phenoxyethanol and ethylhexylglycerin is present in an amount of about 1% w/w of the composition.

Embodiment 159 is the ink applicator of any one of embodiments 150-158, wherein the preservative comprises EDTA.

Embodiment 160 is the ink applicator of embodiment 159, wherein the EDTA is present in an amount of about 0.01% to about 2% w/w of the composition.

Embodiment 161 is the ink applicator of any one of embodiments 159-160, wherein the EDTA is present in an amount of about 0.05% w/w of the composition.

Embodiment 162 is an ink applicator comprising a lower body coupled to an upper body, wherein the upper body comprises: a nib comprising a first end that is external to the upper body and a second end internal to the upper body, wherein the nib is configured to dispense a semi-permanent ink, and wherein the semi-permanent ink comprises:

a semi-permanent colorant, wherein the semi-permanent colorant comprises genipin, a genipin derivative, lawsone, a lawsone derivative, or combinations thereof;

a solvent; and a film-forming agent.

Embodiment 163 is the ink applicator of any of embodiments 1-161, wherein the ink applicator comprises an upper body; in particular wherein the lower body is coupled or couplable to the upper body, and/or wherein the upper body comprises a nib comprising a first end that is external to the upper body and a second end internal to the upper body, wherein the nib is configured to dispense a semi-permanent ink.

It is to be understood that while the disclosure has been described in conjunction with the detailed description thereof, the foregoing description is intended to illustrate and not limit the scope of the disclosure which is defined by the scope of the appended claims. Other aspects, advantages, and modification are within the scope of the following claims.

What is claimed is:

1. An ink applicator, comprising:

a lower body, comprising:

a reservoir contained in a cavity of the lower body; and a semi-permanent ink contained in the reservoir, wherein the semipermanent ink comprises:

a semi-permanent colorant, wherein the semi-permanent colorant comprises genipin, a genipin derivative, lawsone, a lawsone derivative, or combinations thereof;

a solvent;

a film-forming agent;

wherein the genipin derivative is a compound of Formula I:

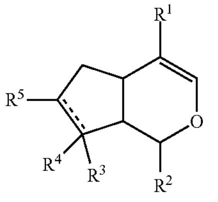

I wherein:

$R^1$ is —C(═O)$OR^6$ or $C_{1-6}$ alkyl, wherein said $C_{1-6}$ alkyl is optionally substituted with 1-5 $R^7$;

$R^6$ is H, $C_{1-6}$ alkyl, or $C_{6-10}$ aryl, wherein said $C_{1-6}$ alkyl and $C_{6-10}$ aryl are each optionally substituted with 1-5 $R^7$;

each $R^7$ is independently an electron withdrawing or an electron donating group;

$R^2$ is H, —$OR^9$, or OC(═O) $R^{9A}$;

$R^9$ is selected from the group consisting of: H, $C_{1-6}$ alkyl, $C_{6-10}$ aryl, and a hydroxyl-protecting group;

$R^{9A}$ is selected from $C_{1-6}$ alkyl and $C_{6-10}$ aryl, wherein the double bond is absent;

wherein if the double bond is absent, then $R^4$ and $R^5$ together with the carbon atoms to which they are attached form a 3-4 membered heterocyclic ring and $R^3$ is —OH or —$CH_2OH$; or wherein $R^{10}$ is selected from H, $C_{1-6}$ alkyl, alkoxy, oxo, —OH, —CH(═O), —C(═O)$OR^6$, phenyl, and phenyl substituted with 1-5 $R^7$; and $R^8$ is H or $R^7$.

2. The ink applicator of claim 1, wherein the reservoir comprises polyethylene terephthalate.

3. The ink applicator according to claim 1, comprising an upper body coupled to the lower body, the upper body comprising: a nib comprising a first end that is external to the upper body and a second end internal to the upper body.

4. The ink applicator of claim 1, wherein the reservoir is selectively removable.

5. The ink applicator of claim 1, wherein:

$R^1$ is —C(═O)$OR^6$ or phenyl substituted with 1-5 $R^7$;

$R^6$ is H, $C_{1-6}$ alkyl, or phenyl substituted with 1-5 $R^7$;

$R^2$ is H, —$OR^9$, or OC(═O) $R^9$;

$R^9$ is H or $C_{1-6}$ alkyl; and $R^{10}$ is selected from H, $C_{1-6}$ alkyl, alkoxy, oxo, —OH, —CH(═O) and phenyl substituted with 1-5 $R^7$.

6. The ink applicator of claim 1, wherein $R^1$ is —C(═O)$OR^6$ and $R^6$ is methyl; or wherein $R^1$ is —C(═O)$OR^6$ and $R^6$ is phenyl substituted with 1-5 $R^7$.

7. The ink applicator of claim 1, wherein $R^2$ is —OC(═O) $CH_3$; or wherein $R^2$ is —OH; or wherein $R^2$ is —$OR^9$ and $R^9$ is selected from the group consisting of: H, $C_{1-6}$ alkyl, tert-butyldimethylsilyl (TBS), trimethylsilyl (TMS), triethylsilyl (TES), and $C_{6-10}$ aryl.

8. The ink applicator of claim 1, wherein $R^9$ is selected from the group consisting of: H, $C_{1-6}$ alkyl, $C_{6-10}$ aryl, and a tri ($C_{1-6}$ alkyl) silyl.

9. The ink applicator of claim 1, wherein then $R^4$ and $R^5$ together with the carbon atoms to which they are attached form a 3-membered heterocyclic ring and $R^3$ is —$CH_2OH$; or wherein then $R^4$ and $R^5$ together with the carbon atoms to which they are attached form a 4-membered heterocyclic ring and $R^3$ is —OH.

10. The ink applicator of claim 1, wherein the genipin derivative is a compound selected from the group consisting of:

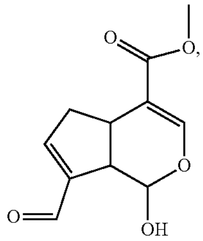

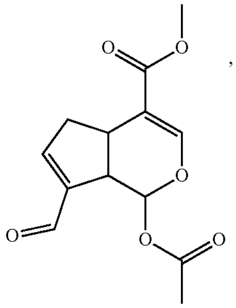

,

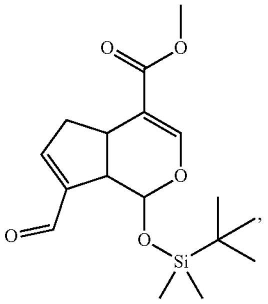

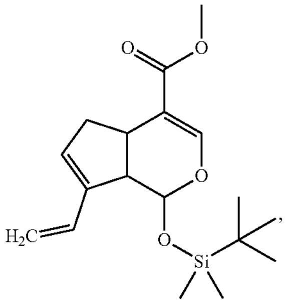

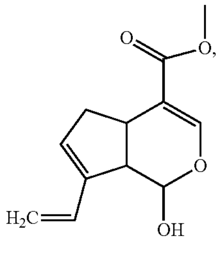

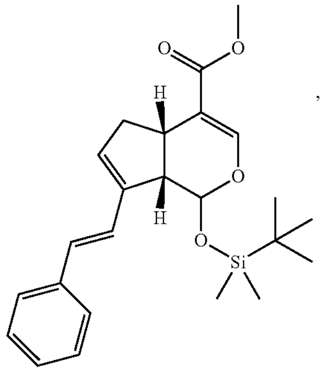

,

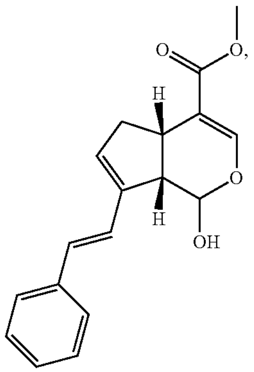

-continued

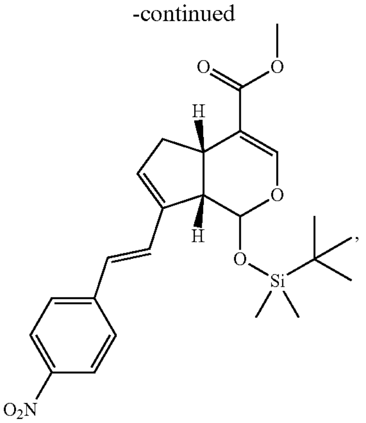

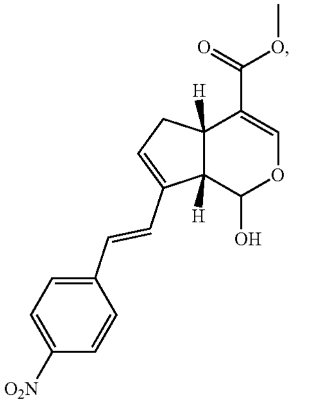

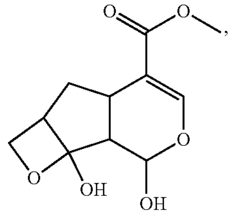

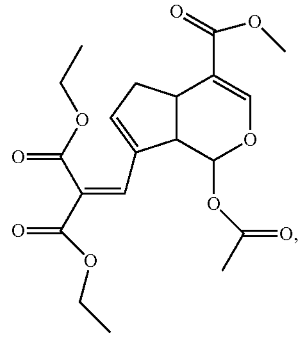

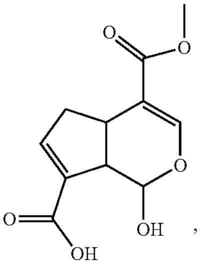

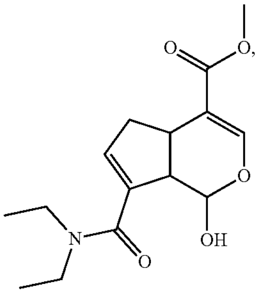

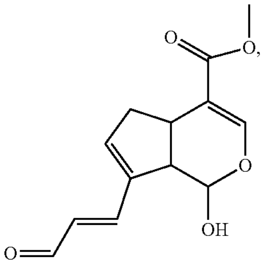

-continued

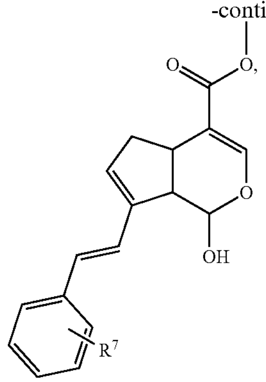

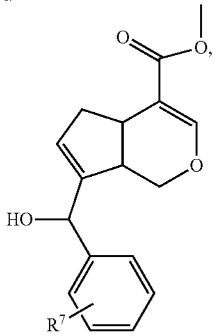

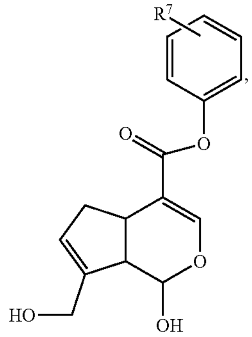

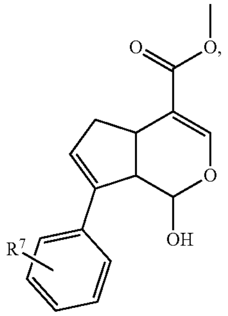

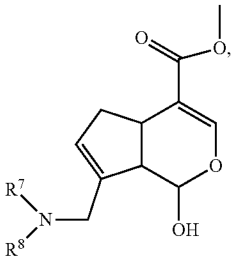

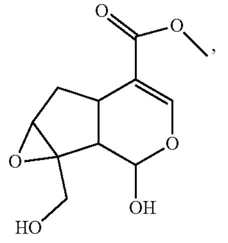

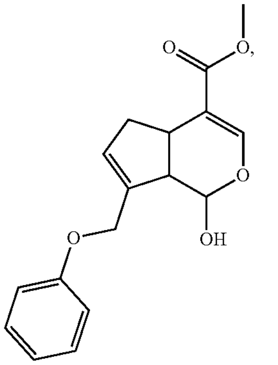

and

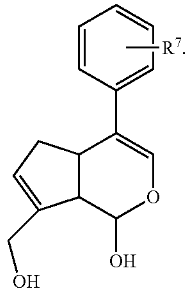

11. The ink applicator of claim 1, wherein R7 is selected from the group consisting of: —($C_{1-9}$ alkyl), —($C_{2-9}$ alkenyl), phenyl, —$NR^8R^8$, —$OR^8$, —NHC(═O)$R^8$, —OC(═O)$R^8$, —SR8, —$CO_2$—, —$SO_2CF_3$, —NO, —$NO_2$, —$SO_2R^8$, —CN, —$CR^{11}$, —$COR^{11}$, —CHO, —$CO_2R^8$, —C(═O)$NR^8R^8$, and halide;

wherein $R^8$ is selected from the group consisting of: H, —($C_{1-9}$ alkyl), and —($C_{2-9}$ alkenyl); and $R^{11}$ is halide.

12. The ink applicator of claim 1, wherein the solvent comprises water, methanol, ethanol, isopropanol, diethylene glycol monoethyl ether, or a combination thereof.

13. The ink applicator of claim 1 wherein the film-forming agent comprises a volatile silicon resin, polyvinylpyrrolidone, an acrylate, an acrylamide, a copolymer, an isododecane resin, or a combination thereof, and/or wherein the filmforming agent comprises polymethylsilsesquioxane, trimethylsiloxysilicate, polypropylsilsesquioxane, dimethicone, cyclopentasiloxane, dimethiconol crosspolymer, polysilicone-6, polysilicone-8, polysilicone-11, polysilicone-14, acrylates copolymer, styrene/acrylates copolymer, polyvinylpyrrolidone, acrylates/C 12-22 alkyl methacrylate copolymer, acrylates/polytrimethylsiloxymethacrylate copolymer, polyvinylpyrrolidone/vinyl acetate (VP/VA) copolymer, VP/dimethiconylacrylate/polycarbamyl/polyglycol ester, VP/dimethylaminoethylmethacrylate copolymer, VP/dimethylamino ethylmethacrylate/polycarbamyl polyglycol ester, VP/eicosene copolymer, VP/hexadecene copolymer, VP/methacrylamide/vinyl imidazole copolymer, VP/polycarbamyl polyglycol ester, VP/VA copolymer, polyester-1, polyester-2, polyester-3, polyester-4, polyester-5, polyester-7, polyester-8, and polyester-10, or a combination thereof, and more specifically wherein the film-forming agent is a combination of acrylates copolymer, polyvinylpyrrolidone, and styrene/acrylates copolymer.

14. The ink applicator according to claim 1, comprising an upper body wherein the lower body is coupled or couplable to the upper body, and/or wherein the upper body comprises a nib comprising a first end that is external to the upper body and a second end internal to the upper body, wherein the nib is configured to dispense a semi-permanent ink.

15. An ink applicator, comprising:

a lower body, comprising:

a reservoir contained in a cavity of the lower body; and a semi-permanent ink contained in the reservoir, wherein the semipermanent ink comprises:

a semi-permanent colorant, wherein the semi-permanent colorant comprises genipin, a genipin derivative, lawsone, a lawsone derivative, or combinations thereof;

a solvent;

a film-forming agent;

wherein the genipin derivative is a compound of Formula I:

I

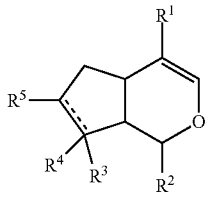

wherein:

$R^1$ is —C(═O)OR$^6$ or $C_{1-6}$ alkyl, wherein said $C_{1-6}$ alkyl is optionally substituted with 1-5 $R^7$;

$R^6$ is H, $C_{1-6}$ alkyl, or $C_{6-10}$ aryl, wherein said $C_{1-6}$ alkyl and $C_{6-10}$ aryl are each optionally substituted with 1-5 $R^7$;

each $R^7$ is independently an electron withdrawing or an electron donating group;

$R^2$ is H, —OR$^9$, or OC(═O)R$^{9A}$;

$R^9$ is selected from the group consisting of: H, $C_{1-6}$ alkyl, $C_{6-10}$ aryl, and a hydroxyl-protecting group;

$R^{9A}$ is selected from $C_{1-6}$ alkyl and $C_{6-10}$ aryl; and the dotted line indicates the optional presence of a double bond;

wherein if the double bond is absent, then $R^4$ and $R^5$ together with the carbon atoms to which they are attached form a 3-4 membered heterocyclic ring and $R^3$ is —OH or —$CH_2OH$; or if the double bond is present, then $R^4$ and $R^5$ are absent and $R^3$ is selected from the group consisting of: —NR$^7$R$^8$, —CH$_2$NR$^7$R$^8$, —C(═O)OR$^{10}$, —C(═O)NR$^{10}$R$^{10}$, —CH(═O), phenyl, —CHR$^{10}$R$^{10}$, —CH═CHR$^{10}$, —CH═CR$^{10}$R$^{10}$, —CH$_2$OR$^{10}$, and phenyl substituted with 1-5 $R^7$;

wherein $R^{10}$ is selected from H, $C_{1-6}$ alkyl, alkoxy, oxo, —OH, —CH(═O), —C(═O)OR$^6$, phenyl, and phenyl substituted with 1-5 $R^7$; and $R^8$ is H or $R^7$;

wherein the lawsone derivative is a compound of Formula III:

III

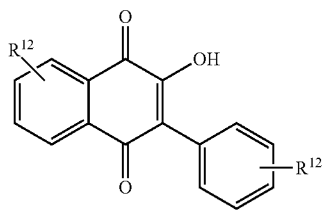

wherein $R^{12}$ is selected from the group consisting of: —($C_{1-9}$ alkyl), —($C_{2-9}$ alkenyl), phenyl, —NR$_8$R$_8$, —OR$_8$, —NHC(═O)R$_8$, —OC(═O)R$^8$, —SR$_8$, —CO$_2$—, —SO$_2$CF$_3$, —NO, —NO$_2$, —SO$_2$R$_8$, —CN, —CR$^{11}{}_3$, —COR$_{11}$, —CHO, —CO$_2$R$_8$, —C(═O)NR$_8$R$_8$, and halide; wherein $R_8$ is selected from the group consisting of: H, —($C_{1-9}$ alkyl), and —($C_{2-9}$ alkenyl); and $R_{11}$ is halide.

16. The ink applicator of claim 15, wherein the solvent comprises water, methanol, ethanol, isopropanol, diethylene glycol monoethyl ether, or a combination thereof.

17. The ink applicator of claim 15, wherein the film-forming agent comprises a volatile silicon resin, polyvinylpyrrolidone, an acrylate, an acrylamide, a copolymer, an isododecane resin, or a combination thereof, and/or wherein the filmforming agent comprises polymethylsilsesquioxane, trimethylsiloxysilicate, polypropylsilsesquioxane, dimethicone, cyclopentasiloxane, dimethiconol crosspolymer, polysilicone-6, polysilicone-8, polysilicone-11, polysilicone-14, acrylates copolymer, styrene/acrylates copolymer, polyvinylpyrrolidone, acrylates/C 12-22 alkyl methacrylate copolymer, acrylates/polytrimethylsiloxymethacrylate copolymer, polyvinylpyrrolidone/vinyl acetate (VP/VA) copolymer, VP/dimethiconylacrylate/polycarbamyl/polyglycol ester, VP/dimethylaminoethylmethacrylate copolymer, VP/dimethylamino ethylmethacrylate/polycarbamyl polyglycol ester, VP/eicosene copolymer, VP/hexadecene copolymer, VP/methacrylamide/vinyl imidazole copolymer, VP/polycarbamyl polyglycol ester, VP/VA copolymer, polyester-1, polyester-2, polyester-3, polyester-4, polyester-5, polyester-7, polyester-8, and polyester-10, or a combination thereof, and more specifically wherein the film-forming agent is a combination of acrylates copolymer, polyvinylpyrrolidone, and styrene/acrylates copolymer.

18. The ink applicator according to claim 15, comprising an upper body wherein the lower body is coupled or couplable to the upper body, and/or wherein the upper body comprises a nib comprising a first end that is external to the upper body and a second end internal to the upper body, wherein the nib is configured to dispense a semi-permanent ink.

19. The ink applicator of claim 15, wherein the reservoir comprises polyethylene terephthalate.

20. The ink applicator according to claim 15, comprising an upper body coupled to the lower body, the upper body comprising: a nib comprising a first end that is external to the upper body and a second end internal to the upper body.

21. The ink applicator of claim 15, wherein the reservoir is selectively removable.

22. The ink applicator of claim 15, wherein:

$R^1$ is —C(═O)$OR^6$ or phenyl substituted with 1-5 $R^7$;

$R^6$ is H, $C_{1-6}$ alkyl, or phenyl substituted with 1-5 $R^7$;

$R^2$ is H, —$OR^9$, or OC(═O)$R^9$;

$R^9$ is H or $C_{1-6}$ alkyl;

if the double bond is present, then $R^4$ and $R^5$ are absent and $R^3$ is selected from the group consisting of: —$NR^7$ $R^8$, —$CH_2NR^7R^8$, —C(═O)$OR^{10}$, —CH(═O), phenyl, —$CHR^{10}R^{10}$, —CH═$CHR^{10}$, —$CH_2OR^{10}$, diethyl malonate, and phenyl substituted with 1-5 $R^7$; and $R^{10}$ is selected from H, $C_{1-6}$ alkyl, alkoxy, oxo, —OH, —CH(═O) and phenyl substituted with 1-5 $R^7$.

23. The ink applicator of claim 15, wherein $R^1$ is —C(═O)$OR^6$ and $R^6$ is methyl; or wherein $R^1$ is —C(═O)$OR^6$ and $R^6$ is phenyl substituted with 1-5 $R^7$.

24. The ink applicator of claim 15, wherein $R^2$ is —OC(═O)$CH_3$; or wherein $R^2$ is —OH; or wherein $R^2$ is —$OR^9$ and $R^9$ is selected from the group consisting of: H, $C_{1-6}$ alkyl, tert-butyldimethylsilyl (TBS), trimethylsilyl (TMS), triethylsilyl (TES), and $C_{6-10}$ aryl.

25. The ink applicator of claim 15, wherein $R^9$ is selected from the group consisting of: H, $C_{1-6}$ alkyl, $C_{6-10}$ aryl, and a tri($C_{1-6}$ alkyl)silyl.

26. The ink applicator of claim 15, wherein then $R^4$ and $R^5$ together with the carbon atoms to which they are attached form a 3-membered heterocyclic ring and $R^3$ is —$CH_2OH$; or wherein then $R^4$ and $R^5$ together with the carbon atoms to which they are attached form a 4-membered heterocyclic ring and $R^3$ is —OH.

27. The ink applicator of claim 15, wherein the double bond is present.

28. The ink applicator of claim 27, wherein $R^3$ is selected from the group consisting of:

—$NR^7R^8$, —$CH_2NR^7R^8$, —CH(═O)$OR^{10}$, —C(═O)N$R^{10}R^{10}$, —CH(═O), phenyl, —$CHR^{10}R^{10}$, —CH═$CHR^{10}$, —CH═$CR^{10}R^{10}$, —$CH_2OR^{10}$, and phenyl substituted with 1-5 $R^7$;

$R^1$ is —C(═O)OH;

$R^2$ is —OH; and $R^{10}$ is selected from H, $C_{1-6}$ alkyl, alkoxy, oxo, —OH, —CH(═O), —C(═O)$OR^6$, phenyl, and phenyl substituted with 1-5 $R^7$, and/or wherein $R^3$ is selected from the group consisting of:—$NR^7R^8$, —$CH_2$—$NR^7R^8$, —C(═O)$OR^{10}$, —CH(═O), phenyl, —$CHR^{10}R^{10}$, —CH═$CHR^{10}$, —C(═O)$NR^{10}R^{10}$, —$CH_2OR^{10}$ and phenyl substituted with 1-5 $R^7$;

$R^1$ is —C(═O)OH; and $R^2$ is —$OR^9$ and $R^9$ is selected from the group consisting of: H, $C_{1-6}$ alkyl, tert-butyldimethylsilyl (TBS), trimethylsilyl (TMS), triethylsilyl (TES), and $C_{6-10}$ aryl, and/or wherein $R^3$ is selected from the group consisting of:

$NR^7R^8$, —$CH_2NR^7R^8$, —C(═O)$OR^{10}$, —CH(═O), phenyl, —$CHR^{10}R^{10}$, —CH═$CHR^{10}$ —$CH_2OR^{10}$, diethyl malonate, and phenyl substituted with 1-5 $R^7$;

$R^1$ is —C(═O)OH; and $R^2$ is —OH.

29. The ink applicator of claim 15, wherein the genipin derivative is a compound selected from the group consisting of:

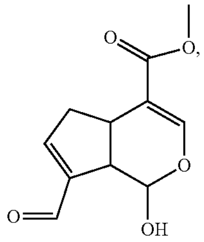

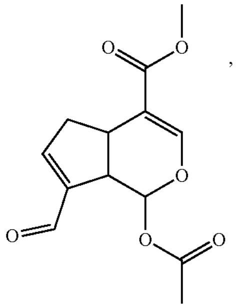

,

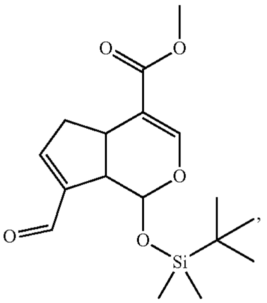

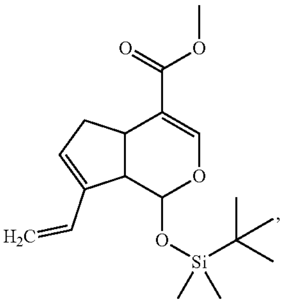

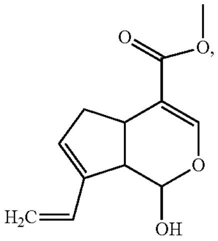

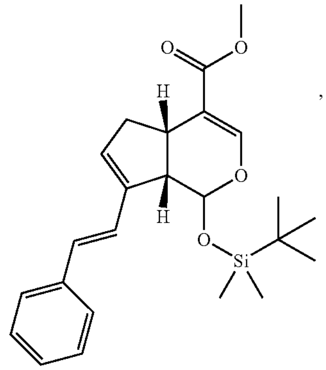

,

-continued
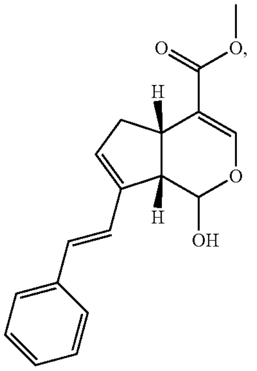
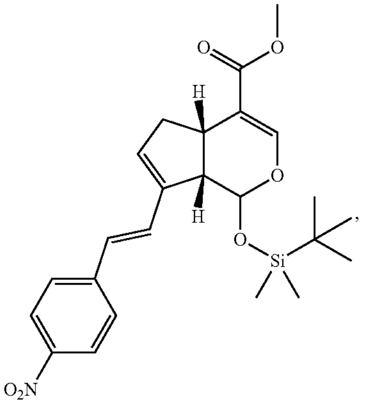
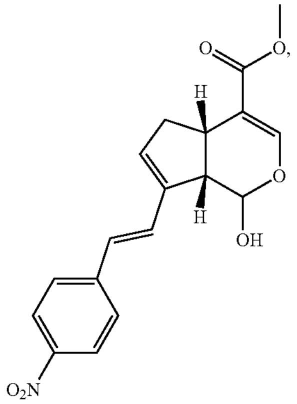
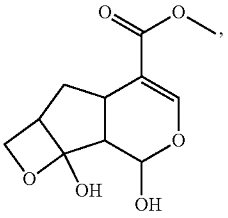
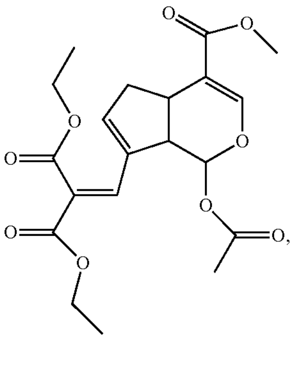
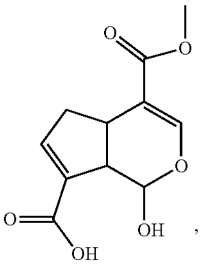
-continued
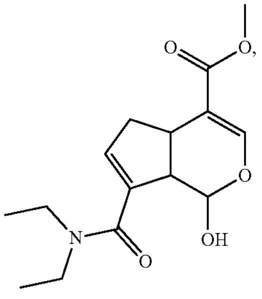
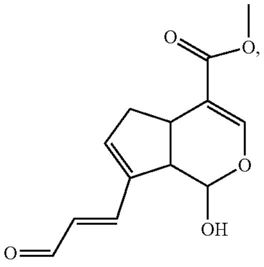
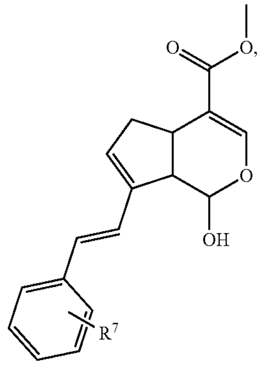
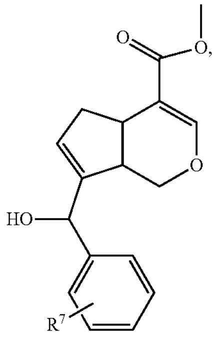
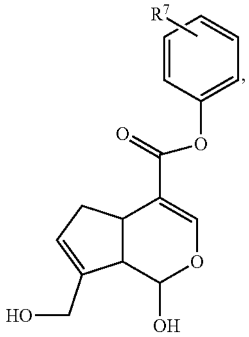
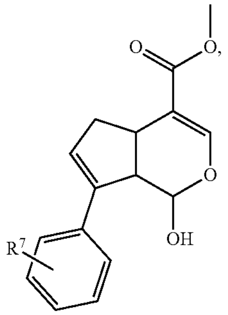
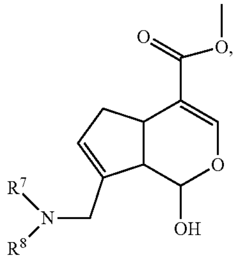
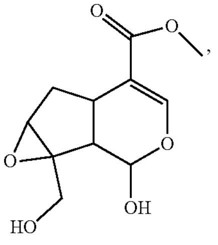
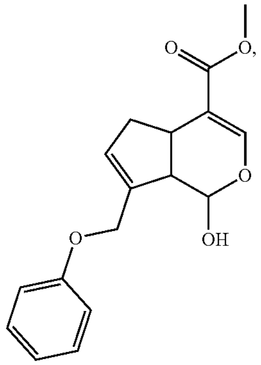
and
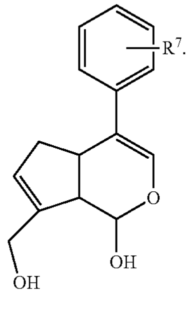
30. The ink applicator of claim 15, wherein $R^7$ is selected from the group consisting of: —($C_{1-9}$ alkyl), —($C_{2-9}$ alkenyl), phenyl, —$NR^8R^8$, —$OR^8$, —NHC(═O)$R^8$, —OC (═O)$R^8$, —SR8, —$CO_2$—, —$SO_2CF_3$, —NO, —$NO_2$, —$SO_2R^8$, —CN, —$CR^{11}$, —$COR^{11}$, —CHO, —$CO_2R^8$, —C(═O)$NR^8R^8$, and halide;

wherein $R^8$ is selected from the group consisting of: H, —($C_{1-9}$ alkyl), and —($C_{2-9}$ alkenyl); and $R^{11}$ is halide.

* * * * *